United States Patent
Fukuda et al.

(10) Patent No.: US 10,406,819 B2
(45) Date of Patent: Sep. 10, 2019

(54) LIQUID EJECTING APPARATUS, COLOR MEASURING METHOD, AND DRIVING METHOD FOR LIQUID EJECTING APPARATUS

(71) Applicant: SEIKO EPSON CORPORATION, Tokyo (JP)

(72) Inventors: Masako Fukuda, Shiojiri (JP); Masashi Kanai, Azumino (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 15/714,582

(22) Filed: Sep. 25, 2017

(65) Prior Publication Data

US 2018/0086097 A1    Mar. 29, 2018

(30) Foreign Application Priority Data

Sep. 26, 2016  (JP) .................... 2016-186763
Jul. 21, 2017  (JP) .................... 2017-142276

(51) Int. Cl.
| | |
|---|---|
| G01J 3/46 | (2006.01) |
| B41J 2/21 | (2006.01) |
| B41J 13/00 | (2006.01) |
| G01N 21/25 | (2006.01) |
| B41J 11/00 | (2006.01) |
| G01J 1/02 | (2006.01) |

(Continued)

(52) U.S. Cl.
CPC ........... B41J 2/2103 (2013.01); B41J 11/009 (2013.01); B41J 13/0009 (2013.01); G01J 1/0228 (2013.01); G01J 1/0242 (2013.01); G01J 3/0289 (2013.01); G01J 3/502 (2013.01); G01N 21/25 (2013.01)

(58) Field of Classification Search
CPC .... B41J 2/2103; B41J 11/009; B41J 13/0009; G01J 3/46
See application file for complete search history.

(56) References Cited

U.S. PATENT DOCUMENTS

| | | |
|---|---|---|
| 2012/0212824 A1 | 8/2012 | Sakurai |
| 2013/0127946 A1 | 5/2013 | Kanai |

(Continued)

FOREIGN PATENT DOCUMENTS

| | | |
|---|---|---|
| JP | H10-137963 | 5/1998 |
| JP | 2000-326585 | 11/2000 |
| JP | 2002-022538 | 1/2002 |

(Continued)

*Primary Examiner* — Jason S Uhlenhake
(74) *Attorney, Agent, or Firm* — Workman Nydegger

(57) ABSTRACT

A liquid ejecting apparatus includes a liquid ejecting head that ejects a liquid onto a medium, a color measuring unit configured to measure color of a surface of the medium, having a light projecting unit emits a light flux to the surface of the medium and a light receiving unit receiving light obtained by reflecting light emitted from the light projecting unit on the surface of the medium, a changing unit configured to change a reflection position of light, which matches the central axis of the light flux from the light projecting unit, on the medium, and a control unit configured to set the reflection position where color measurement data indicating the highest lightness of the color measurement data pieces of the surface of the medium is obtained as a color measurement position.

8 Claims, 27 Drawing Sheets

(51) Int. Cl.
*G01J 3/02* (2006.01)
*G01J 3/50* (2006.01)

(56) References Cited

U.S. PATENT DOCUMENTS

| | | |
|---|---|---|
| 2013/0135408 A1 | 5/2013 | Masuda et al. |
| 2013/0258368 A1* | 10/2013 | Shigemoto ......... H04N 1/00082 |
| | | 358/1.9 |

FOREIGN PATENT DOCUMENTS

| JP | 2005-125605 | 5/2005 |
|----|-------------|--------|
| JP | 5273025 B | 5/2013 |
| JP | 2013-107269 | 6/2013 |
| JP | 2013-129187 | 7/2013 |
| JP | 2013-228370 | 11/2013 |
| JP | 5708009 B | 3/2015 |

* cited by examiner

ILLUMINANCE DISTRIBUTION ON MEDIUM

ILLUMINANCE DISTRIBUTION ON MEDIUM

LIQUID EJECTING APPARATUS, COLOR MEASURING METHOD, AND DRIVING METHOD FOR LIQUID EJECTING APPARATUS

BACKGROUND

1. Technical Field

The present invention relates to a liquid ejecting apparatus, which includes a liquid ejecting head ejecting a liquid onto a medium, and a color measuring unit measuring a color of the liquid landed on the medium, a color measuring method, and a driving method for a liquid ejecting apparatus, and particularly to an ink jet recording apparatus, a color measuring method, and a driving method for an ink jet recording apparatus.

2. Related Art

In an ink jet recording apparatus, which is a representative example of a liquid ejecting apparatus, variations in the reproducibility of printed colors occur according to the characteristics of a medium, on which printing is performed, and the characteristics of a recording head that discharges an ink. For this reason, by the ink jet recording apparatus printing a patch in a reference color and a color measuring device included in the recording apparatus measuring the colors of the patch, color conversion information is generated based on a difference between the color measurement value of the patch and the color specification value of the reference color in a standard color space. Printing with high color reproducibility by converting input image data based on the color conversion information generated from the color measurement value and executing printing is proposed (for example, refer to JP-A-2013-228370).

At this time, since the reproducibility of colors is different for each of different types of media, it is necessary to measure colors for each of different types of media. However, there is a problem in which colors cannot be measured with high accuracy since there are variations in the thicknesses of different types of media.

For this reason, in a case where color measurement results are corrected at a position with respect to a medium of the color measuring device after color measurement as in JP-A-2013-228370, the accuracy of color measurement results becomes lower.

Such a problem arises not only in ink jet recording apparatuses but also in liquid ejecting apparatuses ejecting a liquid other than an ink.

SUMMARY

An advantage of some aspects of the invention is to provide a liquid ejecting apparatus including a color measuring device which can perform highly accurate color measurement, a color measuring method, and a driving method for a liquid ejecting apparatus.

According to an aspect of the invention, there is provided a liquid ejecting apparatus including a liquid ejecting head that ejects a liquid onto a medium, a color measuring unit that has a light projecting unit, which emits a light flux to a surface to be measured of the medium with light, and a light receiving unit, which receives reflected light obtained by reflecting light emitted from the light projecting unit on the surface to be measured of the medium, and that performs color measurement on the surface to be measured, a changing unit that changes a reflection position of light, which matches a central axis of light flux emitted from the light projecting unit, on the medium, and a control unit that sets the reflection position where color measurement data indicating the highest lightness is obtained as a color measurement position, out of color measurement data pieces of the surface to be measured, which are obtained by the light receiving unit receiving light and the color measuring unit measuring colors at the reflection position changed by the changing unit.

In such an aspect, highly accurate color measurement can be performed since color measurement can be performed at a reflection position where lightness is the highest as a color measurement position.

It is preferable that the control unit control the changing unit to set a position where color measurement data indicating the highest lightness is obtained by the color measuring unit measuring colors when the light receiving unit receives light reflected by an outer surface of a supporting member supporting an opposite surface of the surface to be measured of the medium as a reference position, and acquire a thickness of the medium based on the reference position and the color measurement position. According to this, a sensor that measures the thickness of the medium is unnecessary since the thickness of the medium can be measured by the color measuring unit. Thus, costs can be reduced and miniaturization can be achieved.

In addition, it is preferable that the control unit identify the medium based on the thickness of the medium and a color measurement result of a non-landing region where the liquid is not landed on the medium, of which colors are measured by the color measuring unit at the color measurement position. According to this, an optimal print setting for a medium can be performed and printing quality can be improved by identifying the medium based on the thickness of the medium and the color measurement results of the non-landing region of the medium.

In addition, it is preferable that the changing unit change an interval between the color measuring unit and the medium in a normal line direction of the surface to be measured of the medium. According to this, a reflection position can be easily changed by changing an interval between the color measuring unit and the medium in the normal line direction of the surface to be measured of the medium.

According to another aspect of the invention, there is provided a liquid ejecting apparatus including a liquid ejecting head that ejects a liquid onto a medium, a color measuring unit that has a light projecting unit, which emits a light flux to a surface to be measured of the medium with light, and a light receiving unit, which receives reflected light obtained by reflecting light emitted from the light projecting unit on the surface to be measured of the medium, and that performs color measurement on the surface to be measured, a changing unit that changes a reflection position of light, which matches a central axis of light flux emitted from the light projecting unit, on the surface to be measured, and a control unit that sets a color measurement position based on a difference between the reflection position where color measurement data indicating the highest lightness is obtained, out of color measurement data pieces, which are obtained by the color measuring unit measuring colors at the reflection position changed by the changing unit, and a reference position set in advance.

In such an aspect, highly accurate color measurement can be performed since color measurement can be performed at a reflection position where lightness is the highest as a color measurement position. In addition, even when there are variations in the thickness of the medium, color measurement can be performed with high accuracy by setting a color measurement position based on a difference between the reflection position, at which lightness is the highest, and the reference position set in advance.

In addition, it is preferable that the changing unit change an interval between the light projecting unit and the light receiving unit in a plane direction of parallel to the surface to be measured, or the changing unit change an irradiation angle of the light projecting unit or a light receiving angle of the light receiving unit with respect to a normal line of the surface to be measured. According to this, a reflection position can be easily changed by changing an interval between the light projecting unit and the light receiving unit in the plane direction parallel to the surface to be measured or by changing an irradiation angle or a light receiving angle.

In addition, it is preferable that the color measuring unit be provided on an upstream side of the liquid ejecting head in a transporting direction of the medium. According to this, the adhesion of mist generated by ejecting the liquid from the liquid ejecting head to the color measuring unit can be suppressed.

In addition, it is preferable that the liquid ejecting head and the color measuring unit be mounted on a carriage that is provided so as to be movable in a direction orthogonal to a transporting direction of the medium and a direction orthogonal to the surface to be measured. According to this, color measurement can be performed by the color measuring unit over the entire area of the medium. In addition, by mounting the color measuring unit and the liquid ejecting head on the same carriage, the number of components is decreased. Thus, costs can be reduced and miniaturization can be achieved.

In addition, it is preferable that the control unit color-convert print data with color conversion information that is based on a color measurement value, which is obtained by the color measuring unit measuring colors of the surface to be measured at the color measurement position, or a color measurement value of a patch printed on the surface to be measured. According to this, highly accurate color conversion information can be acquired based on the color measurement value of the surface to be measured or the color measurement value of the patch printed on the surface to be measured, and printing, in which color reproducibility is improved, can be realized.

According to still another aspect of the invention, there is provided a color measuring method in which a color measuring unit that has a light projecting unit, which emits a light flux to a surface to be measured of a medium with light, and a light receiving unit, which receives reflected light obtained by reflecting light emitted from the light projecting unit on the surface to be measured of the medium, and that performs color measurement on the surface to be measured, is used, the method including measuring colors of the surface to be measured by changing a reflection position of light, which matches a central axis of light flux emitted from the light projecting unit, on the medium and by receiving the reflected light by means of the light receiving unit, and measuring colors by means of the color measuring unit at the reflection position where lightness of the surface to be measured is the highest, which is obtained by the light receiving unit receiving light and the color measuring unit measuring colors, out of the changed reflection positions, as a color measurement position.

In such an aspect, highly accurate color measurement can be performed since color measurement can be performed at a reflection position where lightness is the highest as a color measurement position.

According to still another aspect of the invention, there is provided a driving method for a liquid ejecting apparatus including a liquid ejecting head that ejects a liquid onto a medium and a color measuring unit that has a light projecting unit which emits a light flux to a surface to be measured of the medium with light, and a light receiving unit which receives light, which is emitted from the light projecting unit and reflected by the surface to be measured of the medium, and that performs color measurement on the surface to be measured of the medium. The driving method includes measuring a first color measurement value including a value indicating lightness of the surface to be measured of the medium by setting the light projecting unit, the light receiving unit, and the medium at a first relative position, and by receiving light, which is emitted from the light projecting unit and is reflected by the surface to be measured of the medium, by means of the light receiving unit, measuring a second color measurement value indicating lightness of the surface to be measured of the medium by setting the light projecting unit, the light receiving unit, and the medium at a second relative position, which is different from the first relative position, and by receiving light, which is emitted from the light projecting unit and is reflected by the surface to be measured of the medium, by means of the light receiving unit, setting the first relative position as a color measurement position in a case where lightness indicated by the first color measurement value is higher than lightness indicated by the second color measurement value, and color-converting print data with color conversion information that is based on colors of the medium measured at the color measurement position or a color measurement value of a patch printed on the medium.

In such an aspect, highly accurate color measurement can be performed by performing color measurement at the first relative position where the first color measurement value indicating higher lightness than the lightness indicated by the second color measurement value is measured as a color measurement position. In addition, color measurement time can be shortened since color measurement may be performed at at least two relative positions, including the first relative position and the second relative position.

Herein, it is preferable that setting the light projecting unit, the light receiving unit, and the medium at a plurality of relative positions, which are three or more of different relative positions among the light projecting unit, the light receiving unit, and the medium, including the first relative position and the second relative position, and measuring a color measurement value indicating lightness of the surface to be measured of the medium at each of the plurality of relative positions by receiving light, which is emitted from the light projecting unit and is reflected by the surface to be measured of the medium, by means of the light receiving unit be further included. According to this, by performing color measurement at the plurality of relative positions, a distance between the central axis of light flux emitted from the light projecting unit and the optical axis of the optical system for light receiving of the light receiving unit is made as short as possible, colors can be measured at high lightness, and color measurement accuracy can be increased.

In addition, it is preferable that the lightness indicated by the first color measurement value be the highest lightness, out of lightness levels indicated by color measurement values measured at the plurality of relative positions.

According to this, colors can be measured at high lightness and color measurement accuracy can be increased by making a distance between the central axis of light flux emitted from the light projecting unit and the optical axis of the optical system for light receiving of the light receiving unit as short as possible.

According to still another aspect of the invention, there is provided a driving method for a liquid ejecting apparatus including a liquid ejecting head that ejects a liquid onto a medium and a color measuring unit that has a light projecting unit which emits a light flux to a surface to be measured of the medium with light, and a light receiving unit which receives light, which is emitted from the light projecting unit and reflected by the surface to be measured of the medium, and that performs color measurement on the surface to be measured of the medium. The driving method includes measuring a first color measurement value including a value indicating lightness of the surface to be measured of the medium by setting the light projecting unit, the light receiving unit, and the medium at a first relative position, and by receiving light, which is emitted from the light projecting unit and is reflected by the surface to be measured of the medium, by means of the light receiving unit, measuring a second color measurement value indicating lightness of the surface to be measured of the medium by setting the light projecting unit, the light receiving unit, and the medium at a second relative position, which is different from the first relative position, and by receiving light, which is emitted from the light projecting unit and is reflected by the surface to be measured of the medium, by means of the light receiving unit, setting a relative position among the light projecting unit, the light receiving unit, and the medium as a color measurement position based on a difference between the first relative position and a reference relative position set in advance in a case where lightness indicated by the first color measurement value is higher than lightness indicated by the second color measurement value, and color-converting print data with color conversion information that is based on colors of the medium measured at the color measurement position or a color measurement value of a patch printed on the medium.

In such an aspect, in a case where the first color measurement value obtained at the first relative position is higher than the second color measurement value obtained at the second relative position in terms of lightness, color measurement is performed based on a difference between the first relative position and the reference relative position by setting the light projecting unit, the light receiving unit, and the medium at the color measurement position, to which the same color measurement condition is applied as in the reference relative position. Thus, even when there are variations in the thickness of the medium, colors can be measured at the color measurement position under a color measurement condition, in particular, a condition, in which the height of the color measuring unit from the surface to be measured is the same at all times, and highly accurate color measurement can be performed.

Herein, it is preferable that an interval between the light projecting unit and the light receiving unit in a direction intersecting a normal line direction of the surface to be measured of the medium differ at the first relative position and the second relative position. According to this, a reflection position can be easily changed by changing an interval between the light projecting unit and the light receiving unit in a direction intersecting the normal line direction of the surface to be measured.

In addition, it is preferable that moving the color measuring unit in the normal line direction of the surface to be measured by a distance calculated from a difference between the interval between the light projecting unit and the light receiving unit, which is at the first relative position, and the interval between the light projecting unit and the light receiving unit, which is at the reference relative position set in advance, in a case where the lightness indicated by the first color measurement value is higher than the lightness indicated by the second color measurement value be further included. According to this, even when variations in the thickness of the medium occur, colors can be measured under a condition, in which the height of the color measuring unit from the surface to be measured is the same at all times, at the color measurement position, and highly accurate color measurement can be performed.

In addition, it is preferable that an angle of a central axis of light flux, which is emitted from the light projecting unit, with respect to a normal line of the surface to be measured differ at the first relative position and the second relative position. According to this, a reflection position can be easily changed by changing an irradiation angle or a light receiving angle.

In addition, it is preferable that moving the color measuring unit in the normal line direction of the surface to be measured by a distance calculated from a difference between the angle of the central axis of the light flux, which is emitted from the light projecting unit, with respect to the normal line of the surface to be measured, which is the at the first relative position, and the angle of the central axis of the light flux, which is emitted from the light projecting unit, with respect to the normal line of the surface to be measured, which is at the reference relative position set in advance, in a case where the lightness indicated by the first color measurement value is higher than the lightness indicated by the second color measurement value be further included. According to this, even when variations in the thickness of the medium occur, colors can be measured under a condition, in which the height of the color measuring unit from the surface to be measured is the same at all times, at the color measurement position, and highly accurate color measurement can be performed.

In addition, it is preferable that measuring a third color measurement value including a value indicating lightness of the supporting surface of the supporting member by setting the light projecting unit, the light receiving unit, and a supporting member supporting an opposite surface of the surface to be measured of the medium at a third relative position, and by receiving light, which is emitted from the light projecting unit and is reflected by the supporting surface of the supporting member supporting the medium, by means of the light receiving unit, measuring a fourth color measurement value indicating lightness of the supporting surface of the supporting member by setting the light projecting unit, the light receiving unit, and the supporting member at a fourth relative position, which is different from the third relative position, and by receiving light, which is emitted from the light projecting unit and is reflected by the supporting surface of the supporting member, by means of the light receiving unit, setting the third relative position as a reference position in a case where lightness indicated by the third color measurement value is higher than lightness indicated by the fourth color measurement value, and detecting a thickness of the medium from a difference between the color measurement position and the reference position be further included. According to this, by the color measuring unit detecting the thickness of the medium, costs can be reduced since a separate sensor that measures the thickness of the medium is unnecessary, and miniaturization can be achieved since a space to dispose the sensor is unnecessary. In addition, a paper gap, which is an interval between the liquid ejecting head and the medium, can be controlled with high accuracy by acquiring the thickness of the medium.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, the invention will be described in detail based on embodiments.

Embodiment 1

Figure 1:
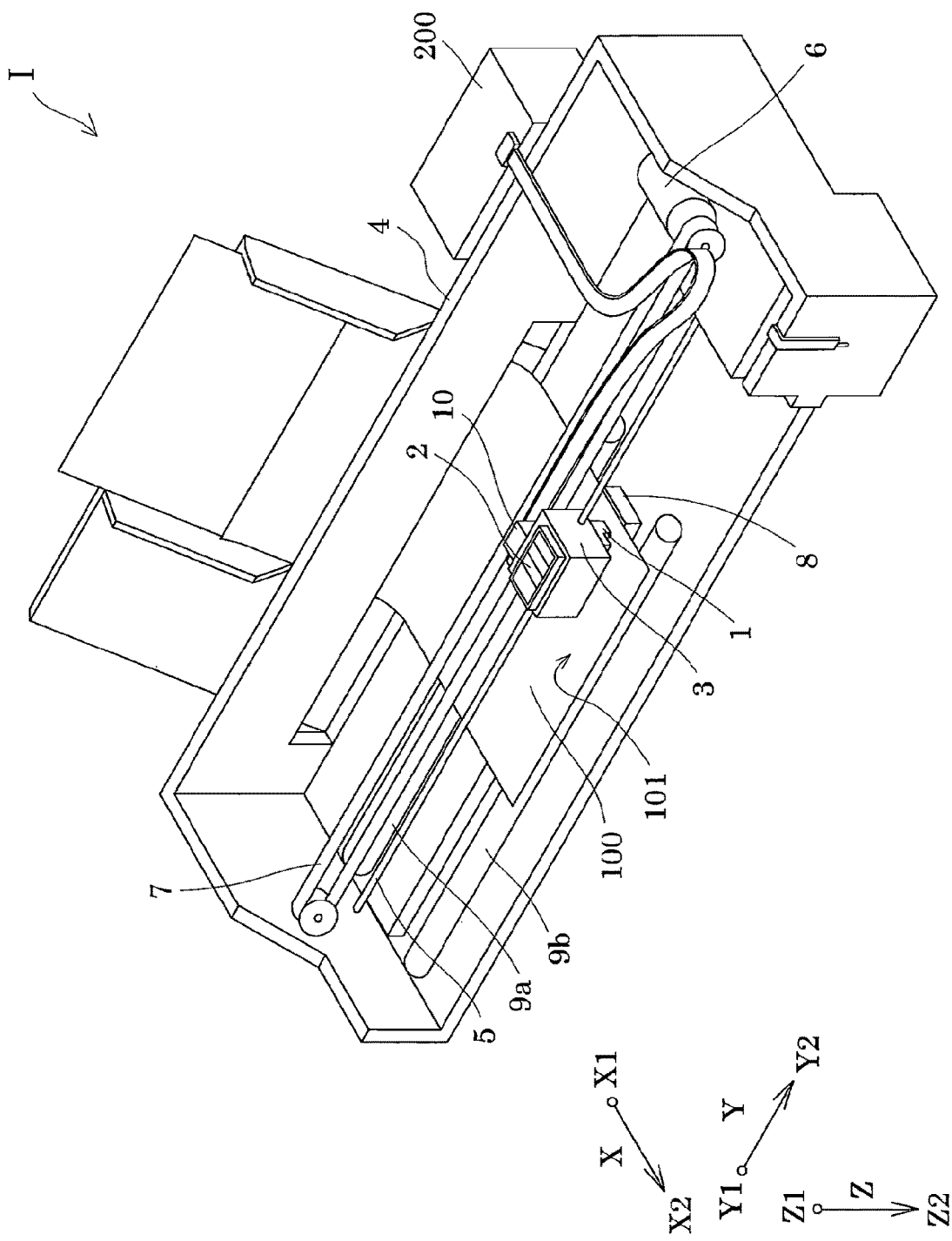
FIG. 1 is a schematic view of a recording apparatus according to Embodiment 1.
Figure 2:
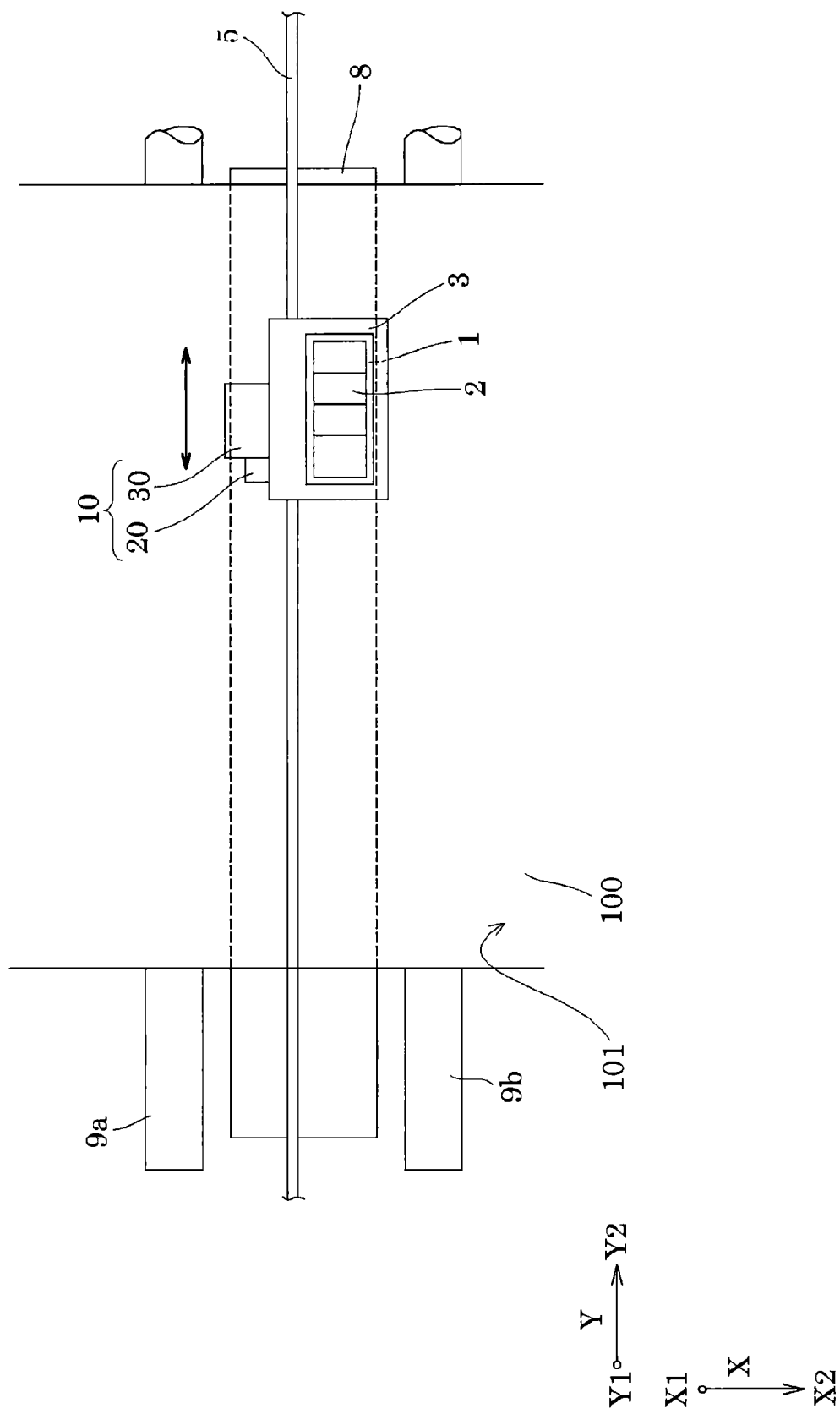
FIG. 2 is a plan view of main portions of the recording apparatus according to Embodiment 1.
Figure 3:
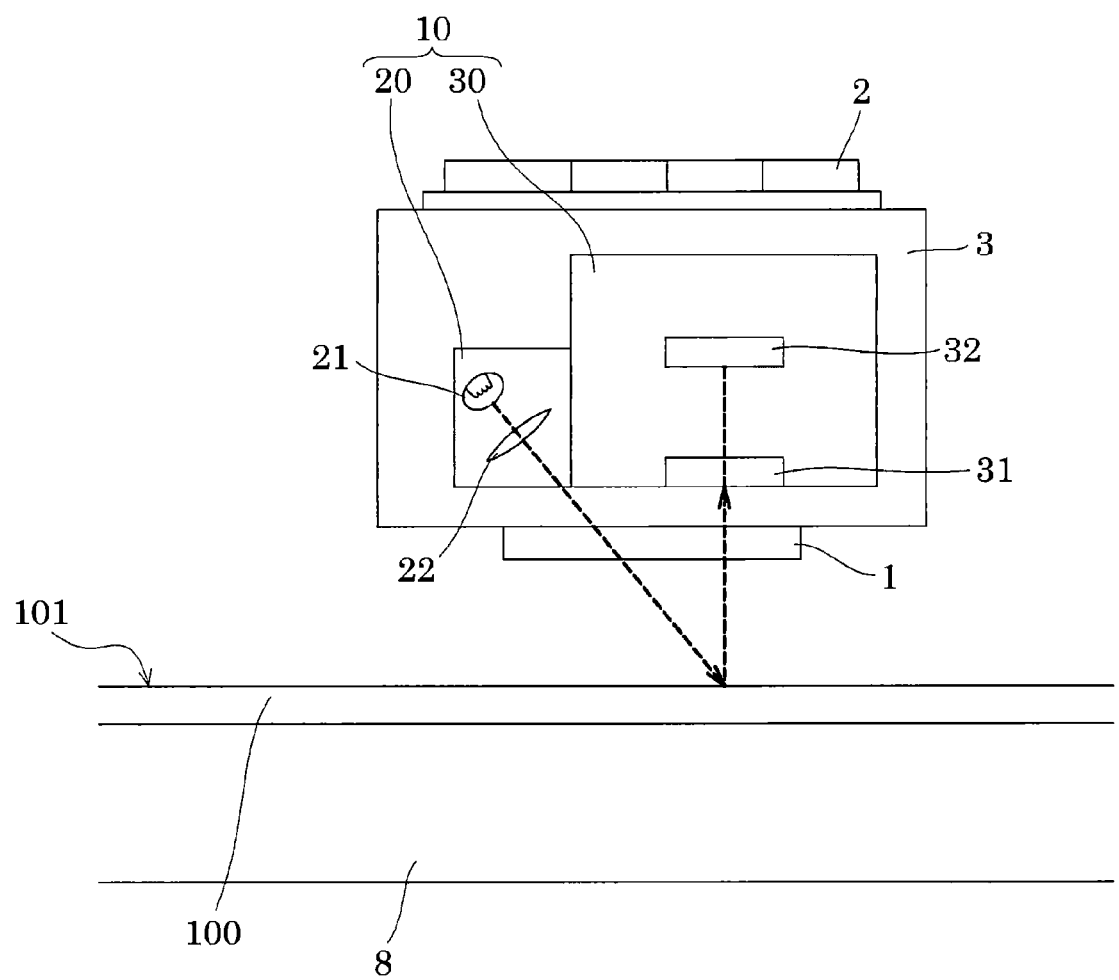
FIG. 3 is a side view of the main portions of the recording apparatus according to Embodiment 1.

FIG. 1 is a view illustrating a schematic configuration of an ink jet recording apparatus, which is an example of a liquid ejecting apparatus according to Embodiment 1 of the invention, FIG. 2 is a plan view illustrating main portions of the ink jet recording apparatus, and FIG. 3 is a side view illustrating the main portions of the ink jet recording apparatus.

As illustrated, an ink jet recording apparatus I includes an ink jet recording head 1 (hereinafter, also referred to as a recording head 1), which discharges an ink as a liquid. An ink cartridge 2 that configures an ink supplier is detachably provided in the recording head 1. Such a recording head 1 is mounted in a carriage 3.

The carriage 3, on which the recording head 1 is mounted, is provided on a carriage shaft 5 attached to the apparatus main body 4 so as to be movable in a shaft direction. The carriage 3, on which the recording head 1 is mounted, is moved along the carriage shaft 5 by drive force from a driving motor 6 being transmitted to the carriage 3 via a plurality of gears (not illustrated) and a timing belt 7.

A supporting member 8 supporting the opposite surface of a surface onto which ink droplets land, that is a so-called print surface, and a surface to be measured 101 of a recording sheet 100, which is a medium, is provided in the apparatus main body 4.

In addition, transporters that transport the recording sheet 100 onto the supporting member 8 and that transport the recording sheet 100, on which printing and color measurement are performed on the supporting member 8, from the supporting member 8 is provided in the apparatus main body 4. In the embodiment, a first transporter 9a and a second transporter 9b are provided as transporters at positions where the supporting member 8 are interposed therebetween. A direction in which the first transporter 9a and second transporter 9b are spaced away from each other is a transporting direction in which the recording sheet 100 is transported and is referred to as a first direction X. An upstream side in the transporting direction of the recording sheet 100 is referred to as X1, and a downstream side is referred to as X2.

Specifically, the first transporter 9a is provided on the upstream side of the recording head 1 in the transporting direction of the recording sheet 100, that is, on an X1 side in the first direction X. The first transporter 9a transports the recording sheet 100 to a position where the recording sheet 100 and the recording head 1 face each other, that is, onto the supporting member 8. In addition, the second transporter 9b is provided on the downstream side of the recording head 1 in the transporting direction of the recording sheet 100, that is, on an X2 side in the first direction X. The second transporter 9b transports the recording sheet 100 on the supporting member 8 toward the X2 side in the first direction X. The first transporter 9a and the second transporter 9b are formed of transporting rollers in the embodiment. The first transporter 9a and the second transporter 9b may be belts or drums without being limited to the transporting rollers.

With respect to the first direction X, which is the transporting direction of the recording sheet 100 described above, a moving direction of the carriage 3 along the carriage shaft 5 is referred to as a second direction Y, one end side of the carriage shaft 5 is referred to as Y1, and the other end side of the carriage shaft is referred to as Y2, in the embodiment. The home position of the carriage 3 is on a Y2 side, which is one end side of the carriage shaft 5, and although not particularly illustrated, a cleaner that cleans a discharge surface to which ink droplets are discharged from the recording head 1 is provided on the Y2 side. In the embodiment, a direction intersecting both of the first direction X and the second direction Y is referred to as a third direction Z, a recording head 1 side with respect to the recording sheet 100 is referred to as Z1, and a recording sheet 100 side with respect to the recording head 1 is referred to as Z2. Although the respective directions (X, Y, and Z) have a relationship of being orthogonal to each other in the embodiment, a disposition relationship among respective configurations is not necessarily limited to a relationship of being orthogonal to each other.

In such an ink jet recording apparatus I, landing an ink over the entire area of the surface to be measured 101 of the recording sheet 100, that is, so-called printing is executed by transporting the recording sheet 100 in the first direction X with respect to the recording head 1 and discharging ink droplets from nozzles of the recording head 1 while moving the carriage 3 in the second direction Y with respect to the recording sheet 100.

In addition, a color measuring unit 10 that performs color measurement on the surface to be measured 101 of the recording sheet 100 without coming into contact the recording sheet is provided in the ink jet recording apparatus I. In the embodiment, the color measuring unit 10 is mounted on the carriage 3 with the recording head 1. For this reason, color measurement can be performed over the entire area of the surface to be measured 101 of the recording sheet 100 by transporting the recording sheet 100 in the first direction X with respect to the carriage 3 and measuring colors by means of the color measuring unit 10 while moving the carriage 3 in the second direction Y with respect to the recording sheet 100.

Such a color measuring unit 10 includes a light projecting unit 20 and a light receiving unit 30 as illustrated in FIG. 3. Light emitted from the light projecting unit 20 is reflected by the surface to be measured 101 of the recording sheet 100 and the light receiving unit 30 receives the reflected light. The chromaticity of the surface to be measured 101 is analyzed and measured based on a signal output from the light receiving unit 30.

The light projecting unit 20 includes a light source 21 that emits light and an optical system for a light source 22 configured of a plurality of lenses (only one is illustrated).

The light source 21 emits light distributed over at least a wavelength region, which is a target to be measured, and it is preferable that the distribution of light intensity with respect to wavelength be uniform although not particularly limited. An example of such a light source 21 includes a white light emitting diode (LED).

The optical system for a light source 22 includes a collimating lens that emits the light from the light source 21 as a substantially parallel light flux, and the optical system for a light source 22 emits the light emitted from the light source 21 as parallel light.

In addition, in the embodiment, the light projecting unit 20 is disposed such that the central axis of light flux of the emitted parallel light tilts at 45 degrees toward the light receiving unit 30 with respect to the third direction Z. The light projecting unit 20 itself or the optical axis of the optical system for a light source 22 may be tilted at 45 degrees with respect to the third direction Z, or parallel light emitted in the third direction Z may be tilted at 45 degrees with respect to the third direction Z by means of a prism or a reflector.

The detailed configuration of the light projecting unit 20 is not particularly limited insofar as the central axis of light flux emitted to the surface to be measured 101 is at 45 degrees with respect to a normal line of the surface to be measured 101. The optical system for a light source 22 can include optical elements such as a lens, a prism, and a reflecting surface.

The light receiving unit 30 includes an optical system for light receiving 31 configured of a plurality of lenses and filters and a light receiving element 32.

The optical system for light receiving 31 includes a wavelength changeable interference filter, and the wavelength changeable interference filter separates only light having a predetermined wavelength among light beams reflected by the surface to be measured 101 and causes the light receiving element 32 to receive the separated light beams.

An optical axis of the optical system for light receiving 31 matches a normal line direction of the surface to be measured 101. The light receiving unit 30 itself or the optical axis of the optical system for light receiving 31 may be configured so as to match the normal line direction of the surface to be measured 101, and the detailed configuration of the light receiving unit 30 is not particularly limited insofar as the light reflected from the surface to be measured 101 in the normal line direction is incident to the light receiving element 32. The optical system for light receiving 31 can include optical elements such as a lens, a prism, and a reflecting surface.

The light receiving element 32 is configured of a plurality of photoelectric converting elements and generates an electric signal according to a received light amount.

Such a color measuring unit 10 is provided so as to be movable in the second direction Y. In the embodiment, the color measuring unit 10 is movable in the second direction Y by the color measuring unit 10 being mounted on the carriage 3, on which the recording head 1 is mounted. By mounting the color measuring unit 10 on the carriage 3 that moves the recording head 1 in the second direction Y as described above, a carriage for the color measuring unit 10, which moves the color measuring unit 10 in the second direction Y, is not required to be provided in addition to the carriage 3 for the recording head 1. Therefore, since the carriage for the color measuring unit 10 and a driver that drives the carriage for the color measuring unit 10 are unnecessary, the ink jet recording apparatus I can be miniaturized and costs can be reduced. Evidently, the color measuring unit 10 may be mounted on the carriage for the color measuring unit 10 instead of being provided on the carriage 3, on which the recording head 1 is mounted.

In addition, it is preferable that the color measuring unit 10 be provided on the carriage 3 on any one side of the first direction X, which is the transporting direction of the recording sheet 100, and it is suitable to provide the color measuring unit on the X1 side, which is the upstream side in the transporting direction of the recording sheet 100. Accordingly, mist generated by an ink discharged from the recording head 1 is difficult to adhere to the color measuring unit 10. Since the recording head 1 discharges ink droplets while moving in the second direction Y as described above, mist generated by an ink discharged from the recording head 1 flows into the downstream side in the moving direction, which is the second direction Y of the recording head 1. Since the recording head 1 reciprocates in the second direction Y, a large amount of mist flows out to both of the Y1 side and the Y2 side of the second direction Y of the recording head. For this reason, when the color measuring unit 10 is provided on any one side of the second direction Y of the recording head 1, the mist is likely to adhere to the color measuring unit 10. Due to the adhered mist, color measurement failure, in which color measurement is not performed normally or the cleaning of the color measuring unit 10 becomes necessary, occurs and it takes time for performing color measurement. In addition, when transporting the recording sheet 100 in the first direction X, air flow is generated from X1, which is the upstream side of the transporting direction, toward X2, which is the downstream side. For this reason, since a large amount of mist generated by an ink discharged from the recording head 1 flows out to the X2 side, which is the downstream side, it is suitable to provide the color measuring unit 10 on the upstream side of the recording head 1 in the transporting direction of the recording sheet 100, that is, the X1 side of the first direction X. By providing the color measuring unit 10 on the upstream side of the recording head 1 in the transporting direction of the recording sheet 100, that is, the X1 side of the first direction X as described above, mist is unlikely to adhere to the color measuring unit 10, color measurement failure caused by adhered mist is unlikely to occur, the cleaning of adhered mist is unnecessary or a cleaning interval is lengthened. As a result, color measurement time can be shortened.

The ink jet recording apparatus I includes a changing unit 40 (refer to FIG. 4) that changes a reflection position of the central axis of light flux of emitted from the light projecting unit 20 on the surface to be measured 101 of the recording sheet 100. In the embodiment, the changing unit 40 changes an interval between the color measuring unit 10 and the recording sheet 100 in the third direction Z, which is the normal line direction of the surface to be measured 101 of the recording sheet 100. Specifically, by moving the carriage 3, on which the color measuring unit 10 is mounted, in the third direction Z with respect to the supporting member 8, the changing unit 40 changes a reflection position where light emitted from the light projecting unit 20 is reflected on the recording sheet 100 supported by the supporting member 8. That is, since the light projecting angle of the light projecting unit 20 and the light receiving angle of the light receiving unit 30 are fixed in the embodiment, a reflection position where light emitted from the light projecting unit 20 is reflected on the surface to be measured 101 can be changed by the light projecting unit 20 and the light receiving unit 30 being brought close to and being spaced away from the surface to be measured 101.

A reflection position where light emitted from the light projecting unit 20 is reflected on the surface to be measured 101 is a position where a light ray that matches the central axis of light flux emitted from the light projecting unit 20 is reflected on the surface to be measured 101. The changing of a reflection position where light emitted from the light projecting unit 20 is reflected on the surface to be measured 101 is the changing of a position where a light ray that matches the central axis of light flux emitted from the light projecting unit 20 is reflected on the surface to be measured 101. Regardless of a position where a light ray that matches the central axis of light flux emitted from the light projecting unit 20 is reflected on the surface to be measured 101, a change in an area irradiated with light flux from the light projecting unit 20 is not included in the changing of a reflection position where light emitted from the light projecting unit 20 is reflected on the surface to be measured 101.

Hereinafter, the "reflection position of reflected light" means a position where a light ray that matches the central axis of light flux emitted from the light projecting unit 20 is reflected on the surface to be measured 101.

Figure 4:
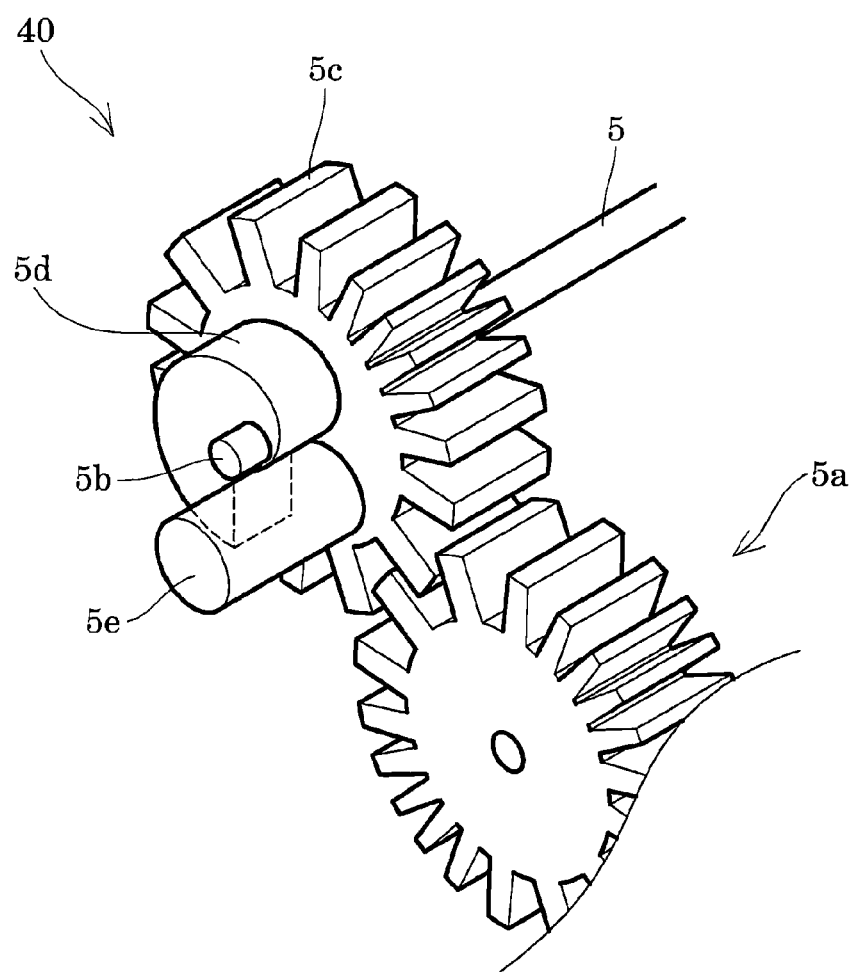
FIG. 4 is a perspective view of main portions of a changing unit of the recording apparatus according to Embodiment 1.

Herein, the changing unit 40 of the embodiment will be further described with reference to FIG. 4. FIG. 4 is a perspective view of main portions of the ink jet recording apparatus, in which the changing unit 40 is illustrated.

As illustrated in FIG. 4, the changing unit 40 is configured such that the rotation of an output shaft of an elevation-driving motor (not illustrated) is transmitted by a transmission gear train 5a to the carriage shaft 5. A composite gear that has a detection vane, which is called as a flag (not illustrated), is provided in the middle of the transmission gear train 5a, and the rotation angle of the carriage shaft 5 is controlled by detecting the flag with a rotation angle detector such as a rotary encoder. The carriage shaft 5 comes into sliding contact with a bearing unit (not illustrated) provided in the carriage 3 and guides the reciprocation of the carriage 3. On both ends of the carriage shaft, rotation shaft portions 5b are provided. At the rotation shaft portion 5b on one end side of the carriage shaft 5, a transmission gear 5c is provided so as to be integrally rotatable with the carriage shaft 5 with the central axis of the carriage shaft 5 as a rotation center. The rotation of the elevation-driving motor is transmitted to the transmission gear 5c via the transmission gear train 5a. In addition, shift cams 5d having the same shape are provided on both ends of the carriage shaft 5 so as to be integrally rotatable with the carriage shaft 5 such that reference cam positions are the same. In addition, cam followers 5e are provided below each of the shift cams 5d and are configured such that the carriage shaft 5 moves in parallel with the third direction Z due to the rotation of the carriage shaft 5 and the carriage 3 is spaced away from and is brought close to the supporting member 8 in tandem with the carriage shaft 5 that moves in parallel. The height of the carriage 3 from the supporting member 8 can be converted by the rotary encoder described above from the rotation angle of the carriage shaft 5. By adjusting the height of the carriage 3 in the third direction Z with respect to the supporting member 8, the changing unit 40 can adjust the height of the color measuring unit 10 in the third direction Z with respect to the recording sheet 100 and can change the reflection position of reflected light on the surface to be measured 101.

In addition, the changing unit 40 can also adjust an interval between the recording head 1 and the recording sheet 100, which is a so-called paper gap (PG), since the changing unit can move the carriage 3 in the third direction Z with respect to the supporting member 8. That is, the changing unit 40 that changes the position of the color measuring unit 10 in the third direction Z with respect to the recording sheet 100 can also serves as a unit that adjusts an interval between the recording head 1 and the recording sheet 100. Evidently, in a case where the color measuring unit 10 is mounted on the carriage for the color measuring unit 10 instead of being mounted on the carriage 3, on which the recording head 1 is mounted, a moving unit that moves the carriage 3, on which the recording head 1 is mounted, and the changing unit 40 described above may be separately provided.

Figure 5:
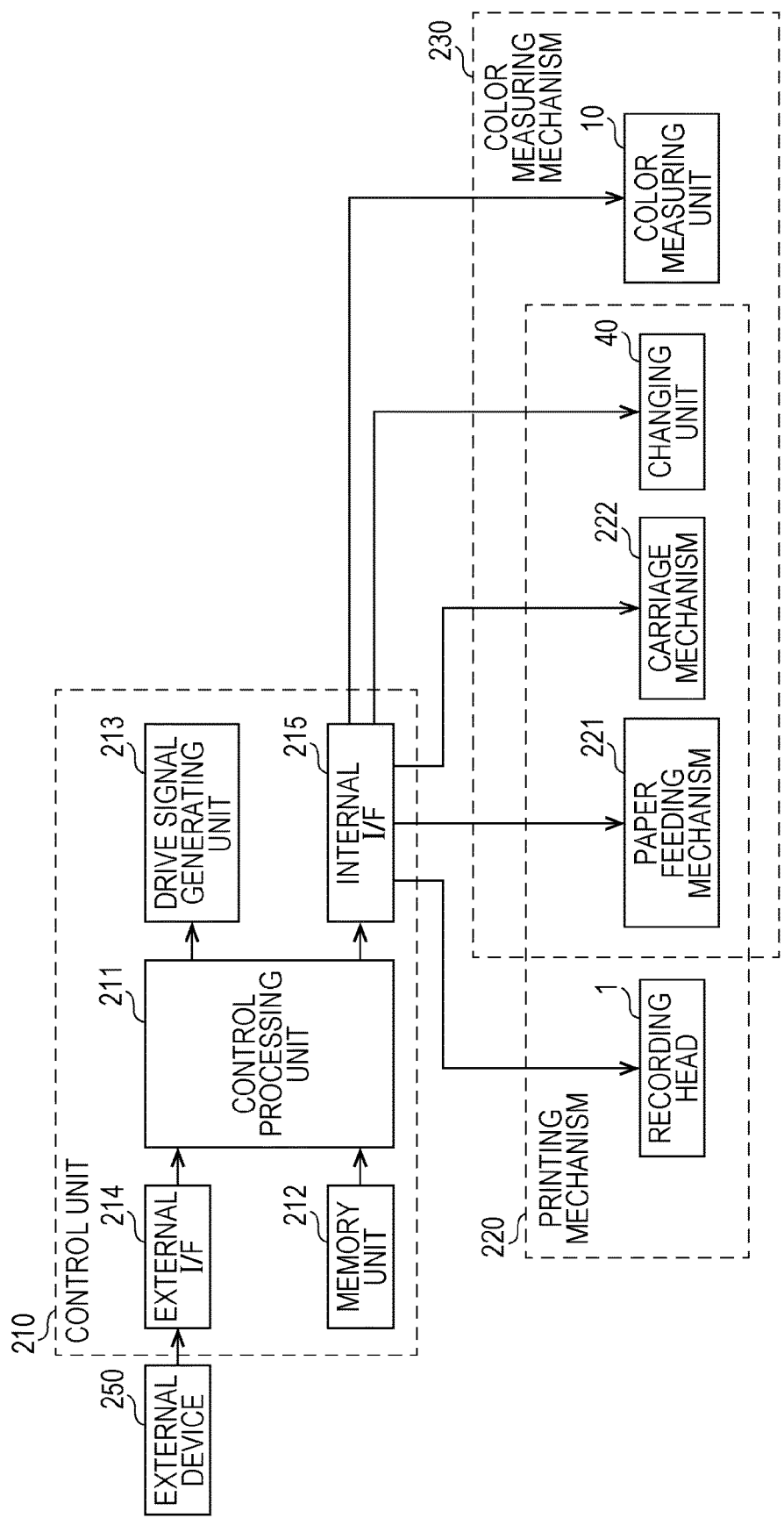
FIG. 5 is a block diagram showing an electric configuration of the recording apparatus according to Embodiment 1.

Herein, a control device 200 of such an ink jet recording apparatus I will be further described with reference to FIG. 5. FIG. 5 is a block diagram showing an electric configuration of the ink jet recording apparatus of the embodiment.

As illustrated in FIG. 5, the ink jet recording apparatus I includes a control unit 210, a printing mechanism 220, and a color measuring mechanism 230, in the embodiment.

The control unit 210 is an element that controls the entire ink jet recording apparatus I, and is provided within the control device 200 provided in the ink jet recording apparatus I in the embodiment (refer to FIG. 1).

In addition, the control unit 210 has a control processing unit 211 that is configured so as to include a CPU, a memory unit 212, a drive signal generating unit 213, an external interface (I/F) 214, and an internal I/F 215. Print data (also referred to as image data) indicating an image to be printed on the recording sheet 100 is transmitted from an external device 250, such as a host computer, to the external I/F 214. The printing mechanism 220 is connected to the internal I/F 215.

The printing mechanism 220 is an element that records an image onto the recording sheet 100 under the control of the control unit 210, and includes the recording head 1, a paper feeding mechanism 221, such as the first transporter 9a, the second transporter 9b, and a motor (not illustrated) that drives the first and second transporters, a carriage mechanism 222 of the driving motor 6 and the timing belt 7, and the changing unit 40.

The memory unit 212 includes a ROM that records control programs and a RAM that temporarily records various types of data necessary for printing an image. The control processing unit 211 comprehensively controls each element of the ink jet recording apparatus I by executing control programs recorded in the memory unit 212. In addition, as will be described in detail later, the control processing unit 211 generates color conversion information for color-converting print data transmitted to the external I/F 214 from the external device 250 based on a color measurement value obtained by the color measuring unit 10 measuring the colors of a patch (not illustrated) formed on the surface to be measured 101 of the recording sheet 100, and color-converts the print data based on the color conversion information.

The control processing unit 211 converts the color-converted print data to a head control signal instructing each nozzle to perform ejection/non-ejection of ink droplets from each of the nozzles of the recording head 1, such as a clock signal CLK, a latch signal LAT, a change signal CH, a pixel data SI, and setting data SP, based on the color conversion information, and transmits the converted signal to the recording head 1 via the internal I/F 215. The drive signal generating unit 213 generates a drive signal (COM) and transmits the signal to the recording head 1 via the internal I/F 215. That is, head control data and ejection data such as a drive signal are transmitted to the recording head 1 via the internal I/F 215, which is a transmitting unit.

In addition, the control processing unit 211 generates a movement control signal for the paper feeding mechanism 221 and the carriage mechanism 222 from the color-converted print data based on the color conversion information, and transmits the signal to the paper feeding mechanism 221 and the carriage mechanism 222 via the internal I/F 215, controlling the paper feeding mechanism 221 and the carriage mechanism 222.

The control processing unit 211 generates a paper gap control signal from data related to a paper gap, which is received from the external device 250 via the external I/F 214, and transmits the signal to the changing unit 40 via the internal I/F 215, controlling the changing unit 40 so as to adjust a paper gap.

The color measuring mechanism 230 is an element that performs color measurement on the surface to be measured 101 of the recording sheet 100 under the control of the control processing unit 211, and has the color measuring unit 10, the paper feeding mechanism 221, such as the first transporter 9a, the second transporter 9b, and the motor (not illustrated) that drives the first and second transporters, the carriage mechanism 222 of the driving motor 6 and the timing belt 7, and the changing unit 40.

The control processing unit 211 controls the paper feeding mechanism 221 and the carriage mechanism 222, and disposes the color measuring unit 10 mounted on the carriage 3 at a desired position in the first direction X and the second direction Y on the surface to be measured 101 of the recording sheet 100.

In addition, the control processing unit 211 controls the color measuring unit 10 to cause light to be emitted from the light projecting unit 20 and to cause the light receiving unit 30 to receive light reflected at the desired position on the surface to be measured 101.

The control processing unit 211 controls the changing unit 40 such that a reflection position of light, which matches the central axis of light flux emitted from the light projecting unit 20, on the surface to be measured 101 is changed while performing color measurement by means of the color measuring unit 10.

Figure 6:
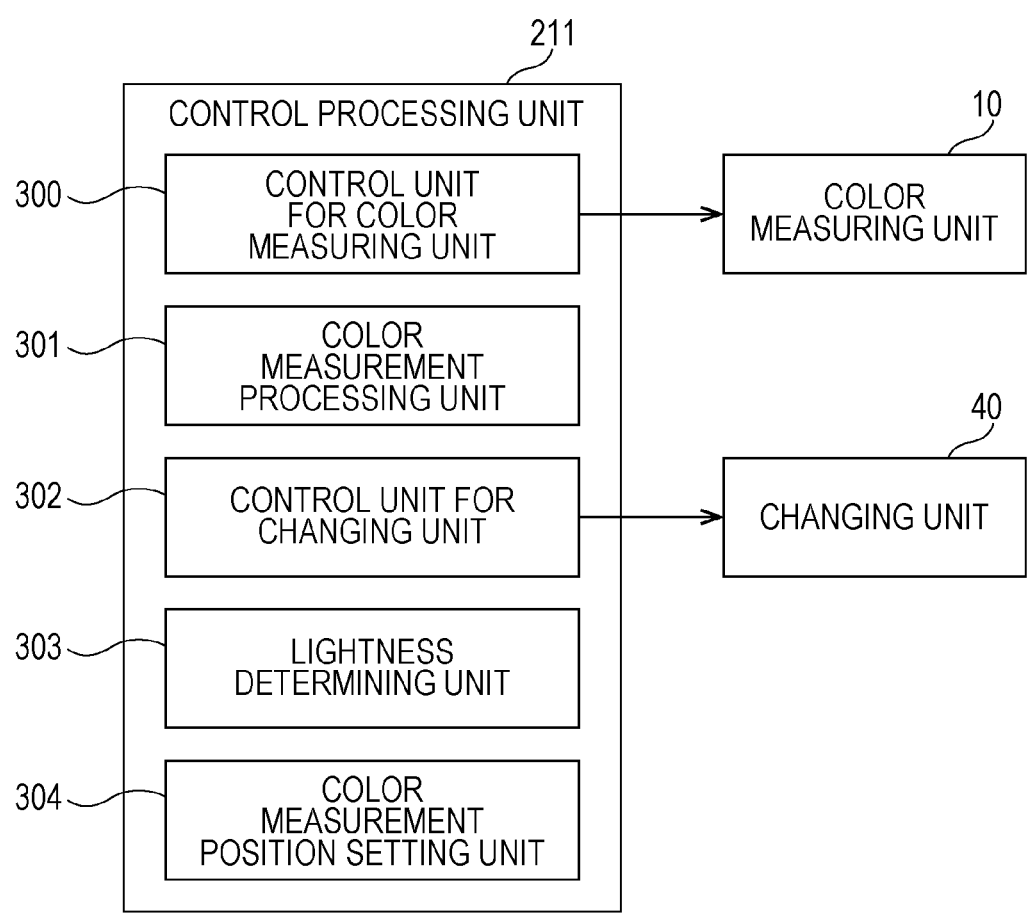
FIG. 6 is a block diagram showing function realizing units of a control processing unit according to Embodiment 1.

Herein, specific function realizing units of the control processing unit 211, which perform color measurement, will be further described with reference to FIG. 6. FIG. 6 is a block diagram showing the function realizing units of the control processing unit 211.

As illustrated in FIG. 6, the control processing unit 211 includes a control unit for a color measuring unit 300 that controls the color measuring unit 10, a color measurement processing unit 301, a control unit for a changing unit 302 that controls the changing unit 40, a lightness determining unit 303, and a color measurement position setting unit 304.

The control unit for a color measuring unit 300 controls the color measuring unit 10 to cause light to be emitted from the light projecting unit 20 and to cause the light receiving unit 30 to receive light reflected by the surface to be measured 101.

The color measurement processing unit 301 quantifies colors under a color system from an electric signal received from the color measuring unit 10. In the embodiment, the color measurement processing unit 301 quantifies colors, for example, under the L*a*b* color system.

The control unit for a changing unit 302 controls the changing unit 40 to change the reflection position of reflected light on the surface to be measured 101 of the recording sheet 100. In the embodiment, the changing unit 40 described above moves the carriage 3, on which the color measuring unit 10 is mounted, in the third direction Z with respect to the supporting member 8, and changes the reflection position of reflected light on the recording sheet 100 supported by the supporting member 8.

In such a control processing unit 211, by the control unit for a color measuring unit 300 and the control unit for a changing unit 302 controlling the color measuring unit 10 and the changing unit 40, colors are measured a plurality of times at different reflection positions of reflected light beams on the surface to be measured 101 and color measurement results for each time of color measurement are quantified as color measurement data under the color system. Color measurement data is associated with reflection position data indicating a reflection position of reflected light on the surface to be measured 101, which is changed by the changing unit 40, and is recorded in the memory unit 212. In the embodiment, a value indicating the height of the carriage 3 (the height of the color measuring unit 10) from a reference position in the third direction Z is set as reflection position data, and reflection position data at the time of color measurement (distance from the reference position to the carriage 3 (color measuring unit 10) in the third direction Z at the time of color measurement) is associated with color measurement data and is recorded in the memory unit 212.

Since the height of the carriage 3 in the third direction Z is changed by the changing unit 40 moving the carriage shaft 5, reflection position data may not be the height of the carriage 3 as described above and may be the height of the carriage shaft 5 (distance from the reference position to the carriage shaft 5 in the third direction Z). In addition, the height of the carriage 3 from the reference position in the third direction Z may be the height of a light receiving surface of the light receiving element 32 in the light receiving unit 30 of the color measuring unit 10 mounted on the carriage 3 (distance from the reference position to the light receiving surface in the third direction Z) or may be the height of an ejection surface of the recording head 1 (distance from the reference position to the ejection surface in the third direction Z). In addition, the height of the carriage 3 from the reference position in the third direction Z can be converted from the rotation angle of the carriage shaft 5 from the rotation angle detector (not illustrated) provided in the changing unit 40. Evidently, a rotation angle may be directly used as reflection position data indicating the height of the carriage 3 without calculating the height of the carriage 3 in the third direction Z from the rotation angle of the carriage shaft 5. That is, reflection position data is not particularly limited insofar as reflection position data is data that can identify the reflection position of reflected light matching the central axis of light flux emitted from the light projecting unit 20, which is changed by the changing unit 40, on the surface to be measured 101 of the recording sheet 100.

Reference that defines the height of the carriage 3, which is reflection position data, may be one point within an area where the carriage shaft 5 is movable in the third direction Z, for example, a lowermost end on a Z2 side, an uppermost end on a Z1 side, and the center, may be one point within an area where the carriage shaft 5 is rotatable, for example, a rotation start end, a rotation termination end, and a rotation center, or may be a portion that does not move relatively when the carriage 3 and the carriage shaft 5 are moved, for example, a part of the apparatus main body 4, an outer surface of the supporting member 8, and the surface to be measured 101.

In addition, color measurement at a position different from the reflection position of reflected light on the surface to be measured 101 can be performed, for example, per unit at which the resolving power of the rotation angle detector that detects the rotation angle of the carriage shaft 5 of the changing unit 40 is minimum.

The lightness determining unit 303 determines color measurement data indicating the highest lightness of reflected light obtained by diffuse reflection, from results obtained by the color measuring unit 10 measuring colors. For example, in a case where color measurement data is quantified under the L*a*b* color system, color measurement data indicating the highest L* value is selected. Accordingly, color measurement data indicating the highest lightness can be selected.

Herein, light emitted from the light projecting unit 20 is diffuse-reflected by the surface to be measured 101 and the reflected light obtained by diffuse reflection is received by the light receiving unit 30.

As for the illuminance distribution of the light flux emitted from the light projecting unit 20 onto the surface to be measured 101, the illuminance of a portion corresponding to the central axis of light flux is high, and the illuminance of a portion corresponding to the outer periphery of the light flux is low. When color measurement is performed on the surface to be measured 101 irradiated with light flux from such a light projecting unit 20, high lightness is measured at a region where light in a middle portion of the light flux from the light projecting unit 20 is reflected and low lightness is measured at a region where light which is away from the middle portion of the light flux from the light projecting unit 20 is reflected.

Figure 7:
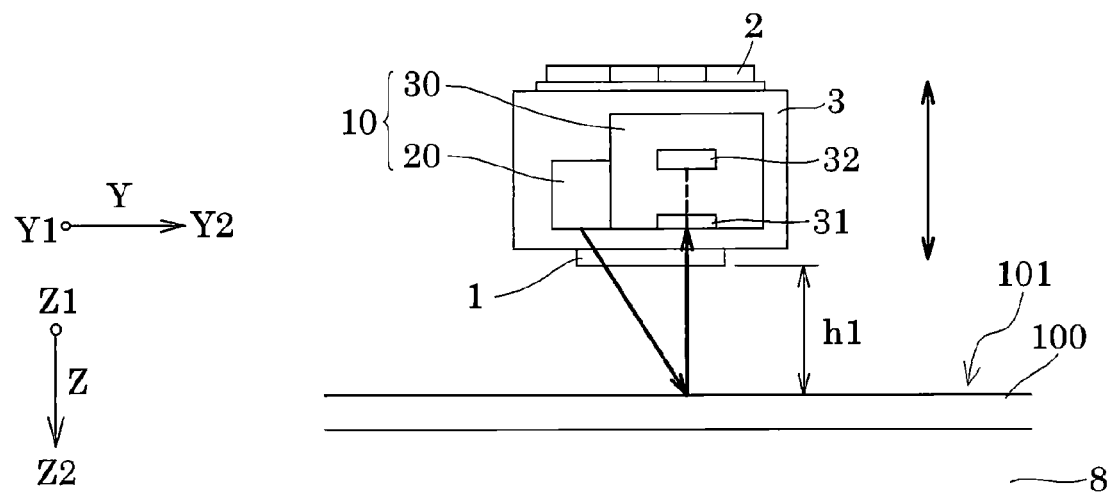
FIG. 7 is a side view of the main portions of the recording apparatus according to Embodiment 1.
Figure 8:
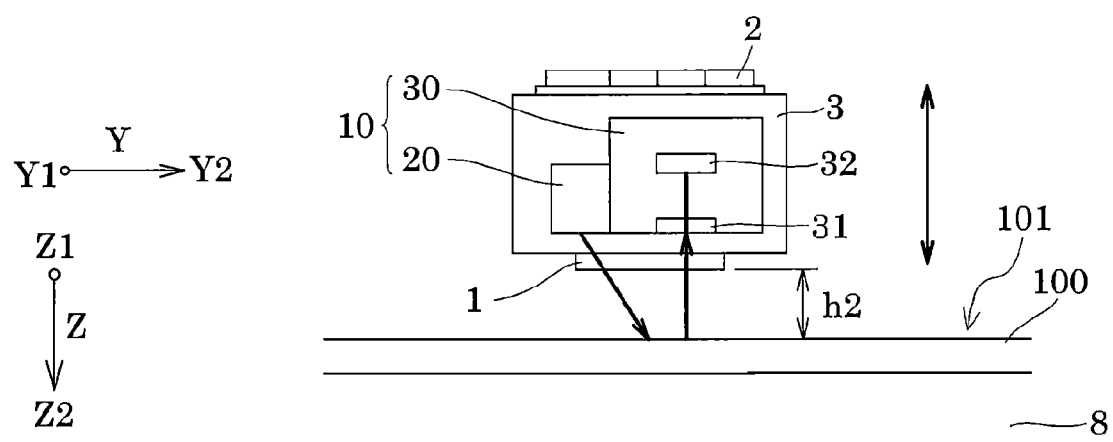
FIG. 8 is a side view of the main portions of the recording apparatus according to Embodiment 1.
Figure 9:
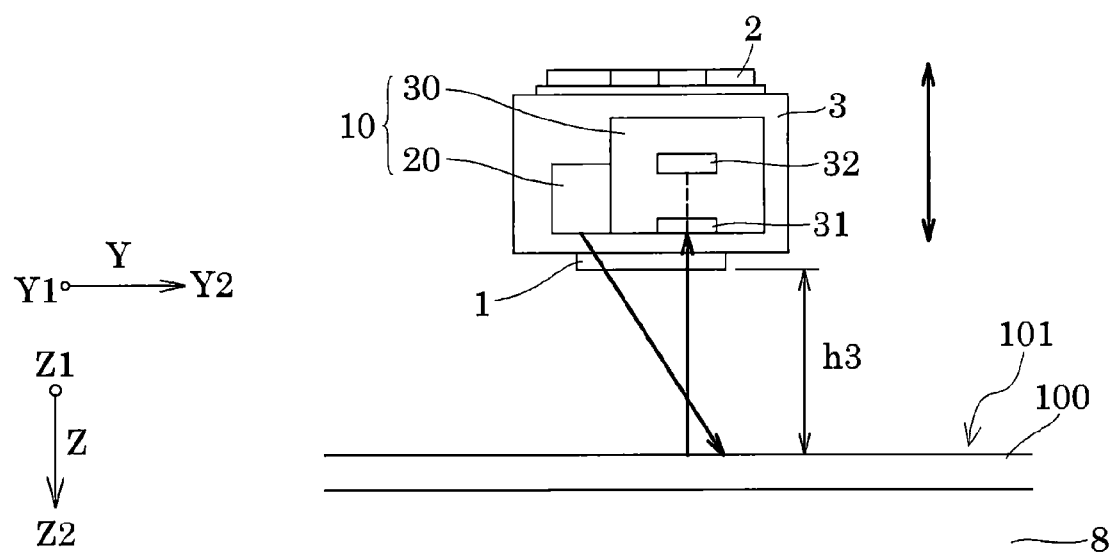
FIG. 9 is a side view of the main portions of the recording apparatus according to Embodiment 1.
Figure 10:
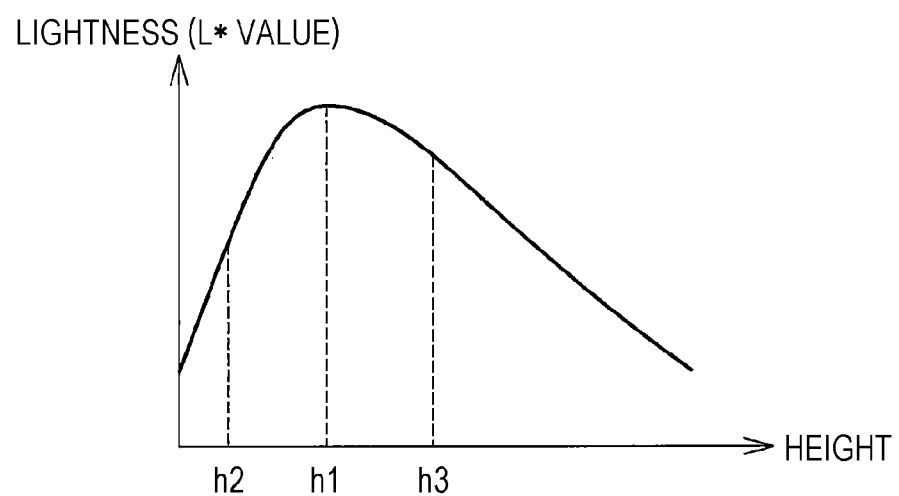
FIG. 10 is a graph showing a relationship between a reflection position and lightness according to Embodiment 1.

In examples illustrated in FIGS. 7 to 9, the height of the color measuring unit 10 from the surface to be measured 101 in the third direction Z, which is reflection position data, is a distance from the surface to be measured 101 to the ejection surface of the recording head 1 in the third direction Z. Therefore, as illustrated in FIG. 7, when the central axis of light flux from the light projecting unit 20 and the optical axis of the optical system for light receiving 31 of the light receiving unit 30 match on the surface to be measured 101 in the case of a height h1 of the color measuring unit 10 from the surface to be measured 101 in the third direction Z, lightness measured by the light receiving unit 30 is the highest as shown in FIG. 10 in the case of the height h1 since the light receiving unit 30 receives reflected light from a region having high illuminance on the surface to be measured 101. That is, lightness measured by the light receiving unit 30 is high insofar as a relative positional relationship among the light projecting unit 20, the light receiving unit 30, and the surface to be measured 101 is established such that the central axis of light flux from the light projecting unit 20 and the optical axis of the optical system for light receiving 31 of the light receiving unit 30 match.

In this regard, as illustrated in FIG. 8, since the central axis of light flux from the light projecting unit 20 and the optical axis of the optical system for light receiving 31 of the light receiving unit 30 do not match on the surface to be measured 101 and the light receiving unit 30 receives reflected light from a region having low illuminance on the surface to be measured 101 in a case where a height (distance) h2 of the color measuring unit 10 from the surface to be measured 101 is lower than the height h1, lightness measured by the light receiving unit 30 is lower in the case of the height h2 than in the case of the height h1, as shown in FIG. 10. That is, lightness measured by the light receiving unit 30 is low in a relative positional relationship among the light projecting unit 20, the light receiving unit 30, and the surface to be measured 101 is established such that the central axis of light flux from the light projecting unit 20 and the optical axis of the optical system for light receiving 31 of the light receiving unit 30 do not match.

Similarly, as illustrated in FIG. 9, since the central axis of light flux from the light projecting unit 20 and the optical axis of the optical system for light receiving 31 of the light receiving unit 30 do not match on the surface to be measured 101 and the light receiving unit 30 receives reflected light from a region having low illuminance on the surface to be measured 101 in a case where a height (distance) h3 of the color measuring unit 10 from the surface to be measured 101 is greater (longer) than the height h1, lightness measured by the light receiving unit 30 is low as shown in FIG. 10. That is, lightness measured by the light receiving unit 30 is low insofar as a relative positional relationship among the light projecting unit 20, the light receiving unit 30, and the surface to be measured 101 is established such that a light ray which matches the central axis of light flux from the light projecting unit 20 is not incident to the light receiving unit 30.

That is, since the angle between the central axis of light flux emitted from the light projecting unit 20 and the optical axis of the optical system for light receiving 31 of the light receiving unit 30 with respect to the surface to be measured 101 is fixed in the embodiment, the reflection position of reflected light of the light flux from the light projecting unit 20 on the recording sheet 100 can be changed by the light projecting unit 20 and the light receiving unit 30 being brought close to and being spaced away from the surface to be measured 101. For this reason, the lightness determining unit 303 determines if light matching the central axis of light flux emitted from the light projecting unit 20 matches the optical system for light receiving 31 of the light receiving unit 30 on the surface to be measured 101 by determining color measurement data indicating the highest lightness from a plurality of pieces of color measurement data obtained by the color measuring unit 10 measuring colors. In the embodiment, by the lightness determining unit 303 determining color measurement data indicating the highest lightness, reflection position data indicating the height of the carriage 3 from the reference, which is associated with the color measurement data, that is, practically the height h1 of the color measuring unit 10 from the surface to be measured 101 of the recording sheet 100 can be identified since the reflection position of light flux emitted from the light projecting unit 20 on the surface to be measured 101 is changed by moving the carriage 3 in the third direction Z and adjusting the heights h1 to h3 of the color measuring unit 10 from the surface to be measured 101.

The color measurement position setting unit 304 sets reflection position data, which is identified by the lightness determining unit 303 determining color measurement data indicating the highest lightness, as a color measurement position in the memory unit 212. Color measurement is performed on the recording sheet 100 at the color measurement position set by the color measurement position setting unit 304. That is, when the color measurement position is set, the color measuring unit 10 performs color measurement on a plurality of points on the surface to be measured 101 of the recording sheet 100 without changing the set color measurement position, that is, without operating the changing unit 40 and moving the carriage 3, on which the color measuring unit 10 is mounted, in the third direction Z.

Figure 11:
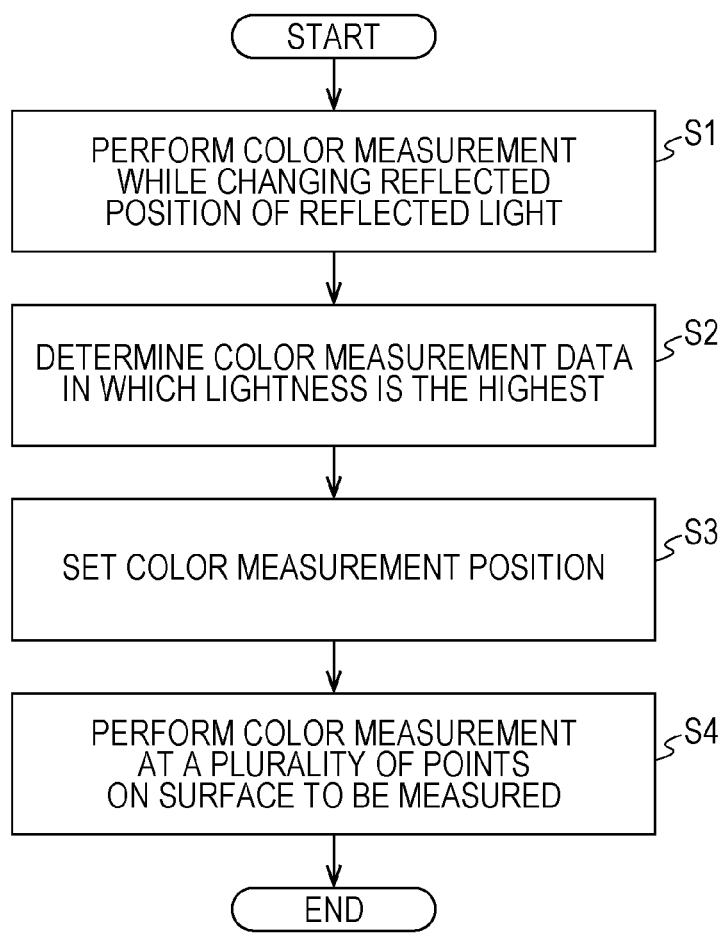
FIG. 11 is a flow chart showing a color measuring method according to Embodiment 1.

A color measuring method using such a color measuring unit 10 and such a changing unit 40 will be described with reference to FIG. 11. FIG. 11 is a flow chart showing the color measuring method.

When color measurement is initiated, a color measurement position setting mode is set first. Specifically, in Step S1, a plurality of times of color measurement are performed while the reflection position of reflected light is being changed. That is, the control unit for a color measuring unit 300 controls the color measuring unit 10 to perform color measurement while the control unit for a changing unit 302 controlling the changing unit 40 to change the height of the color measuring unit 10 from the surface to be measured 101 in the third direction Z. The color measurement processing unit 301 quantifies colors under the color system and generates color measurement data from measurement results from the color measuring unit 10. The color measurement data is associated with reflection position data and is stored in the memory unit 212. Next, in Step S2, the lightness determining unit 303 determines color measurement data indicating the highest lightness from a plurality of pieces of color measurement data. Next, in Step S3, the color measurement position setting unit 304 sets the reflection position data associated with the color measurement data identified by the lightness determining unit 303 as a color measurement position in the memory unit 212. After then, in Step S4, the control unit for a color measuring unit 300, at the color measurement position set by the color measurement position setting unit 304, performs color measurement on a plurality of points on the surface to be measured 101.

Although the setting of a color measurement position in Step S1 to Step S3 may be performed for each recording sheet 100, Steps S1 to S3 may not be performed, for example, in a case where the recording sheets 100 having the same size are used. That is, in a case where a recording sheet having the same size as the recording sheet 100, on which a color measurement position is set, is used, a shift in the optical axis of reflected light is unlikely to occur and color measurement positions are practically the same since thicknesses are the same. Therefore, when using a recording sheet having the same size, colors are measured at the same color measurement position. Thus, a step of setting a color measurement position is unnecessary and time required for color measurement can be shortened. Evidently, even in a case where a recording sheet having the same size as the recording sheet 100, on which a color measurement position is set, is used, a color measurement position may be set again by performing Steps S1 to S4. Accordingly, even when there is an error in the thickness of a recording sheet having the same size, an optimal color measurement position can be set.

As described above, in the embodiment, the changing unit 40 that changes the reflection position of light, which matches the central axis of light emitted from the light projecting unit 20, on the surface to be measured 101 of the recording sheet 100 is controlled such that a reflection position, at which lightness indicated by color measurement data obtained from reflected light received by the light receiving unit 30 is the highest, is set as a color measurement position. For this reason, since color measurement can be performed on a patch (not illustrated) printed on the surface to be measured 101 at a reflection position where lightness is the highest, color measurement accuracy can be improved. When color measurement on a patch is performed at a reflection position where lightness is low, color measurement accuracy is low, and when image data is color-converted with color conversion information that is based on a color measurement value, the reproducibility of colors deteriorates. In the embodiment, by improving color measurement accuracy, image data can be color-converted with color conversion information that is based on a highly accurate color measurement value and the reproducibility of colors can be improved.

The changing unit 40 of the embodiment changes a reflection position by changing an interval between the color measuring unit 10 and the surface to be measured 101 in the third direction Z. In particular, in the embodiment, by mounting the color measuring unit 10 on the carriage 3, on which the recording head 1 is mounted, and moving the carriage 3 in the third direction Z with respect to the surface to be measured 101, the color measuring unit 10 mounted on the carriage 3 is moved in the third direction Z with respect to the surface to be measured 101. For this reason, the changing unit 40 can also serve as a mechanism that changes an interval between the recording head 1 and the recording sheet 100, that is, a so-called paper gap. In addition, since the carriage 3, on which the recording head 1 is mounted, is provided so as to be movable in the second direction Y, a separate mechanism that moves the color measuring unit 10 in the second direction Y is unnecessary by mounting the color measuring unit 10 on the carriage 3. Therefore, a mechanism that individually moves the color measuring unit 10 and the recording head 1 in the second direction Y and the third direction Z is unnecessary. As a result, miniaturization can be achieved and costs can be reduced.

Although the recording head 1 and the color measuring unit 10 are mounted on the same carriage 3 and the changing unit 40, which moves the carriage 3 in the third direction Z, changes an interval between the recording head 1 and the recording sheet 100 and an interval between the color measuring unit 10 and the recording sheet 100 in the embodiment, the invention is not particularly limited thereto. For example, the recording head 1 and the color measuring unit 10 are mounted on the same carriage 3, and a head position changing unit that moves the recording head 1 in the third direction Z and a changing unit that moves the color measuring unit 10 in the third direction Z may be provided respectively on the carriage 3. In addition, each of the recording head 1 and the color measuring unit 10 may be mounted on different carriages.

In the embodiment, the color measuring unit 10 is provided on the X1 side, which is the upstream side of the recording head 1, in the first direction X, which is the transporting direction of the recording sheet 100. For this reason, mist is unlikely to adhere to the color measuring unit 10, color measurement failure due to adhered mist is unlikely to occur, and the cleaning of adhered mist is unnecessary or a cleaning interval is lengthened. As a result, color measurement time can be shortened.

Although the color measuring unit 10 is provided on the X1 side of the recording head 1 on the carriage 3 in the embodiment, the adhesion of mist can be suppressed by disposing the color measuring unit 10 on the X1 side of the recording head 1 even in a case where the color measuring unit 10 is not mounted on the carriage 3.

Embodiment 2

Figure 12:
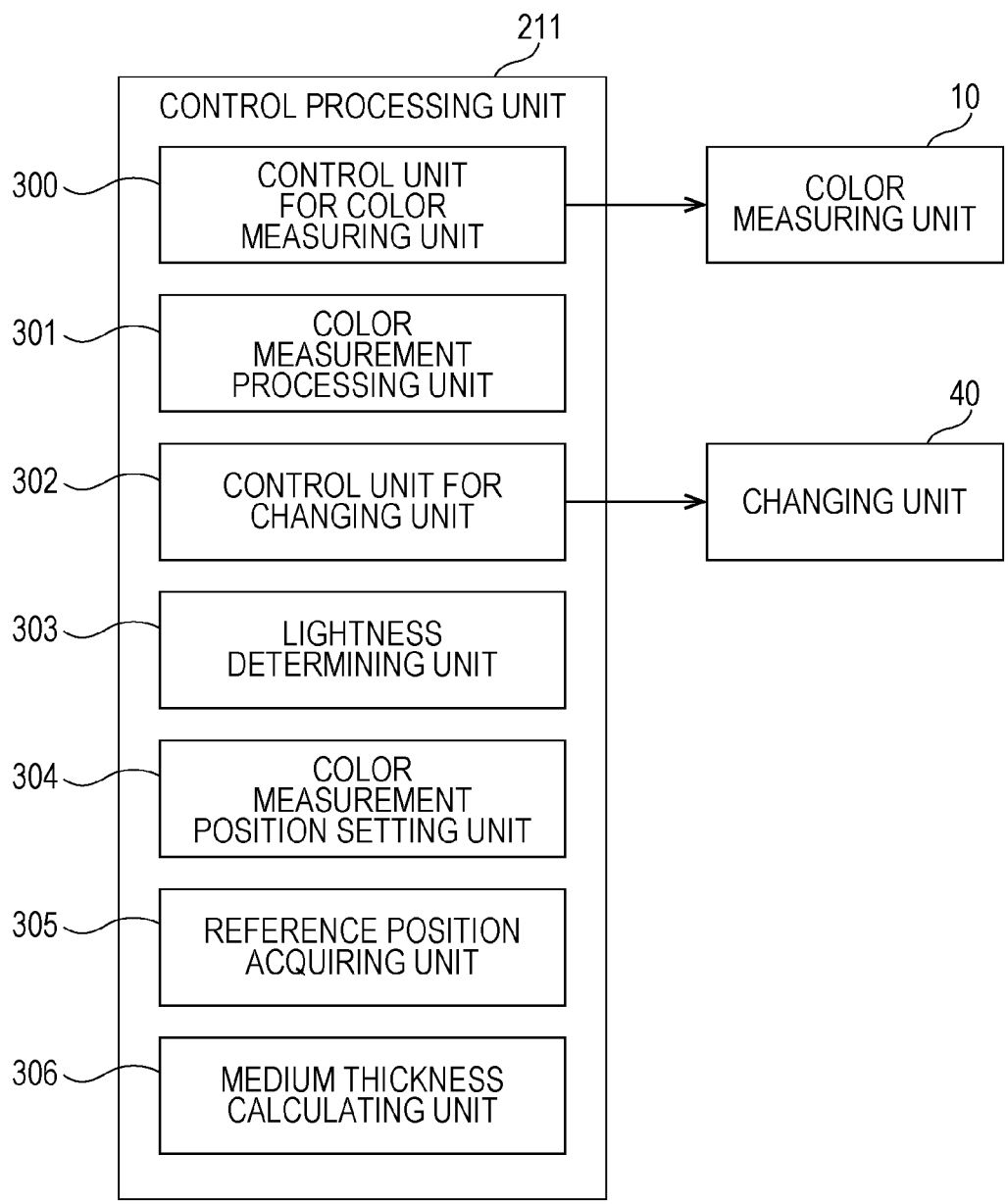
FIG. 12 is a block diagram showing function realizing units of a control processing unit according to Embodiment 2.
Figure 13:
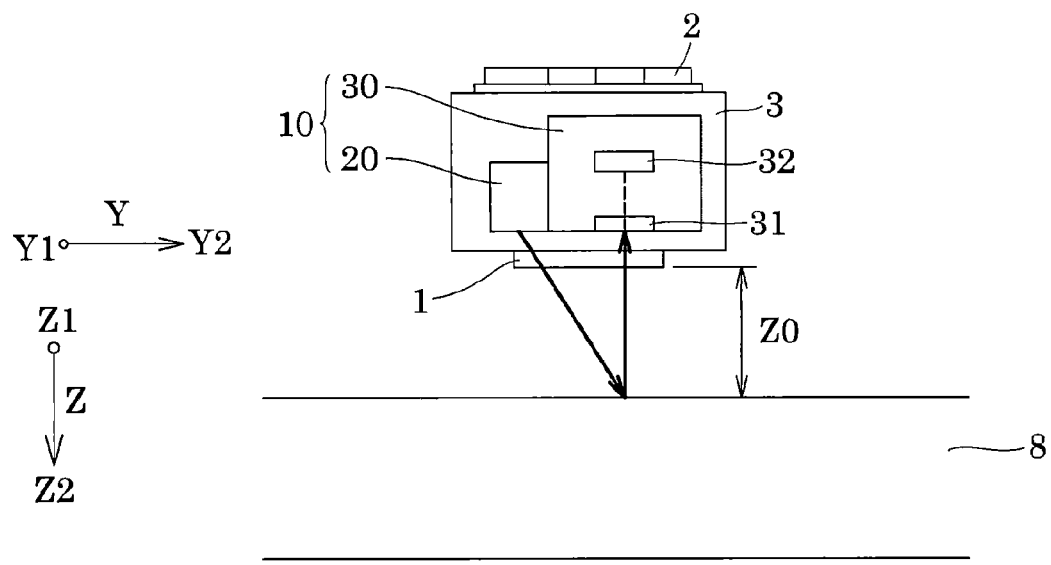
FIG. 13 is a side view of main portions of a recording apparatus according to Embodiment 2.
Figure 14:
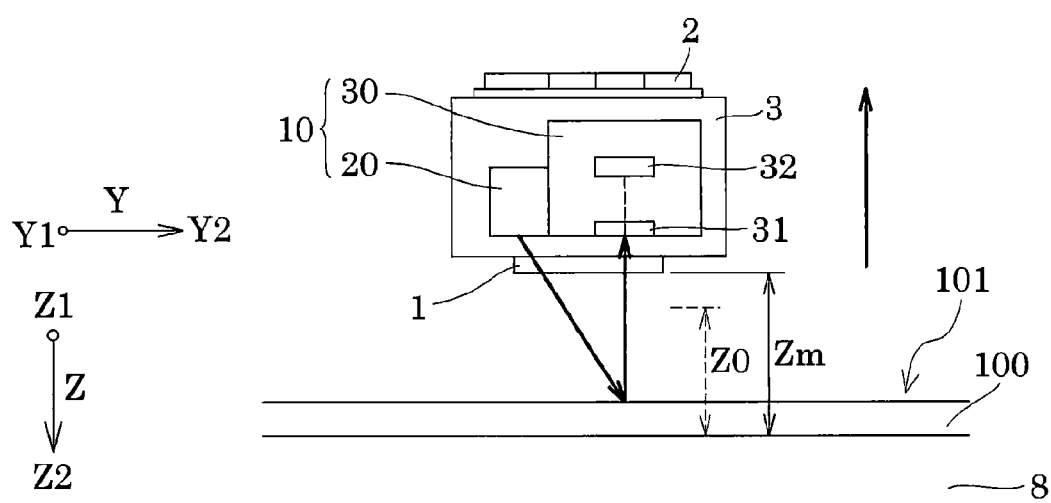
FIG. 14 is a side view of the main portions of the recording apparatus according to Embodiment 2.

FIG. 12 is a block diagram showing function realizing units of the control processing unit 211 of an ink jet recording apparatus, which is an example of a liquid ejecting apparatus according to Embodiment 2 of the invention, FIG. 13 is a side view illustrating a reference position, and FIG. 14 is a side view illustrating a color measurement position. The same members as in the embodiment described above will be assigned with the same reference signs and overlapping description will be omitted.

In the embodiment, the thickness of the recording sheet 100 is measured with the use of the color measuring unit 10 and the changing unit 40. That is, a reflection position where the lightness of light reflected on the supporting member 8, which is in a state where the recording sheet 100 is not set, is the highest is set as a reference position, and the thickness of the recording sheet 100 is calculated based on the reference position and a color measurement position where the lightness of light reflected on the recording sheet 100 is the highest.

Specifically, as shown in FIG. 12, the control processing unit 211 further includes a reference position acquiring unit 305 and a medium thickness calculating unit 306 as function realizing units.

The reference position acquiring unit 305 controls the color measuring unit 10 and the changing unit 40 by means of the control unit for a color measuring unit 300 and the control unit for a changing unit 302, and acquires reflection position data associated with color measurement data indicating the highest lightness, which is obtained from the reflected light of light flux emitted from the light projecting unit 20 on the outer surface of the supporting member 8, to which the recording sheet 100 is not transported, as a reference position.

Specifically, the reference position acquiring unit 305 causes the control unit for a color measuring unit 300 to control the color measuring unit 10, causes light emitted from the light projecting unit 20 to be reflected on the supporting member 8, and causes the light receiving unit 30 to receive the reflected light. As described above, the color measurement processing unit 301 is quantified under the color system from an electric signal received by the color measuring unit 10, and generates color measurement data.

In addition, the reference position acquiring unit 305 causes the control unit for a changing unit 302 to control the changing unit 40 and changes the reflection position of reflected light on the outer surface of the supporting member 8. In the embodiment, the changing unit 40 described above moves the carriage 3, on which the color measuring unit 10 is mounted, in the third direction Z with respect to the supporting member 8 and changes the reflection position of reflected light on the supporting member 8.

In addition, the reference position acquiring unit 305 measures colors at different reflection positions of reflected light beams on the supporting member 8 a plurality of times by causing the control unit for a color measuring unit 300 and the control unit for a changing unit 302 to control the color measuring unit 10 and the changing unit 40. Color measurement results for each time of color measurement are quantified under the color system and are generated as color measurement data. Color measurement data is associated with the reflection position of reflected light on the supporting member 8, which is changed by the changing unit 40, that is, reflection position data indicating the height of the carriage 3 from the reference position in the third direction Z in the embodiment, and is recorded in the memory unit 212.

Since the height of the carriage 3 in the third direction Z is changed by the changing unit 40 moving the carriage shaft 5, reflection position data may not indicate the height of the carriage 3 as described above and may indicate the height of the carriage shaft 5 (distance from the reference position to the carriage shaft 5 in the third direction Z). In addition, the height of the carriage 3 from the reference position in the third direction Z may indicate the height of a light receiving surface of the light receiving element 32 in the light receiving unit 30 of the color measuring unit 10 mounted on the carriage 3 (distance from the reference position to the light receiving surface in the third direction Z) or may indicate the height of the ejection surface of the recording head 1 (distance from the reference position to the ejection surface in the third direction Z). In addition, the height of the carriage 3 from the reference position in the third direction Z can be converted from the rotation angle of the carriage shaft 5 from the rotation angle detector (not illustrated) provided in the changing unit 40. Evidently, the rotation angle may be directly used as reflection position data indicating the height of the carriage 3 without calculating the height of the carriage 3 in the third direction Z from the rotation angle of the carriage shaft 5. That is, reflection position data is not particularly limited insofar as reflection position data is data that can identify the reflection position of reflected light matching the central axis of light flux emitted from the light projecting unit 20, which is changed by the changing unit 40, on the surface to be measured 101 of the recording sheet 100.

Reference that defines the height of the carriage 3, which is reflection position data, may be a lowermost end on the Z2 side, an uppermost end on the Z1 side, and the center within an area where the carriage shaft 5 is movable in the third direction Z, may be a rotation start end, a rotation termination end, and a rotation center within an area where the carriage shaft 5 is rotatable, or may be a portion that does not move relatively when the carriage 3 and the carriage shaft 5 are moved, for example, a part of the apparatus main body 4 and the outer surface of the supporting member 8. In the embodiment, a distance from the outer surface of the supporting member 8 to the ejection surface of the recording head 1 in the third direction Z, which is an indicator of the height of the color measuring unit 10 from the supporting member 8 in the third direction Z, is set as reflection position data, as illustrated in FIG. 13.

The lightness determining unit 303 determines color measurement data indicating the highest lightness of reflected light obtained by diffuse reflection, from results obtained by the color measuring unit 10 measuring colors. For example, in a case where color measurement data is quantified under the L*a*b* color system, color measurement data indicating the highest L* value is selected. Accordingly, color measurement data indicating the highest lightness can be selected.

The reference position acquiring unit 305 sets reflection position data associated with the color measurement data indicating lightness determined by the lightness determining unit 303 is the highest as a reference position in the memory unit 212. In the embodiment, as illustrated in FIG. 13, Z0, which is a height from the outer surface of the supporting member 8 to the color measuring unit 10 in the third direction Z, is set as a reference position Z0.

As in Embodiment 1 described above, the control unit for a color measuring unit 300, the control unit for a changing unit 302, and the color measurement position setting unit 304 detect a color measurement position where lightness indicated by color measurement data obtained from light reflected by the surface to be measured 101 of the recording sheet 100 disposed on the supporting member 8 is the highest, and set the color measurement position in the memory unit 212. In the embodiment, as for reflection position data to become a color measurement position, Zm, which is the height of the color measuring unit 10 from the outer surface of the supporting member 8 in the third direction Z, is set as a color measurement position Zm, as illustrated in FIG. 14.

The medium thickness calculating unit 306 calculates the thickness of the recording sheet 100 in the third direction Z based on the reference position Z0 where lightness indicated by color measurement data obtained from light reflected by the supporting member 8 is the highest, which is acquired by the reference position acquiring unit 305, and the color measurement position Zm where lightness indicated by color measurement data obtained from reflected light on the surface to be measured 101 of the recording sheet 100 is the highest, which is set by the color measurement position setting unit 304. That is, the thickness of the recording sheet 100 placed on the supporting member 8 can be calculated by subtracting the color measurement position Zm from the reference position Z0 (Zm−Z0).

Although the height Zm from the outer surface of the supporting member 8 to the color measuring unit 10 is set as a color measurement position, the displacement amount of the color measuring unit 10 from the reference position Z0 (position at the height Z0 from the supporting member 8) may be set as reflection position data associated with color measurement data obtained by causing light to be reflected by the surface to be measured 101 of the recording sheet 100 and measuring colors since the height Z0 from the supporting member 8 to the color measuring unit 10, which is at the reference position where lightness indicated by color measurement data obtained from light reflected by the supporting member 8 is the highest, does not change. Accordingly, reflection position data associated with color measurement data indicating the highest lightness of the recording sheet 100 can be directly acquired as the thickness of the recording sheet 100.

As described above, in the embodiment, the control unit 210 controls the changing unit 40 to set a distance from the position of the color measuring unit 10, at which lightness when light reflected by the outer surface of the supporting member 8 supporting a surface opposite to the surface to be measured 101 of the recording sheet 100 is received by the light receiving unit 30 is the highest, to the outer surface of the supporting member 8, as a reference position and acquires the thickness of the recording sheet 100 based on the reference position and the color measurement position on the surface to be measured 101 of the recording sheet 100. For this reason, costs can be reduced since a separate sensor that measures the thickness of the recording sheet 100 is unnecessary, and miniaturization can be achieved since a space to dispose the sensor is unnecessary. In addition, the changing unit 40 can control a paper gap, which is an interval between the recording sheet 100 and the recording head 1, with high accuracy by acquiring the thickness of the recording sheet 100. Therefore, highly accurate printing can be realized.

In addition, in the embodiment, the colors of a non-landing region where ink droplets do not land on the recording sheet 100, that is, a non-printing region may be measured to identify a paper white value, and the recording sheet 100 may be identified from the paper white value and the thickness of the recording sheet 100 described above.

There are a plurality of types of recording sheets having different materials and thicknesses according to manufacturers, which manufacture recording sheets, and use. For this reason, a recording sheet can be identified based on the thickness of the recording sheet and a paper white value measured by the color measuring unit 10. By identifying a recording sheet, an optimal print setting can be performed for the identified recording sheet. For example, by accumulating the thicknesses and the paper white values of the plurality of types of recording sheets and an optimal print setting for each recording sheet as data in advance and identifying a recording sheet from the thickness and the paper white value of the recording sheet, an optimal print setting for the identified recording sheet can be called up. In addition, for example, a paper white value and a thickness, which are measured by the color measuring unit 10 in the past, and a print setting, which is set by a user when printing the recording sheet, may be stored, and a print setting set in the past may be called up when a recording sheet that is the same as a recording sheet, of which colors are measured and which is printed in the past, in terms of a paper white value and a thickness is detected.

A recording sheet differs in terms of color reproducibility, ink absorbability, ease of occurrence of a kink due to the landing of an ink, and drying time according to a type, such as a material and a thickness. Therefore, by identifying a recording sheet, color reproducibility based on the ratio of a plurality of element colors used by the ink jet recording apparatus I, for example, cyan (C), magenta (M), yellow (Y), and black (K), the weight (poured amount) of ink droplets, paper gap (PG), the moving speed of the carriage 3, and paper feeding speed can be optimally set for the recording sheet. After being called up as a print setting, color reproducibility may be corrected based on results of color measurement by the color measuring unit 10.

An optimal print setting for the identified recording sheet 100 may not be automatically performed after the recording sheet 100 is identified. For example, when it is detected that a recording sheet identified from a thickness and a paper white value is different from a recording sheet previously used, a warning may be given to a user to set a print setting again. Due to this, printing at the same print setting on a different type of recording sheet can be suppressed and the occurrence of print failure can be suppressed.

As described above, the control unit 210 can perform an optimal print setting for the recording sheet 100 and can suppress the occurrence of print failure by identifying the recording sheet 100 based on the thickness of the recording sheet 100 acquired by the color measuring unit 10 and a paper white value, which is the color measurement results of a non-landing region where an ink is not landed on the recording sheet 100, of which colors are measured by the color measuring unit 10.

Embodiment 3

Figure 15:
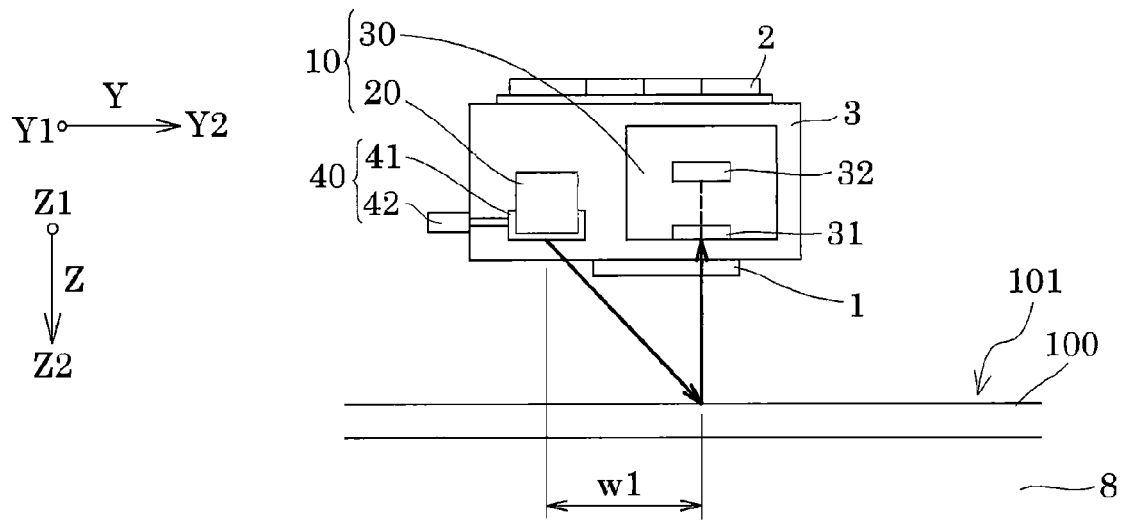
FIG. 15 is a side view of main portions of a recording apparatus according to Embodiment 3.
Figure 16:
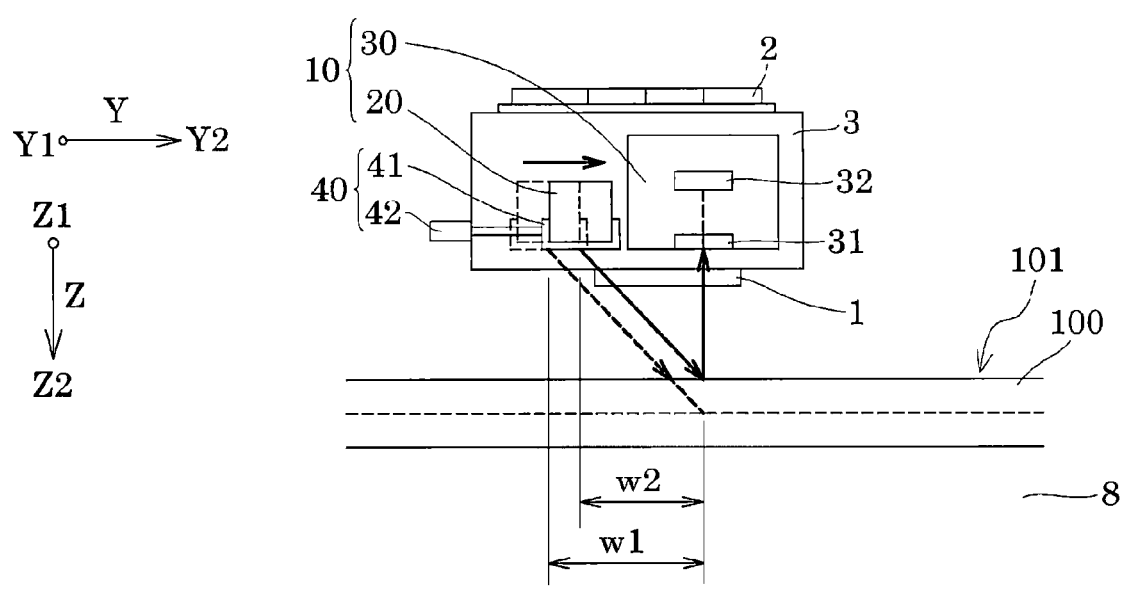
FIG. 16 is a side view of the main portions of the recording apparatus according to Embodiment 3.
Figure 17:
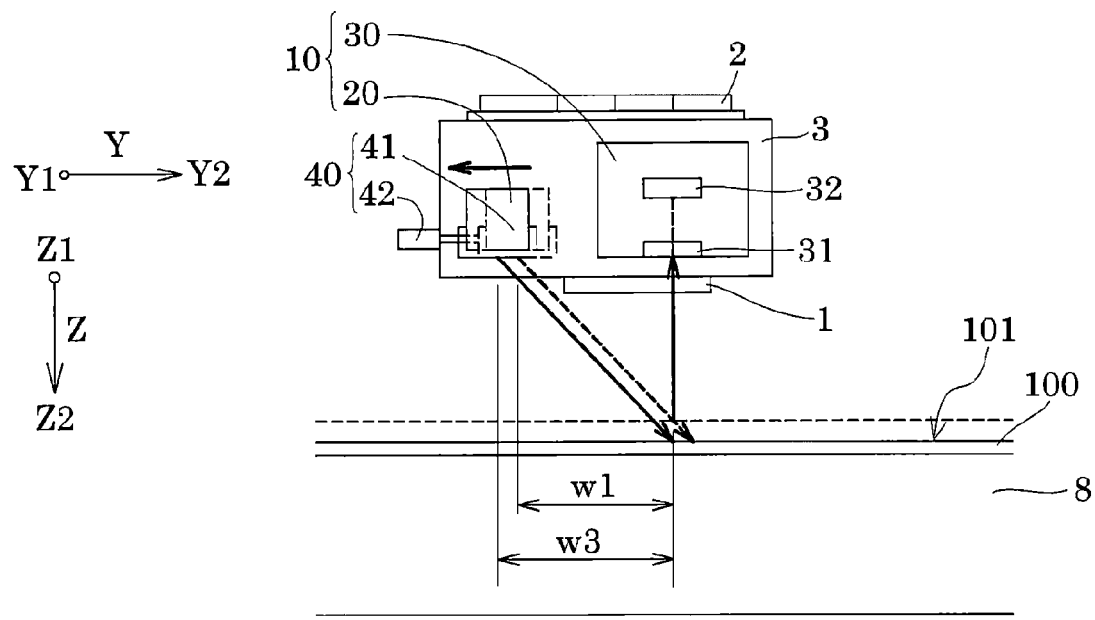
FIG. 17 is a side view of the main portions of the recording apparatus according to Embodiment 3.

FIG. 15 to FIG. 17 are side views of main portions of an ink jet recording apparatus, which is an example of a liquid ejecting apparatus according to Embodiment 3 of the invention. The same members as in the embodiment described above will be assigned with the same reference signs and overlapping description will be omitted.

As illustrated in FIG. 15, the changing unit 40 of the embodiment changes an interval between the light projecting unit 20 and the light receiving unit 30 in a plane direction parallel to the surface to be measured 101. In the embodiment, the changing unit 40 moves the light projecting unit 20 in the second direction Y with respect to the light receiving unit 30.

Specifically, the changing unit 40 includes a light projecting unit supporting unit 41 that is fixed to the carriage 3 and supports the light projecting unit 20 so as to be movable in the second direction Y and a light projecting unit driving unit 42 that drives the light projecting unit supporting unit 41.

The light projecting unit driving unit 42 is not particularly limited insofar as the light projecting unit supporting unit 41 can be moved in the second direction Y with respect to the carriage 3. For example, a motor and an electromagnet can be used as the light projecting unit driving unit. In the embodiment, a solenoid, which causes a tip of a plunger to abut against the light projecting unit supporting unit 41 and which can move the plunger in the second direction Y, is used as the light projecting unit driving unit 42. In addition, although not particularly illustrated, a moving distance detector, such as a linear encoder that can detect the moving distance of the light projecting unit supporting unit 41 is provided in the changing unit 40.

As illustrated in FIG. 15 to FIG. 17, by such a changing unit 40 changing an interval between the light projecting unit 20 and the light receiving unit 30 in the second direction Y, the reflection position of reflected light on the surface to be measured 101 of the recording sheet 100 can be changed.

As illustrated in FIG. 15, in a case where the height of the color measuring unit 10 from the surface to be measured 101 in the third direction Z (distance from the surface to be measured 101 to the ejection surface of the recording head 1) is a reference value, the central axis of light flux from the light projecting unit 20 and the optical axis of the optical system for light receiving 31 of the light receiving unit 30 match on the surface to be measured 101 at an interval w1 between the light projecting unit 20 and the light receiving unit 30, and the light receiving unit 30 can measure color measurement data indicating the highest lightness. That is, a relative positional relationship among the light projecting unit 20, the light receiving unit 30, and the surface to be measured 101, which is illustrated in FIG. 15, is a reference relative position where the colors of the surface to be measured 101 can be accurately measured.

As illustrated in FIG. 16, since the central axis of light flux from the light projecting unit 20 and the optical axis of the optical system for light receiving 31 of the light receiving unit 30 do not match on the surface to be measured 101 at the interval w1 between the light projecting unit 20 and the light receiving unit 30 and the light receiving unit 30 receives reflected light from a region having low illuminance on the surface to be measured 101 in a case where the height (distance) of the color measuring unit 10 from the surface to be measured 101 in the third direction Z is lower (shorter) than an example illustrated in FIG. 15, lightness measured by the light receiving unit 30 is lower in an example illustrated in FIG. 16 than in the example illustrated in FIG. 15. In the embodiment, the control unit for a color measuring unit 300 controls the color measuring unit 10 to measure the colors of the surface to be measured 101 while the control unit for a changing unit 302 controlling the changing unit 40 to change an interval between the light projecting unit 20 and the light receiving unit 30 in the second direction Y. The color measurement processing unit 301 quantifies colors under the color system and generates color measurement data. The color measurement data is associated with reflection position data and is stored in the memory unit 212. In the embodiment, an interval between the light projecting unit 20 and the light receiving unit 30 in the second direction Y is reflection position data. Next, the lightness determining unit 303 determines color measurement data indicating the highest lightness from a plurality of pieces of color measurement data. In the case of the recording sheet 100 illustrated in FIG. 16, the central axis of light flux from the light projecting unit 20 and the optical axis of the optical system for light receiving 31 of the light receiving unit 30 match on the surface to be measured 101 at an interval w2, which is an interval between the light projecting unit 20 and the light receiving unit 30 and is narrower than the interval w1, and the light receiving unit 30 can measure color measurement data indicating the highest lightness.

Similarly, as illustrated in FIG. 17, since the central axis of light flux from the light projecting unit 20 and the optical axis of the optical system for light receiving 31 of the light receiving unit 30 do not match on the surface to be measured 101 at the interval w1 between the light projecting unit 20 and the light receiving unit 30 and the light receiving unit 30 receives reflected light from a region having low illuminance on the surface to be measured 101 in a case where the height (distance) of the color measuring unit 10 from the surface to be measured 101 in the third direction Z is greater (longer) than the example illustrated in FIG. 15, lightness measured by the light receiving unit 30 is lower in an example illustrated in FIG. 17 than in an example illustrated in FIG. 15. In such a case as well, color measurement data indicating the highest lightness is determined from a plurality of pieces of color measurement data while an interval between the light projecting unit 20 and the light receiving unit 30 in the second direction Y is being changed as described above. In the case of the recording sheet 100 illustrated in FIG. 17, the central axis of light flux from the light projecting unit 20 and the optical axis of the optical system for light receiving 31 of the light receiving unit 30 match on the surface to be measured 101 at an interval w3, which is an interval between the light projecting unit 20 and the light receiving unit 30 and is wider than the interval w1, and the light receiving unit 30 can measure color measurement data indicating the highest lightness.

In a case where it is determined that the lightness indicated by color measurement data at the reference interval w1 is high as illustrated in FIG. 15, a position where it is unnecessary to further move the color measuring unit 10 is a color measurement position since the height of the color measuring unit 10 from the surface to be measured 101 in the third direction Z is a reference height. However, as described above, in a case where it is determined that lightness indicated by color measurement data at an interval which is different from the reference interval w1 is high, the color measuring unit 10 can be moved from the current height from the surface to be measured 101 to the reference height as in the FIG. 16 and FIG. 17 by calculating a difference between the current height of the color measuring unit 10 from the surface to be measured 101 in the third direction Z and the reference height from displacement amounts of the light projecting unit from the reference interval w1 to the intervals w2 and w3, which are reflection position data pieces associated with color measurement data that is determined as color measurement data indicating high lightness. By setting the height of the color measuring unit 10 from the surface to be measured 101 as a reference height and changing an interval between the light projecting unit 20 and the light receiving unit 30 to the interval w1, which is a reference interval, before performing color measurement to generate color conversion information, the central axis of light flux emitted from the light projecting unit 20 can be caused to match the optical axis of the optical system for light receiving 31 of the light receiving unit 30 on the surface to be measured 101 with the color measuring unit 10 being disposed at the reference height from the surface to be measured 101 and an interval between the light projecting unit 20 and the light receiving unit 30 being changed to the interval w1, which is a reference position, also in the case of the recording sheet 100 illustrated in FIG. 16 and FIG. 17.

That is, even when there are variations in the thickness of the recording sheet 100 as illustrated in FIG. 15 to FIG. 17, the occurrence of variations in lightness can be suppressed by suppressing the occurrence of variations in measurement conditions since the central axis of light flux from the light projecting unit 20 and the optical axis of the optical system for light receiving 31 of the light receiving unit 30 can be aligned on the recording sheet 100 and color measurement can be performed at the highest lightness with the height of the color measuring unit 10 from the surface to be measured 101 in the third direction Z being the reference height, which is the same at all times, and an interval between the light projecting unit 20 and the light receiving unit 30 being the reference interval w1, which is the same at all times. As a result, highly accurate color measurement can be performed. That is, if color measurement is performed with the height of the color measuring unit 10 from the surface to be measured 101 being low, measured lightness is high compared to a case where color measurement is performed at the reference height even when an interval between the light projecting unit 20 and the light receiving unit 30 is changed so as to match the central axis of light flux emitted from the light projecting unit 20 and the optical axis of the optical system for light receiving 31 of the light receiving unit 30 on the surface to be measured 101 since the height of the color measuring unit 10 from the surface to be measured 101, which is illustrated in FIG. 16, is lower than the reference height of FIG. 15. Similarly, if color measurement is performed with the height of the color measuring unit 10 from the surface to be measured 101 being great, measured lightness is low compared to a case where color measurement is performed at the reference height even when an interval between the light projecting unit 20 and the light receiving unit 30 is changed to match the central axis of light flux emitted from the light projecting unit 20 and the optical axis of the optical system for light receiving 31 of the light receiving unit 30 on the surface to be measured 101 since the height of the color measuring unit 10 from the surface to be measured 101, which is illustrated in FIG. 17, is greater than the reference height illustrated in FIG. 15. Therefore, by calculating a difference between the current height of the color measuring unit 10 from the surface to be measured 101 and the reference height based on displacement amounts of the light projecting unit from the interval w1 to the intervals w2 and w3 and moving the color measuring unit 10 to the reference height to set an interval between the light projecting unit 20 and the light receiving unit 30 to the reference interval w1, a relative position among the light projecting unit 20, the light receiving unit 30, and the surface to be measured 101 is set at the reference position and the colors of the recording sheet 100 can be accurately measured. As a result, variations in measured lightness can be suppressed.

In the embodiment, the intervals w1 to w3 between the light projecting unit 20 and the light receiving unit 30, which are reflection position data pieces, are intervals between the center position of the optical system for a light source 22 of the light projecting unit 20 in the second direction Y and the center position of the optical system for light receiving 31 of the light receiving unit 30. Evidently, without being limited thereto, the intervals w1 to w3 may be an interval between the exterior of the light projecting unit 20 and the exterior of the light receiving unit 30, or may be an interval between reference marks. In a case where the light projecting unit is moved with any one point within a movable area of the light projecting unit supporting unit 41, which is detected by the moving distance detector, as reference, the intervals w1 to w3 may be relative moving distances from the reference.

As in the Embodiment 2 described above, in a case where the thickness of the recording sheet 100 is measured, a conversion table, in which an interval between the light projecting unit 20 and the light receiving unit 30 and the height of the color measuring unit 10 from the supporting member 8 in the third direction Z are associated with each other, may be prepared. By referring to each of the heights of the color measuring unit 10 from the supporting member 8 from an interval between the light projecting unit 20 and the light receiving unit 30, at which color measurement data indicating the highest lightness is measured on each of the outer surface of the supporting member 8 and the surface to be measured 101 of the recording sheet 100, based on the conversion table, the thickness of the recording sheet 100 may be measured from a difference between the heights.

As described above, the changing unit 40 of the embodiment changes an interval between the light projecting unit 20 and the light receiving unit 30 in a plane direction parallel to the surface to be measured 101, that is, an interval in the second direction Y, in the embodiment. Due to this, the reflection position of reflected light on the surface to be measured 101 of the recording sheet 100 can be changed.

The changing unit 40 changes the position of the light projecting unit 20 in the second direction Y with respect to the light receiving unit 30 in the embodiment. Without being particularly limited thereto, the changing unit may change the position of the light receiving unit 30 in the second direction Y with respect to the light projecting unit 20.

Embodiment 4

Figure 18:
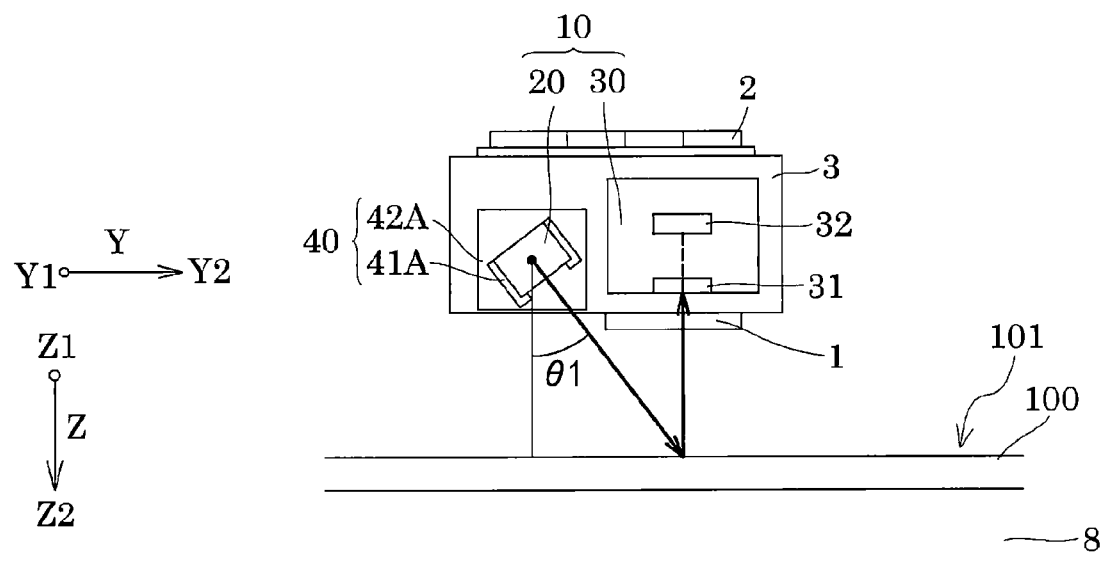
FIG. 18 is a side view of main portions of a recording apparatus according to Embodiment 4.
Figure 19:
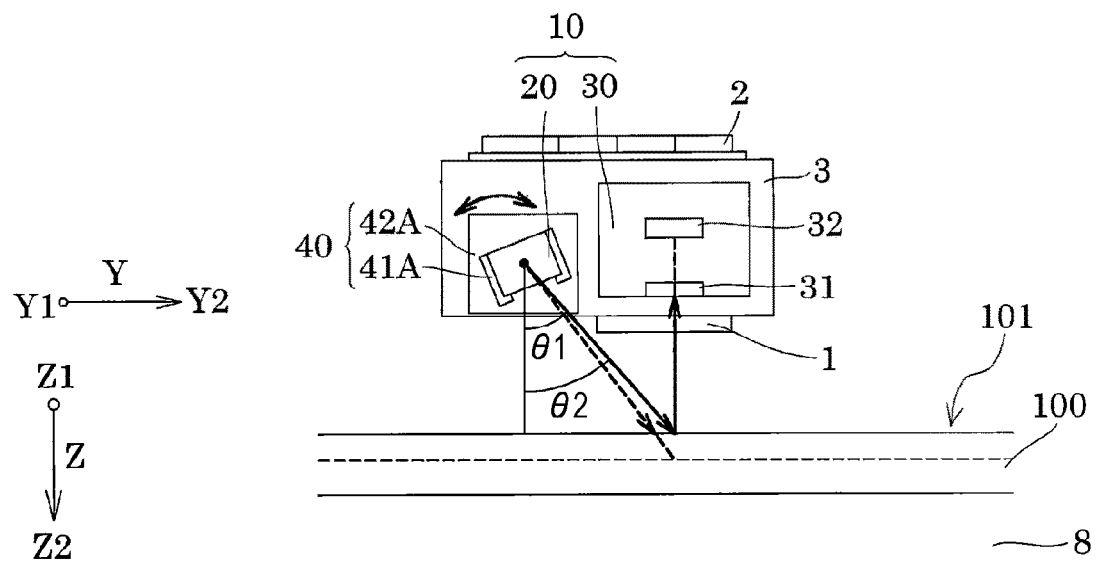
FIG. 19 is a side view of the main portions of the recording apparatus according to Embodiment 4.
Figure 20:
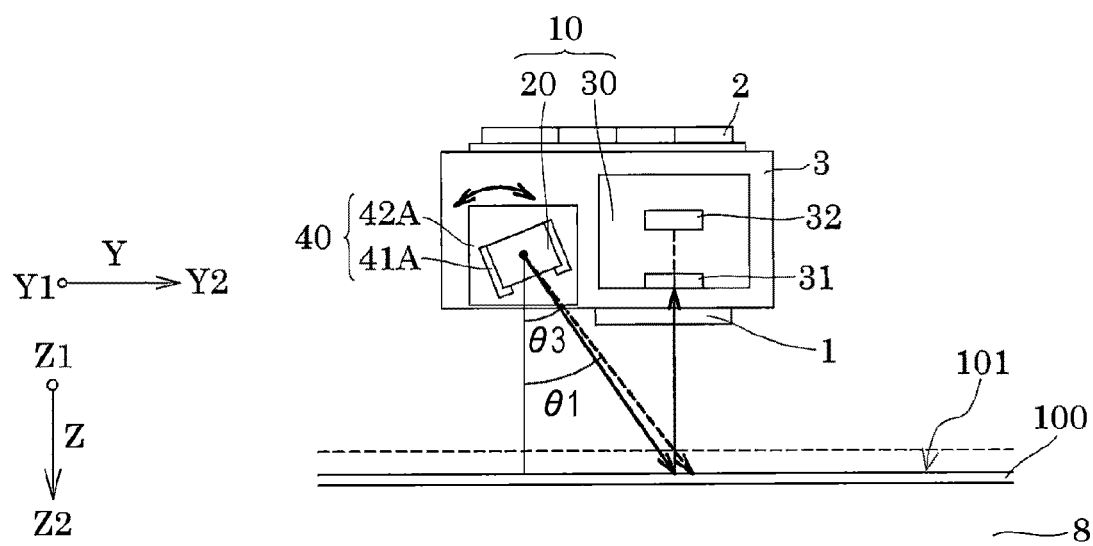
FIG. 20 is a side view of the main portions of the recording apparatus according to Embodiment 4.

FIG. 18 to FIG. 20 are side views of main portions of an ink jet recording apparatus, which is an example of a liquid ejecting apparatus according to Embodiment 4 of the invention. The same members as in the embodiment described above will be assigned with the same reference signs and overlapping description will be omitted.

As illustrated in FIG. 18, the changing unit 40 of the embodiment changes the irradiation angle of the light projecting unit 20 in directions including the third direction Z and a direction from the light projecting unit 20 to the light receiving unit 30, that is, the second direction Y in the embodiment. In other words, the changing unit changes the irradiation angle of the light projecting unit 20 with an axis parallel to the first direction X as a rotation axis.

Specifically, the changing unit 40 includes a light projecting unit supporting unit 41A that is fixed to the carriage 3 and supports the light projecting unit 20 so as to be rotatable in directions including the third direction Z and the second direction Y and a light projecting unit driving unit 42A that rotates the light projecting unit supporting unit 41A.

The light projecting unit driving unit 42A is not particularly limited insofar as the light projecting unit supporting unit 41A can be rotated. For example, a motor can be used as the light projecting unit driving unit. Although not particularly illustrated, a light projecting unit rotation angle detector, such as a rotary encoder that can detect the rotation angle of the light projecting unit supporting unit 41A is provided in the changing unit 40.

By rotating the light projecting unit 20, such a changing unit 40 changes the angle of irradiation light emitted from the light projecting unit 20 and changes the reflection position of reflected light on the surface to be measured 101 of the recording sheet 100.

As illustrated in FIG. 18, in a case where the height of the color measuring unit 10 from the surface to be measured 101 in the third direction Z (distance from the surface to be measured 101 to the color measuring unit 10) is a reference value, the central axis of light flux emitted from the light projecting unit 20 matches the optical axis of the optical system for light receiving 31 of the light receiving unit 30 on the surface to be measured 101 at an irradiation angle θ1 of the light projecting unit 20 (herein, an angle between the central axis of light flux emitted from the light projecting unit 20 and the normal line of the surface to be measured 101), and the light receiving unit 30 can measure color measurement data indicating the highest lightness. That is, a relative positional relationship among the light projecting unit 20, the light receiving unit 30, and the surface to be measured 101, which is illustrated in FIG. 18, is reference disposition where the colors of the surface to be measured 101 can be accurately measured.

As illustrated in FIG. 19, since the central axis of light flux from the light projecting unit 20 and the optical axis of the optical system for light receiving 31 of the light receiving unit 30 do not match on the surface to be measured 101 at the irradiation angle θ1 of the light projecting unit 20 and the light receiving unit 30 receives reflected light from a region having low illuminance on the surface to be measured 101 in a case where the height (distance) of the color measuring unit 10 from the surface to be measured 101 in the third direction Z is lower (shorter) than an example illustrated in FIG. 18, lightness measured by the light receiving unit 30 is low. In the embodiment, the control unit for a color measuring unit 300 controls the color measuring unit 10 to measure the colors of the surface to be measured 101 while the control unit for a changing unit 302 controlling the changing unit 40 to change an angle between the central axis of light flux emitted from the light projecting unit 20 and the normal line of the surface to be measured 101 (irradiation angle). The color measurement processing unit 301 quantifies colors under the color system and generates color measurement data. The color measurement data is associated with reflection position data and is stored in the memory unit 212. In the embodiment, an angle between the central axis of light flux emitted from the light projecting unit 20 and the normal line of the surface to be measured 101 is reflection position data. Next, the lightness determining unit 303 determines color measurement data indicating the highest lightness from a plurality of pieces of color measurement data. In the case of the recording sheet 100 illustrated in FIG. 19, the central axis of light flux from the light projecting unit 20 and the optical axis of the optical system for light receiving 31 of the light receiving unit 30 match on the surface to be measured 101 at an irradiation angle θ2 (herein, an angle between the central axis of light flux emitted from the light projecting unit 20 and the normal line of the surface to be measured 101), which is the irradiation angle of the light projecting unit 20 larger than the irradiation angle θ1, and the light receiving unit 30 can measure color measurement data indicating the highest lightness.

Similarly, as illustrated in FIG. 20, since the central axis of light flux from the light projecting unit 20 and the optical axis of the optical system for light receiving 31 of the light receiving unit 30 do not match on the surface to be measured 101 at the irradiation angle θ1 of the light projecting unit 20 and the light receiving unit 30 receives reflected light from a region having low illuminance on the surface to be measured 101 in a case where the height (distance) of the color measuring unit 10 from the surface to be measured 101 in the third direction Z is greater (longer) than an example illustrated in FIG. 18, lightness measured by the light receiving unit 30 is low. In such a case as well, color measurement data indicating the highest lightness is determined from a plurality of pieces of color measurement data while an angle between the central axis of light flux emitted from the light projecting unit 20 and the normal line of the surface to be measured 101 (irradiation angle) is being changed as described above. In the case of the recording sheet 100 illustrated in FIG. 20, the central axis of light flux from the light projecting unit 20 and the optical axis of the optical system for light receiving 31 of the light receiving unit 30 match on the surface to be measured 101 at an irradiation angle θ3, which is the irradiation angle of the light projecting unit 20 and is smaller than the irradiation angle θ1, and the light receiving unit 30 can measure color measurement data indicating the highest lightness.

In a case where lightness indicated by color measurement data at the irradiation angle θ1, which is a reference position, is high as illustrated in FIG. 18, a position where it is unnecessary to further move the color measuring unit 10 is a color measurement position since the height of the color measuring unit 10 from the surface to be measured 101 in the third direction Z is a reference height. However, the color measuring unit 10 can be moved from the current height from the surface to be measured 101 in the FIG. 19 and FIG. 20 to the reference height by calculating a difference between the current height of the color measuring unit 10 from the surface to be measured 101 in the third direction Z and the reference height from displacement amounts of the light projecting unit from the reference irradiation angle θ1 to the irradiation angles θ2 and θ3 as described above. By setting the height of the color measuring unit 10 from the surface to be measured 101 as a reference height and changing the irradiation angle of the light projecting unit 20 to the irradiation angle θ1, which is a reference irradiation angle, before performing color measurement to generate color conversion information, the central axis of light flux emitted from the light projecting unit 20 can be caused to match the optical axis of the optical system for light receiving 31 of the light receiving unit 30 on the surface to be measured 101 with the color measuring unit 10 being disposed at the reference height from the surface to be measured 101 and the irradiation angle of the light projecting unit 20 being changed to θ1, which is a reference position, also in the case of the recording sheet 100 illustrated in FIG. 19 and FIG. 20.

That is, even when there are variations in the thickness of the recording sheet 100 as illustrated in FIG. 18 to FIG. 20, the occurrence of variations in lightness can be suppressed by suppressing the occurrence of variations in measurement conditions since the central axis of light flux from the light projecting unit 20 and the optical axis of the optical system for light receiving 31 of the light receiving unit 30 can be aligned on the recording sheet 100 and color measurement can be performed at the highest lightness with the height of the color measuring unit 10 from the surface to be measured 101 in the third direction Z being the reference height, which is the same at all times, and the irradiation angle of light from the light projecting unit 20 being the reference irradiation angle θ1, which is the same at all times. As a result, highly accurate color measurement can be performed. That is, if color measurement is performed with the height of the color measuring unit 10 from the surface to be measured 101 being low, measured lightness is high compared to a case where color measurement is performed at the reference height even when the irradiation angle of the light projecting unit 20 is changed so as to match the central axis of light flux emitted from the light projecting unit 20 and the optical axis of the optical system for light receiving 31 of the light receiving unit 30 on the surface to be measured 101 since the height of the color measuring unit 10 from the surface to be measured 101, which is illustrated in FIG. 19, is lower than the reference height of FIG. 18. Similarly, if color measurement is performed with the height of the color measuring unit 10 from the surface to be measured 101 being great, measured lightness is low compared to a case where color measurement is performed at the reference height even when the irradiation angle of the light projecting unit 20 is changed so as to match the central axis of light flux emitted from the light projecting unit 20 and the optical axis of the optical system for light receiving 31 of the light receiving unit 30 on the surface to be measured 101 since the height of the color measuring unit 10 from the surface to be measured 101, which is illustrated in FIG. 20, is greater than the reference height illustrated in FIG. 18. Therefore, by calculating a difference between the current height of the color measuring unit 10 from the surface to be measured 101 and the reference height based on displacement amounts of the light projecting unit from the irradiation angle θ1 of the light projecting unit 20 to the irradiation angles θ2 and θ3 and moving the color measuring unit 10 to the reference height to set the irradiation angle of the light projecting unit 20 to the reference irradiation angle θ1, a relative position among the light projecting unit 20, the light receiving unit 30, and the surface to be measured 101 is set to a reference position and the colors of the recording sheet 100 can be accurately measured. As a result, variations in measured lightness can be suppressed.

The irradiation angles θ1 to θ3 of the light projecting unit 20, which are reflection position data pieces, are the angles of irradiation light (angle of the central axis of light flux emitted from the light projecting unit 20) with respect to the third direction Z (the normal line of the surface to be measured 101), in the embodiment. Evidently, without being limited thereto, the irradiation angles θ1 to θ3 may be angles with respect to reference, the reference being an irradiation angle, at which the central axis of light flux from the light projecting unit 20 is tilted at 45 degrees with respect to the third direction Z. In addition, although the light projecting unit 20 is rotated in the embodiment, only the light source 21 and the optical system for a light source 22 provided in the light projecting unit 20 may be rotated. Alternatively, a prism and a reflector may be provided as the optical system for a light source 22 and the prism and the reflector may be rotated.

As in the Embodiment 2 described above, in a case where the thickness of the recording sheet 100 is measured, a conversion table, in which the rotation angle of the light projecting unit 20 and the height of the color measuring unit 10 from the supporting member 8 in the third direction Z are associated with each other, may be prepared. By referring to each of the heights of the color measuring unit 10 from the supporting member 8 from the rotation angle of the light projecting unit 20, at which color measurement data indicating the highest lightness is measured on each of the outer surface of the supporting member 8 and the surface to be measured 101 of the recording sheet 100, based on the conversion table, the thickness of the recording sheet 100 may be measured from a difference between the heights.

As described above, in the embodiment, the changing unit 40 changes the irradiation angle of the light projecting unit 20 in directions including the third direction Z, which is the normal line direction of the surface to be measured 101, and the second direction Y, which is a direction from the light projecting unit 20 to the light receiving unit 30. Due to this, the reflection position of reflected light on the surface to be measured 101 of the recording sheet 100 can be changed.

Although the changing unit 40 changes the irradiation angle of the light projecting unit 20 in the embodiment, the invention is not particularly limited thereto. The changing unit may change the light receiving angle of the light receiving unit 30 (angle of the optical system for light receiving 31 of the light receiving unit 30 with respect to the normal line of the surface to be measured 101) such that light which matches the central axis of light flux from the light projecting unit 20 can be received by the light receiving unit 30.

Embodiment 5

Figure 21:
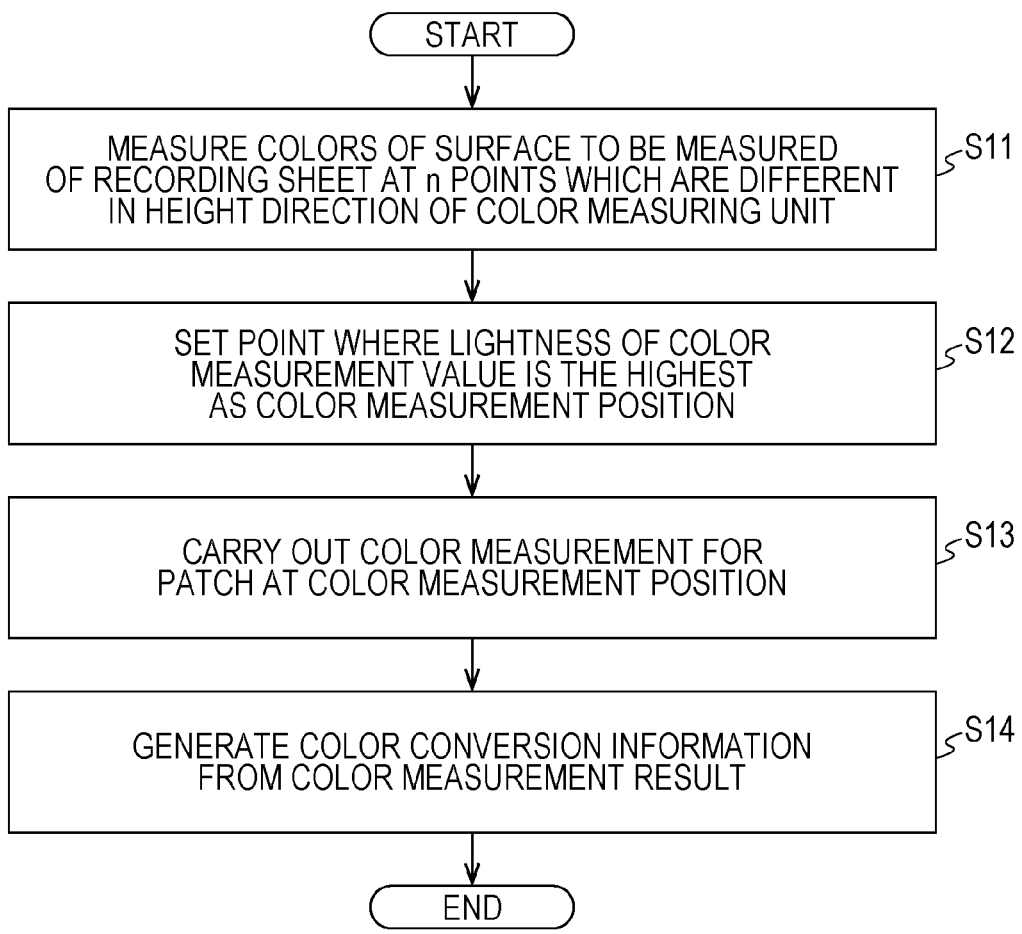
FIG. 21 is a flow chart showing a driving method according to Embodiment 5.
Figure 22:
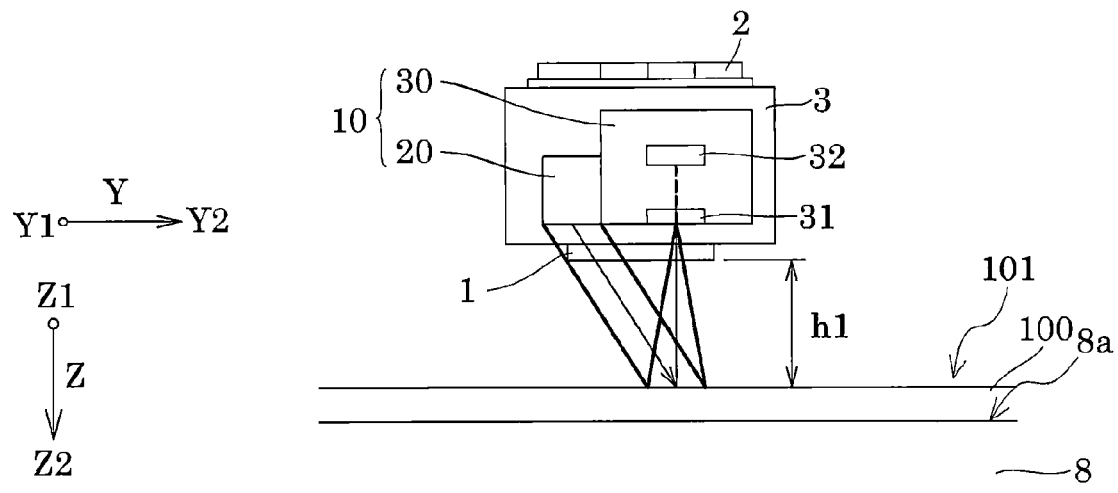
FIG. 22 is a side view of main portions of a recording apparatus according to Embodiment 5.
Figure 23:
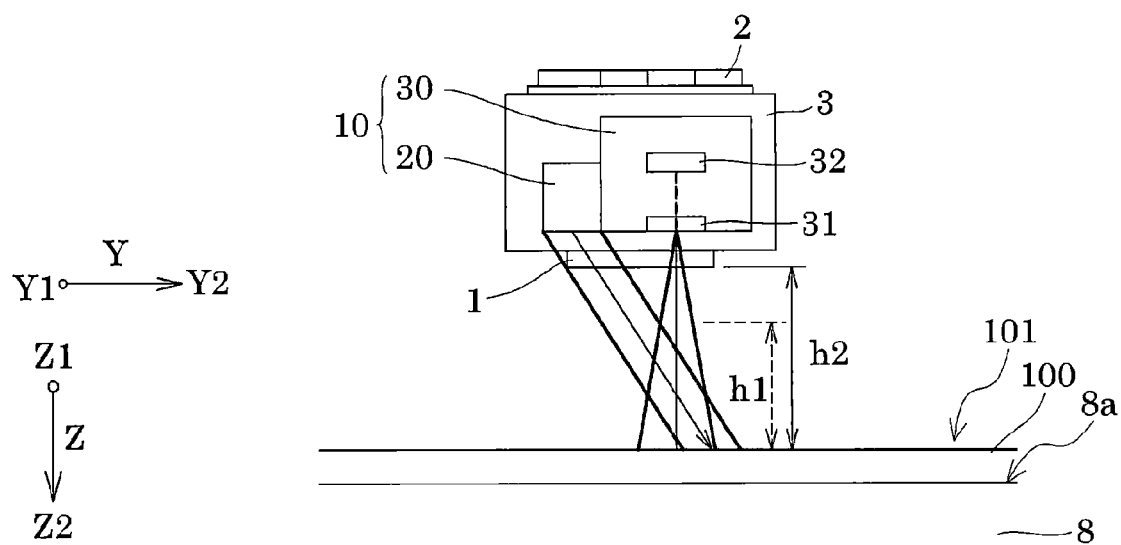
FIG. 23 is a side view of the main portions of the recording apparatus according to Embodiment 5.

FIG. 21 is a flow chart showing a driving method for an ink jet recording apparatus, which is an example of a liquid ejecting apparatus according to Embodiment 5 of the invention, FIG. 22 and FIG. 23 are side views of main portions of the ink jet recording apparatus, and FIG. 24 to FIG. 29 are views illustrating illuminance distribution. The same members as in the embodiment described above will be assigned with the same reference signs and overlapping description will be omitted.

As shown in FIG. 21, in a driving method for a liquid ejecting apparatus of the embodiment, in Step S11, the colors of the surface to be measured 101 of the recording sheet 100 is measured at n points (n 2, n is a natural number), which are different positions of the color measuring unit 10 in the third direction Z, and generated color measurement data is associated with a color measurement position (position of the color measuring unit 10 in the third direction Z) and is stored in the memory unit 212. In the embodiment, colors are measured at two points (n=2), which are different positions of the color measuring unit 10 in the third direction Z. Specifically, the colors of the surface to be measured 101 of the recording sheet 100 are measured at a first color measurement position where the height of the color measuring unit 10 from the surface to be measured 101 is the height h1 as illustrated in FIG. 22, and a second color measurement position where the height of the color measuring unit 10 from the surface to be measured 101 is the height h2 (h1≠h2) as illustrated in FIG. 23. That is, as illustrated in FIG. 22, the light projecting unit 20, the light receiving unit 30, and the recording sheet 100 are set at a first relative position (first color measurement position where the height of the color measuring unit 10 is h1), and a first color measurement value including a value indicating the lightness of the surface to be measured 101 of the recording sheet 100 is measured. Specifically, the first color measurement value (color measurement data) quantified under the color system from results measured by the color measuring unit 10 at the first color measurement position is associated with the first color measurement position and is stored in the memory unit 212. In addition, as illustrated in FIG. 23, the light projecting unit 20, the light receiving unit 30, and the recording sheet 100 are set at a second relative position (second color measurement position where the height of the color measuring unit 10 is h2), which is different from the first relative position, and a second color measurement value including a value indicating the lightness of the surface to be measured 101 of the recording sheet 100 is measured. Specifically, the second color measurement value (color measurement data) quantified under the color system from results measured by the color measuring unit 10 at the second color measurement position is associated with the second color measurement position and is stored in the memory unit 212. In the embodiment, the first relative position (first color measurement position) and the second relative position (second color measurement position) are the same when an interval between the light projecting unit 20 and the light receiving unit 30 in the second direction Y is a reference interval, and the angle between the central axis of light flux emitted from the light projecting unit 20 and the optical axis of the optical system for light receiving 31 of the light receiving unit 30 with respect to the normal line of the surface to be measured 101 is a reference angle. Information of a reference relative position is stored in the memory unit 212. The reference relative position is a position where a recording sheet 100A, of which a thickness is reference, is used, the height of a surface to be measured 101A of the color measuring unit 10 is a reference height h0, the irradiation angle of the light projecting unit 20 with respect to a normal line of the surface to be measured 101A and the angle of the optical axis of the optical system for light receiving 31 of the light receiving unit 30 with respect to the normal line of the surface to be measured are reference angles, an interval between the light receiving unit 30 and the light projecting unit 20 in the second direction Y is a reference interval, and the central axis of light flux from the light projecting unit 20 and the optical axis of the optical system for light receiving 31 of the light receiving unit 30 match on the surface to be measured 101A of the recording sheet 100A, which is reference. Accordingly, at a color measurement position for generating color conversion information, which will be described later, a relative position among the light projecting unit 20, the light receiving unit 30, and the surface to be measured 101 is set at a reference position and the colors of the recording sheet 100 can be accurately measured. As a result, variations in color measurement accuracy, which are caused by variations in the thickness of the recording sheet 100, can be suppressed.

Figure 24:
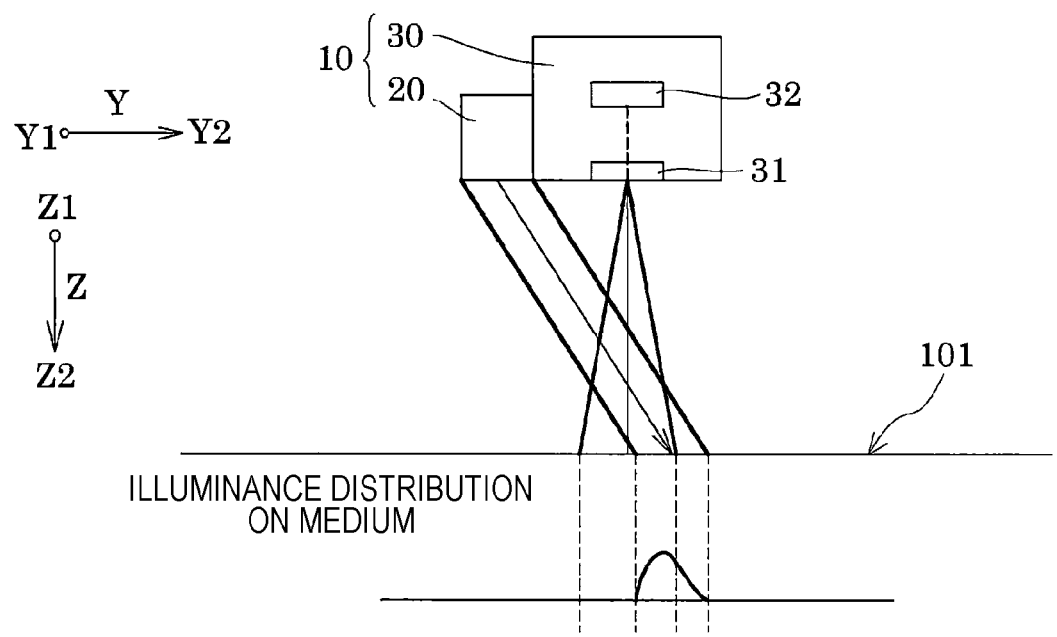
FIG. 24 is a view illustrating illuminance distribution according to Embodiment 5.
Figure 25:
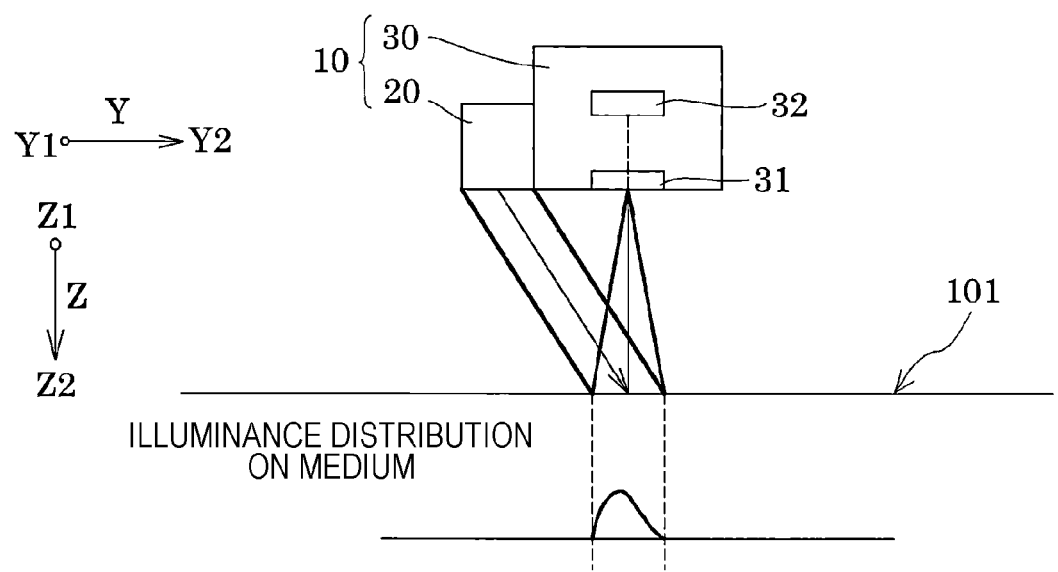
FIG. 25 is a view illustrating the illuminance distribution according to Embodiment 5.
Figure 26:
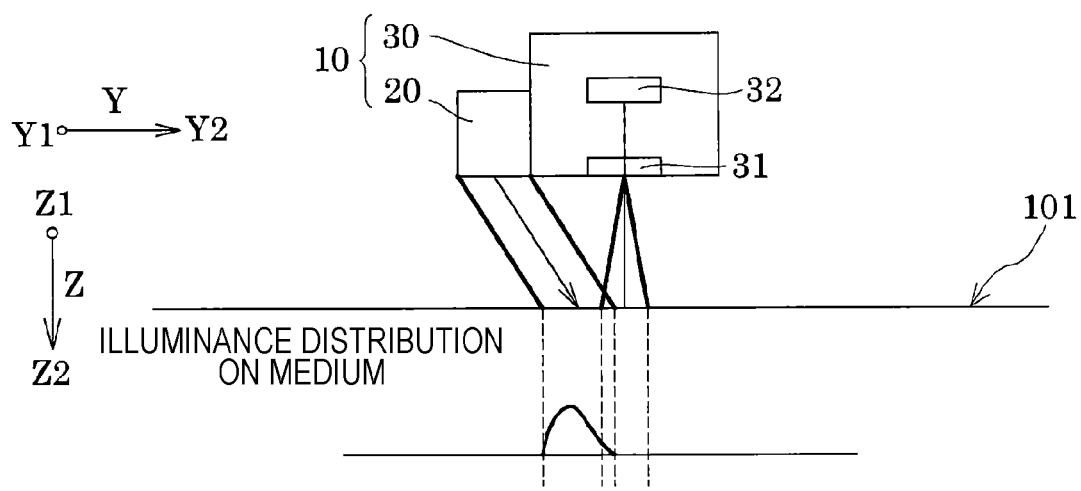
FIG. 26 is a view illustrating the illuminance distribution according to Embodiment 5.

Herein, as illustrated in FIG. 24 to FIG. 26, color measurement of a case where the illuminance distribution of light flux emitted from the light projecting unit 20 onto the surface to be measured 101, in which the illuminance of a portion corresponding to the central axis of light flux is high and a portion corresponding to the outer periphery of the light flux is low, will be described. When color measurement is performed on the surface to be measured 101 irradiated with light flux from such a light projecting unit 20, a region where light in a middle portion of the light flux from the light projecting unit 20 is reflected has high measured lightness and a region where light which is away from the middle portion of the light flux from the light projecting unit 20 is reflected has lower measured lightness. Therefore, in a case where the central axis of light flux from the light projecting unit 20 and the optical axis of the optical system for light receiving 31 of the light receiving unit 30 match on the surface to be measured 101 as illustrated in FIG. 25, the highest lightness is measured since an illumination region and a light receiving region mostly overlap each other. In a case where the central axis of light flux from the light projecting unit 20 and the optical axis of the optical system for light receiving 31 of the light receiving unit 30 do not match on the surface to be measured 101 as illustrated in FIG. 24 and FIG. 26, low lightness is measured compared to FIG. 25 since the illumination region and the light receiving region are deviated from each other.

Figure 27:
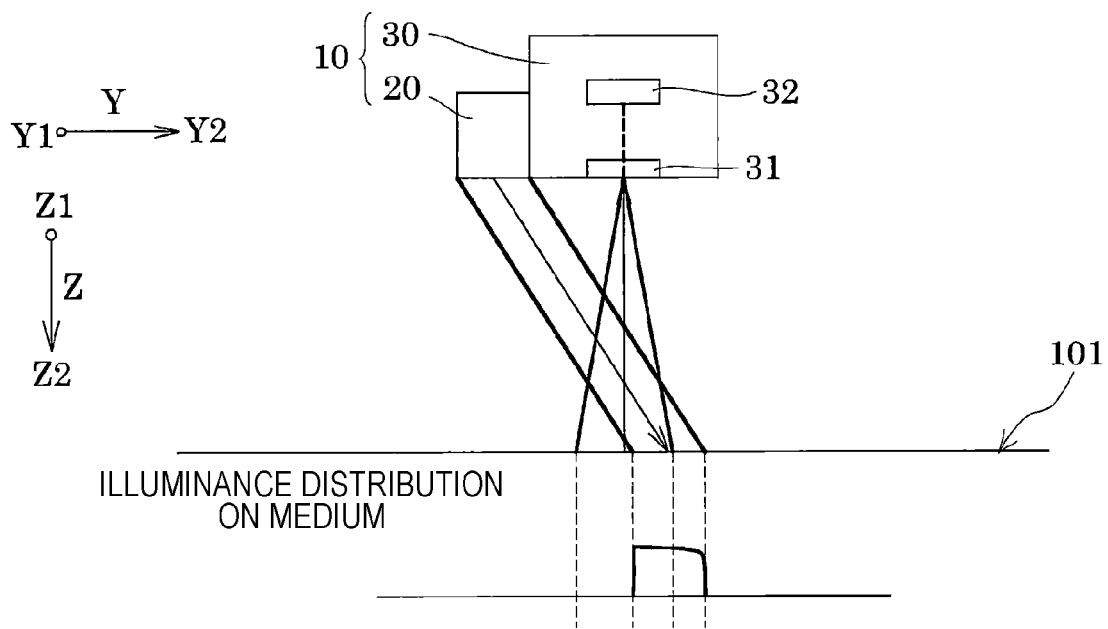
FIG. 27 is a view illustrating the illuminance distribution according to Embodiment 5.
Figure 28:
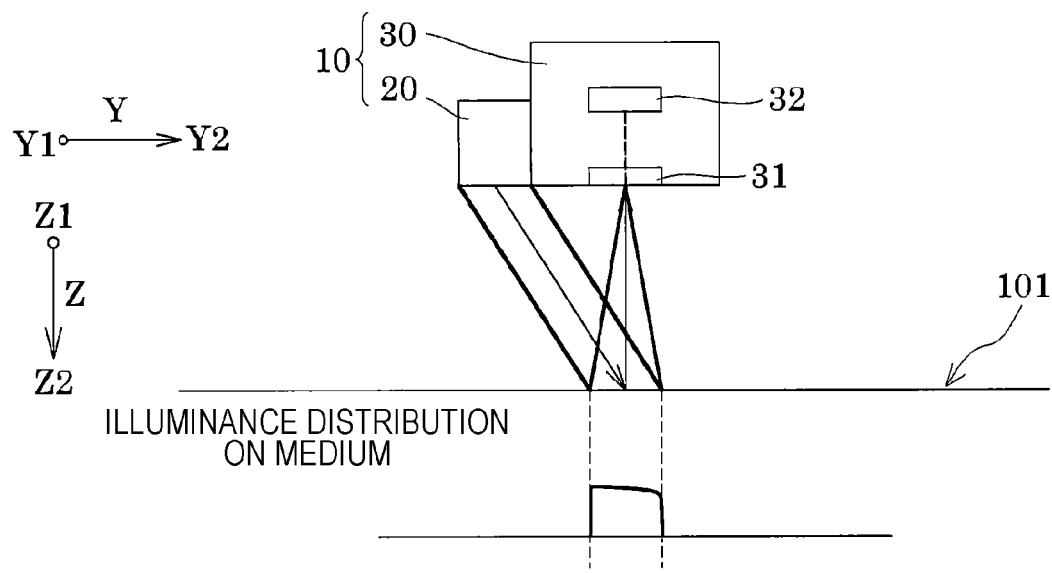
FIG. 28 is a view illustrating the illuminance distribution according to Embodiment 5.
Figure 29:
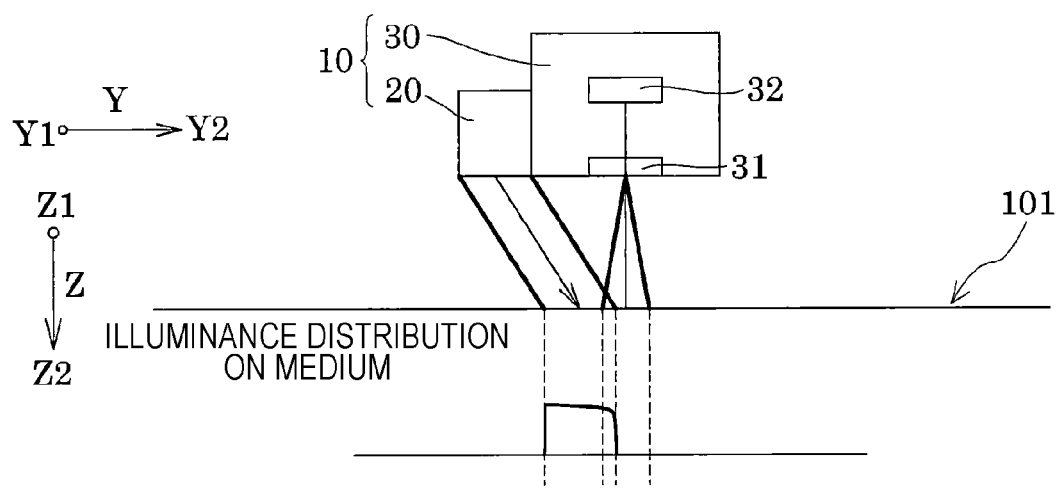
FIG. 29 is a view illustrating the illuminance distribution according to Embodiment 5.

As illustrated in FIG. 27 to FIG. 29, in a case where collimating light is emitted from the light projecting unit 20, the illuminance distribution of light flux emitted from the light projecting unit 20 on the surface to be measured 101 is substantially uniform from the central axis of light flux to the periphery of the light flux. When color measurement is performed on the surface to be measured 101, which is irradiated with light flux from such a light projecting unit 20, high lightness is measured in a case where the colors of a region including a region where the light flux from the light projecting unit 20 is reflected are measured, and low lightness is measured since the light receiving unit 30 also measures the colors of a region, which is not irradiated with the light flux, in a case where the colors of a region including only a part of the region where the light flux from the light projecting unit 20 is reflected are measured. Therefore, in a case where the central axis of light flux from the light projecting unit 20 and the optical axis of the optical system for light receiving 31 of the light receiving unit 30 match on the surface to be measured 101 as illustrated in FIG. 28, the highest lightness is measured since an illumination region and a light receiving region mostly overlap each other. In a case where the central axis of light flux from the light projecting unit 20 and the optical axis of the optical system for light receiving 31 of the light receiving unit 30 do not match on the surface to be measured 101 as illustrated in FIG. 27 and FIG. 29, low lightness is measured compared to FIG. 28 since the illumination region and the light receiving region are deviated from each other.

In a case where the central axis of light flux from the light projecting unit 20 and the optical axis of the optical system for light receiving 31 of the light receiving unit 30 match on the surface to be measured 101, the highest lightness is measured even when the light of any of light flux having illuminance distribution from the light projecting unit 20 and light flux having uniform illuminance distribution represented by collimating light is emitted.

In the embodiment, it is preferable that the light receiving area of the light receiving unit 30 from the surface to be measured 101 be the half or more of the irradiation area of the surface to be measured 101 of the recording sheet 100, which is irradiated with light flux emitted from the light projecting unit 20. That is because, when the light receiving area of the light receiving unit 30 is smaller than the half of the irradiation area of the light projecting unit 20, a lightness determination value measured at a relative position where the central axis of light flux from the light projecting unit 20 and the optical axis of the optical system for light receiving 31 of the light receiving unit 30 do not match on the surface to be measured 101 is higher than a lightness determination value measured at a relative position where the central axis and the optical axis match and thus a color measurement position for generating color conversion information cannot be accurately set since the illuminance distribution of an illuminated area on the surface to be measured 101 is high when a distance from the light projecting unit 20 to the surface to be measured 101 is short and the illuminance distribution is low when the distance is long, for example, in a case where the central axis of light flux from the light projecting unit 20 is tilted with respect to the normal line of the surface to be measured 101. The irradiation area of the surface to be measured 101, which is irradiated with light flux emitted from the light projecting unit 20, can be, for example, the area of light flux assumed from the optical system for a light source 22 of the light projecting unit 20, that is, an area obtained from an imaginary circle based on the outer diameter of the optical system for a light source 22. Similarly, the light receiving area of the light receiving unit 30 from the surface to be measured 101 can be the light receiving area of an optical system assumed from the optical system for light receiving 31 of the light receiving unit 30, that is, an area obtained from an imaginary circle based on the outer diameter of the optical system for light receiving 31.

In addition, color measurement at the first color measurement position and the second color measurement position may be performed as follows. For example, the colors of the surface to be measured 101 of the recording sheet 100, that is, the colors of the recording sheet 100 itself may be measured, or the colors of a patch, on which ink droplets discharged from the recording head are landed, that is, so-called printing is performed, on the surface to be measured 101, may be measured.

Next, in Step S12, a position where lightness indicated by a color measurement value is the highest is set as a color measurement position for generating color conversion information. That is, in the embodiment, since a lightness determination value L1 to determine lightness measured at the first color measurement position, which is the first relative position, is higher than a lightness determination value L2 to determine lightness measured at the second color measurement position, which is the second relative position (L1>L2), the first color measurement position (first relative position) is set as a color measurement position for generating color conversion information. Specifically, the first color measurement position associated with the higher lightness determination value L1 (first color measurement value) is set as a color measurement position for generating color conversion information in the memory unit 212.

Next, in Step S13, color measurement for a patch is executed at the color measurement position. Then, in Step S14, color conversion information is generated from color measurement results of the patch. After then, printing is executed with print data (image data) that is color-converted based on color conversion information. A patch can be formed by landing ink droplets discharged from the recording head 1 onto the surface to be measured 101, that is, performing so-called printing.

Color measurement accuracy can be improved by performing color measurement at the first color measurement position and the second color measurement position and performing color measurement for the patch with the first color measurement position where lightness is the highest being as the color measurement position as described above. When color measurement for a patch is performed at the second color measurement position where lightness is low, color measurement accuracy is low due to the low lightness, and when image data is color-converted with color conversion information that is based on a color measurement value, the reproducibility of colors deteriorates. In the embodiment, by improving color measurement accuracy, image data can be color-converted with color conversion information that is based on a highly accurate color measurement value and the reproducibility of colors can be improved.

Although a case where the central axis of light flux emitted from the light projecting unit 20 and the optical axis of the optical system for light receiving 31 of the light receiving unit 30 match on the surface to be measured 101 at the first relative position (first color measurement position) as illustrated in FIG. 22 is given as an example in the embodiment, the invention is not particularly limited thereto. A case where the central axis of light flux emitted from the light projecting unit 20 and the optical axis of the optical system for light receiving 31 of the light receiving unit 30 do not match on the surface to be measured 101 at the first relative position (first color measurement position) is also included in the embodiment. That is, a distance between the central axis of light flux emitted from the light projecting unit 20 and the optical axis of the optical system for light receiving 31 of the light receiving unit 30 on the surface to be measured 101 at the first relative position (first color measurement position) may be short compared to a distance at the second relative position (second color measurement position). That is, lightness indicated by color measurement data becomes higher as a distance between the central axis of light flux emitted from the light projecting unit 20 and the optical axis of the optical system for light receiving 31 of the light receiving unit 30 on the surface to be measured 101 becomes shorter. Thus, by setting the first color measurement position where a lightness determination value is high, compared to the second color measurement position, as a color measurement position for generating color conversion information and performing color measurement, a relative position among the light projecting unit 20, the light receiving unit 30, and the surface to be measured 101 is brought closer to the reference position and color measurement can be performed with high accuracy compared to a case where color measurement is performed at the second color measurement position.

In addition, although color measurement is performed at two points (n=2), including the first relative position (first color measurement position) and the second relative position (second color measurement position) in the embodiment, the invention is not particularly limited thereto. Color measurement may be performed at three or more different relative positions. That is, color measurement may be performed at a plurality of relative positions with different heights of the color measuring unit 10 from the surface to be measured 101 in the third direction Z, and a relative position at which the highest lightness is measured may be set as a color measurement position (first relative position) for generating color conversion information. Although it is desirable that a relative position where the highest lightness is measured be set as a color measurement position for generating color conversion information in a case where color measurement is performed at a plurality of relative positions with different heights of the color measuring unit 10 from the surface to be measured 101, a relative position where high lightness is measured, even though the lightness is not the highest, can also be set as a color measurement position for generating color conversion information. Also in this case, colors can be accurately measured than in a case where a relative position where lower lightness is measured is set as a color measurement position for generating color conversion information. Accordingly, color measurement accuracy can be increased by making a distance between the central axis of light flux emitted from the light projecting unit 20 and the optical axis of the optical system for light receiving 31 of the light receiving unit 30 as short as possible and bringing a relative position among the light projecting unit 20, the light receiving unit 30, and the surface to be measured 101 closer to a reference position.

In addition, by performing the setting of a color measurement position for generating color conversion information based on a lightness determination value obtained by measuring colors at three or more relative positions with different heights of the color measuring unit 10 from the surface to be measured 101, the central axis of light flux from the light projecting unit 20 and the optical axis of the optical system for light receiving 31 of the light receiving unit 30 are brought as close as possible to each other on the surface to be measured 101 and the colors of the surface to be measured 101 can be measured with higher accuracy. Consequently, it is preferable to perform color measurement at as many relative positions with different heights of the color measuring unit 10 from the surface to be measured 101 as possible, in order to perform highly accurate color measurement at higher lightness. However, by increasing the number of relative positions for color measurement with different the heights of the color measuring unit 10 from the surface to be measured 101, the number of times of color measurement increases and thus it takes time for color measurement. Therefore, in a case where lightness when colors are accurately measured is known beforehand based on test results, a threshold is set based on the lightness, color measurement may be performed at a plurality of relative positions with different heights of the color measuring unit 10 from the surface to be measured 101 in the third direction Z, and a relative position (first relative position), at which lightness higher than a predetermined lightness (threshold) is measured, may be a color measurement position for generating color conversion information. Accordingly, the central axis of light flux emitted from the light projecting unit 20 and the optical axis of the optical system for light receiving 31 of the light receiving unit 30 are disposed on the surface to be measured 101 within a predetermined distance range and thus color measurement accuracy can be increased. In addition, it is not necessary to perform color measurement until the central axis of light flux emitted from the light projecting unit 20 and the optical axis of the optical system for light receiving 31 of the light receiving unit 30 match on the surface to be measured 101. Thus, the number of times of color measurement can be decreased and time necessary for color measurement can be shortened.

As described above, in a driving method for a liquid ejecting apparatus including an ink jet recording head ejecting an ink, which is a liquid, onto the recording sheet 100, which is a medium, and the color measuring unit 10, which includes the light projecting unit 20 irradiating the surface to be measured 101 of the recording sheet 100 with light and the light receiving unit 30 receiving light, which is emitted from the light projecting unit 20 and is reflected by the surface to be measured 101 of the recording sheet 100, and measures the colors of the surface to be measured 101 of the recording sheet 100, the light projecting unit 20, the light receiving unit 30, and the recording sheet 100 are set at a first color measurement position, which is a first relative position, the light, which is emitted from the light projecting unit 20 and is reflected by the surface to be measured 101 of the recording sheet 100, is received by the light receiving unit 30, and a first color measurement value including a value indicating the lightness of the surface to be measured 101 of the recording sheet 100 is measured. In addition, the light projecting unit 20, the light receiving unit 30, and the recording sheet 100 are set at a second color measurement position, which is a second relative position different from the first relative position, the light, which is emitted from the light projecting unit 20 and is reflected by the surface to be measured 101 of the recording sheet 100, is received by the light receiving unit 30, and a second color measurement value indicating the lightness of the surface to be measured 101 of the recording sheet 100 is measured. In a case where lightness indicated by the first color measurement value is higher than lightness indicated by the second color measurement value, the first color measurement position, which is the first relative position, is set as a color measurement position, print data is color-converted with color conversion information based on the colors of the recording sheet 100 measured at the color measurement position or the color measurement value of a patch printed on the recording sheet 100.

As described above, color measurement is performed at the first relative position and the second relative position. By setting the first relative position where lightness is high as a color measurement position, and measuring the colors of the recording sheet 100 or measuring the colors of a patch printed on the recording sheet 100 at the color measurement position, highly accurate color measurement can be performed. In addition, by color-converting print data with color conversion information based on a color measurement value, printing excellent in color reproducibility can be realized.

In addition, since it is desirable to perform color measurement at least two relative positions, including the first relative position and the second relative position, in the embodiment, color measurement time can be shortened.

Since the thickness of the recording sheet 100 differs according to a type, the height of the color measuring unit 10 from the surface to be measured 101 of the recording sheet 100 in the third direction Z differs according to the thickness of the recording sheet 100 when the height of the color measuring unit 10 from a supporting surface 8a of the supporting member 8 is fixed. However, in the embodiment, since color measurement is performed at the first relative position and the second relative position with different heights of the color measuring unit 10 from the recording sheet 100 in the third direction Z and a relative position where higher lightness is measured can be set as a color measurement position for generating color conversion information, the occurrence of variations in the height of the color measuring unit 10 from the surface to be measured 101, which is caused by variations in the thickness of the recording sheet 100, at the color measurement position where colors are measured to generate color conversion information is suppressed, and color measurement accuracy can be improved.

In addition, the light projecting unit 20, the light receiving unit 30, and the recording sheet 100, which is a medium, are set at a plurality of relative positions, which are three or more different relative positions among the light projecting unit 20, the light receiving unit 30, and the recording sheet 100, including the first relative position and the second relative position. It is preferable that light, which is emitted from the light projecting unit 20 and is reflected by the surface to be measured 101 of the recording sheet 100, be received by the light receiving unit 30 and a color measurement value indicating the lightness of the surface to be measured 101 of the recording sheet 100 be measured, at each of the plurality of relative positions. According to this, color measurement accuracy can be increased by making a distance between the central axis of light flux emitted from the light projecting unit 20 and the optical axis of the optical system for light receiving 31 of the light receiving unit 30 as short as possible and bringing a relative position among the light projecting unit 20, the light receiving unit 30, and the surface to be measured 101 closer to a reference position.

In addition, it is preferable that lightness indicated by the first color measurement value be the highest among the lightness levels indicated by color measurement values measured at the plurality of relative positions. According to this, colors can be measured at high lightness and color measurement accuracy can be increased by making a distance between the central axis of light flux emitted from the light projecting unit 20 and the optical axis of the optical system for light receiving 31 of the light receiving unit 30 as short as possible.

Embodiment 6

Figure 30:
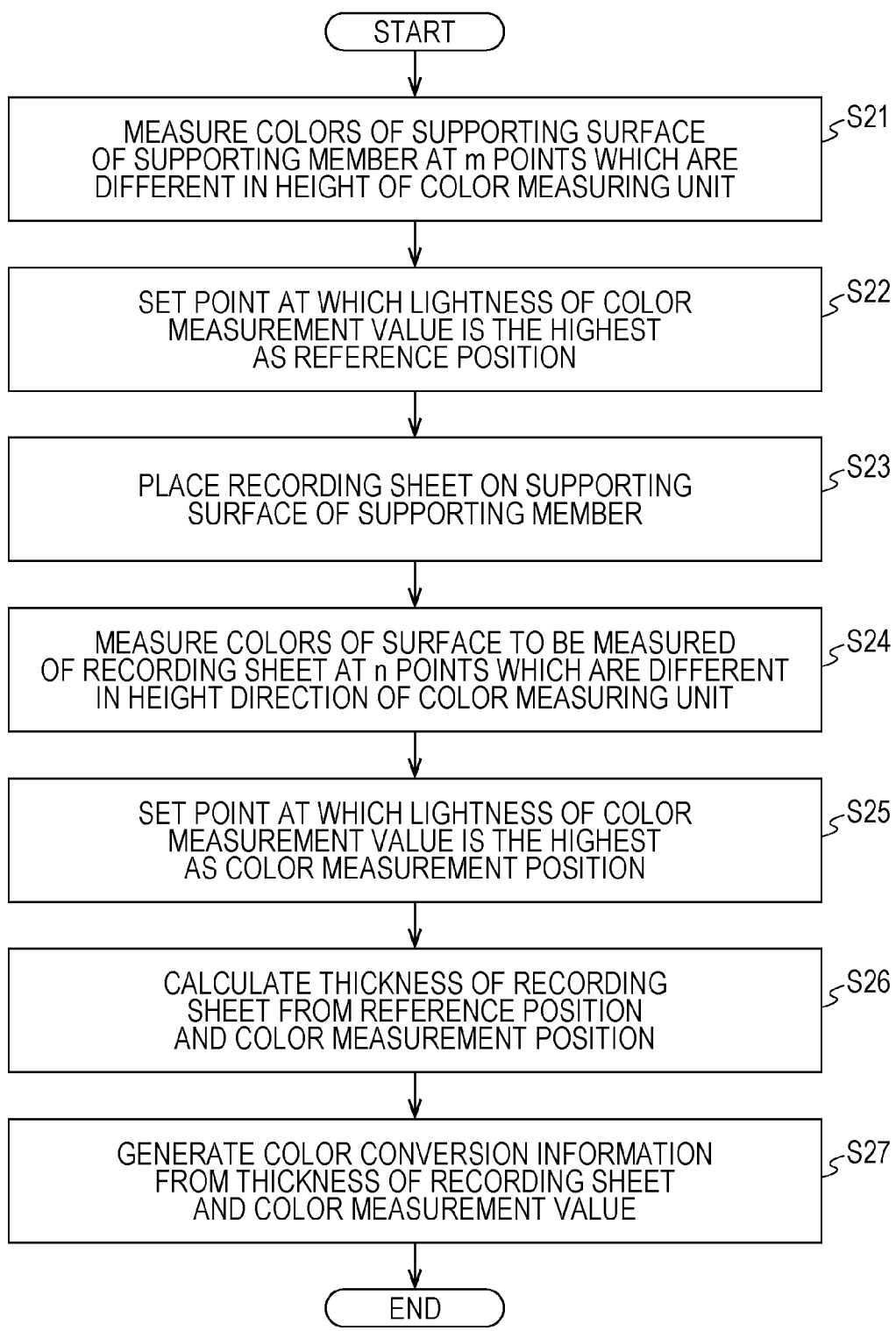
FIG. 30 is a flow chart showing a driving method according to Embodiment 6.
Figure 31:
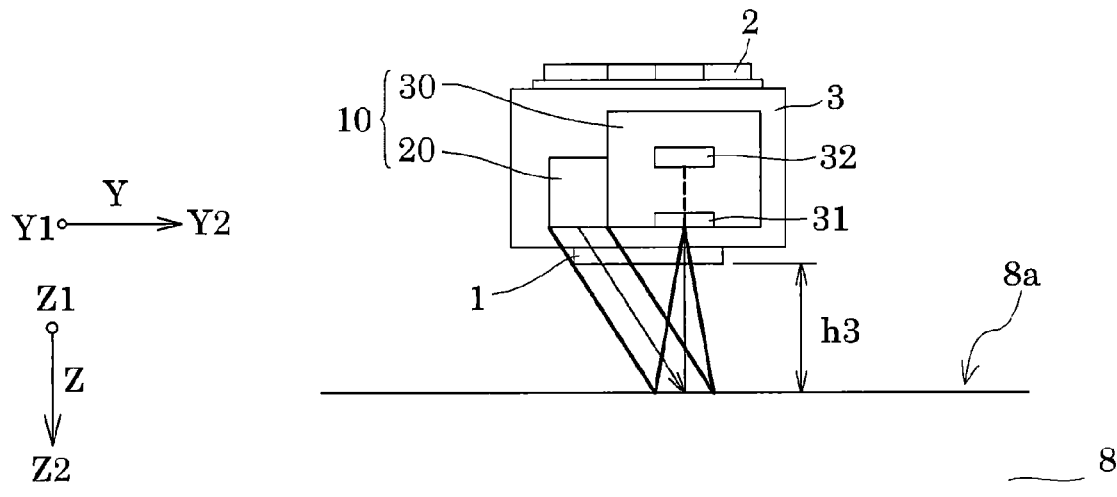
FIG. 31 is a side view of main portions of a recording apparatus according to Embodiment 6.
Figure 32:
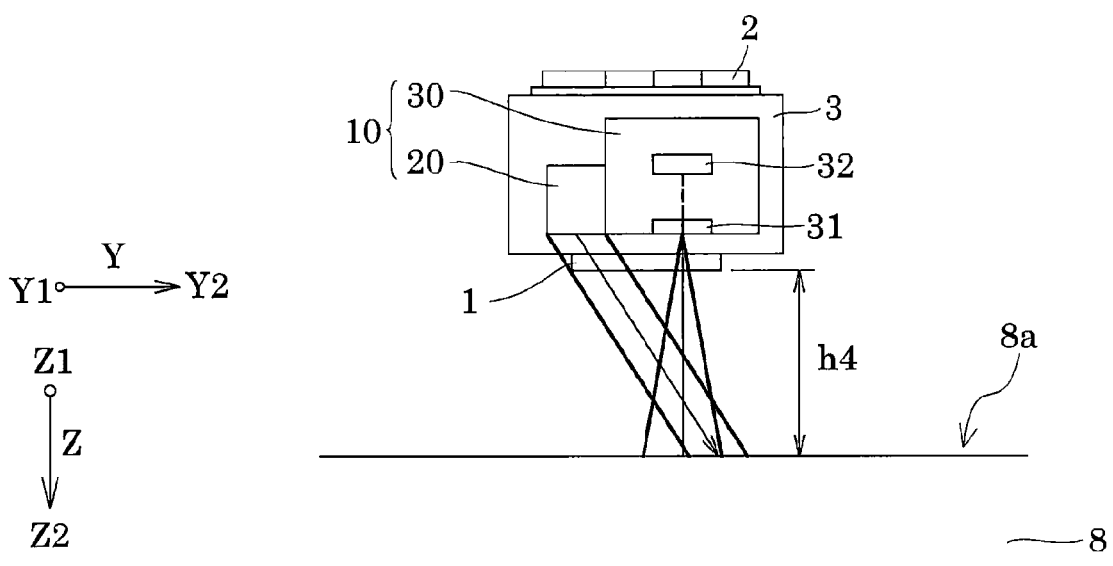
FIG. 32 is a side view of the main portions of the recording apparatus according to Embodiment 6.

FIG. 30 is a flow chart showing a driving method for an ink jet recording apparatus, which is an example of a liquid ejecting apparatus according to Embodiment 6 of the invention, and FIG. 31 and FIG. 32 are side views of main portions of an ink jet recording apparatus. The same members as in the embodiment described above will be assigned with the same reference signs and overlapping description will be omitted. In the embodiment, the thickness of the recording sheet 100 is measured with the use of the color measuring unit 10 and the changing unit 40, and a color measurement position for generating color conversion information is set as in Embodiment 5.

As illustrated in FIG. 30, in a driving method for a liquid ejecting apparatus of the embodiment, in Step S21, the colors of the supporting surface 8a of the supporting member 8 supporting the recording sheet 100, which is a recording medium, are measured at m points (m 2, m is a natural number), which are different positions of the color measuring unit 10 in the third direction Z, and generated color measurement data is associated with a color measurement position (position of the color measuring unit 10 in the third direction Z) and is stored in the memory unit 212. In the embodiment, colors are measured at two points (m=2), which are different positions of the color measuring unit 10 in the third direction Z. Specifically, the colors of the supporting surface 8a of the supporting member 8 are measured at a third color measurement position where the height of the color measuring unit 10 is a height h3 as illustrated in FIG. 31 and a fourth color measurement position where the height of the color measuring unit 10 is a height h4 (h3≠h4) as illustrated in FIG. 32. That is, as illustrated in FIG. 31, the light projecting unit 20, the light receiving unit 30, and the recording sheet 100 are set at a third relative position (third color measurement position where the height of the color measuring unit 10 is h3), and a third color measurement value including a value indicating the lightness of the supporting surface 8a of the supporting member 8 is measured. Specifically, the third color measurement value (color measurement data) quantified under the color system from results measured by the color measuring unit 10 at the third color measurement position is associated with the third color measurement position and is stored in the memory unit 212. In addition, as illustrated in FIG. 32, the light projecting unit 20, the light receiving unit 30, and the recording sheet 100 are set at a fourth relative position (fourth color measurement position where the height of the color measuring unit 10 is h4), which is different from the third relative position, and a fourth color measurement value including a value indicating the lightness of the supporting surface 8a of the supporting member 8 is measured. Specifically, the fourth color measurement value (color measurement data) quantified under the color system from results measured by the color measuring unit 10 at the fourth color measurement position is associated with the fourth color measurement position and is stored in the memory unit 212. In the embodiment, the third relative position (third color measurement position) and the fourth relative position (fourth color measurement position) are the same when an interval between the light projecting unit 20 and the light receiving unit 30 in the second direction Y is the reference interval and an angle between the central axis of light flux emitted from the light projecting unit 20 and the optical axis of the optical system for light receiving 31 of the light receiving unit 30 with respect to the normal line of the surface to be measured 101 is the reference angle. Information of a reference relative position is stored in the memory unit 212. The reference relative position is a position where the height of the color measuring unit 10 for the supporting surface 8a is a reference height h0, the irradiation angle of the light projecting unit 20 with respect to a normal line of the supporting surface 8a and the angle of the optical axis of the optical system for light receiving 31 of the light receiving unit 30 with respect to the normal line of the supporting surface are reference angles, an interval between the light receiving unit 30 and the light projecting unit 20 in the second direction Y is a reference interval, and the central axis of light flux from the light projecting unit 20 and the optical axis of the optical system for light receiving 31 of the light receiving unit 30 match on the supporting surface 8a. Accordingly, at a color measurement position for generating color conversion information, which will be described later, a relative position among the light projecting unit 20, the light receiving unit 30, and the surface to be measured 101 is set at the reference position and the colors of the recording sheet 100 can be accurately measured. As a result, variations in color measurement accuracy, which are caused by variations in the thickness of the recording sheet 100, can be suppressed and the thickness of the recording sheet 100 can be accurately measured.

Next, in Step S22, out of the third color measurement value and the fourth color measurement value, which are measured at the third color measurement position and the fourth color measurement position, a position where lightness is the highest is set as a reference position. In the embodiment, since a lightness determination value LA1 to determine lightness indicated by the third measurement value measured at the third color measurement position, is higher than a lightness determination value LA2 to determine lightness indicated by the fourth measurement value measured at the fourth color measurement position (LA1>LA2), the third color measurement position is set as a reference position. Specifically, the third color measurement position associated with the higher lightness determination value LA1 (third color measurement value) is set as a reference position for measuring the thickness of the recording sheet 100 in the memory unit 212.

Although a case where the central axis of light flux emitted from the light projecting unit 20 and the optical axis of the optical system for light receiving 31 of the light receiving unit 30 match on the supporting surface 8a at the third relative position (third color measurement position) as illustrated in FIG. 31 is given as an example in the embodiment, the invention is not particularly limited thereto. A case where the central axis of light flux emitted from the light projecting unit 20 and the optical axis of the optical system for light receiving 31 of the light receiving unit 30 do not match on the supporting surface 8a at the third relative position (third color measurement position) is also included in the embodiment. That is, a distance between the central axis of light flux emitted from the light projecting unit 20 and the optical axis of the optical system for light receiving 31 of the light receiving unit 30 on the supporting surface 8a, at the third relative position (third color measurement position) may be short compared to a distance at the fourth relative position (fourth color measurement position). That is, lightness indicated by color measurement data becomes higher as a distance between the central axis of light flux emitted from the light projecting unit 20 and the optical axis of the optical system for light receiving 31 of the light receiving unit 30 on the supporting surface 8a becomes shorter. Thus, by setting the third color measurement position where a lightness determination value is high, compared to the fourth color measurement position, as a reference position and performing the measurement of the thickness of the recording sheet 100, a relative position among the light projecting unit 20, the light receiving unit 30, and the supporting surface 8a is brought closer to a reference position, and the measurement of the thickness of the recording sheet 100 can be performed with high accuracy compared to a case where the fourth color measurement position is set as a reference position and the measurement of the thickness of the recording sheet 100 is performed. That is, by a relative position among the light projecting unit 20, the light receiving unit 30, and the supporting surface 8a and a relative position among the light projecting unit 20, the light receiving unit 30, and the surface to be measured 101, which are at a reference position, being brought closer to each other, the thickness of the recording sheet 100 can be accurately measured from a difference between the height of the color measuring unit 10, which is at the reference position, from the supporting surface 8a and the height of the color measuring unit 10, which is at the color measurement position, from the supporting surface 8a.

In addition, although color measurement is performed at two points (m=2), including the third relative position (third color measurement position) and the fourth relative position (fourth color measurement position), in the embodiment, the invention is not particularly limited thereto. Color measurement may be performed at three or more different relative positions. That is, color measurement may be performed at a plurality of relative positions with different heights of the color measuring unit 10 from the supporting surface 8a in the third direction Z, and a relative position at which the highest lightness is measured may be set as a reference position (third relative position) for measuring the thickness of the recording sheet 100. In a case where color measurement is performed at a plurality of relative positions with different heights of the color measuring unit 10 from the supporting surface 8a in the third direction Z, it is desirable that a relative position at which the highest lightness is measured be set as a reference position for measuring the thickness of the recording sheet 100. That is because the thickness of the recording sheet 100 can be more accurately measured when the height of the color measuring unit 10, which is at a color measurement position for generating color conversion information corresponding to the recording sheet 100, from the surface to be measured 101 is equal to the height of the color measuring unit 10, which is at the reference position, from the supporting surface 8a. However, when a relative position where higher lightness is measured, even though the lightness is not the highest, can be set as a reference position for measuring the thickness of the recording sheet 100, the thickness of the recording sheet 100 can be more accurately measured than in a case where a relative position at which lower lightness is measured is set as a reference position. Accordingly, the accuracy of measuring the thickness of the recording sheet 100 can be increased by making a distance between the central axis of light flux emitted from the light projecting unit 20 and the optical axis of the optical system for light receiving 31 of the light receiving unit 30 on the supporting surface 8*a* as short as possible and bringing a relative position among the light projecting unit 20, the light receiving unit 30, and the supporting surface 8*a* closer to a reference position.

In addition, by performing the setting of a reference position for measuring the thickness of the recording sheet 100 based on a lightness determination value obtained by measuring colors at three or more relative positions with different heights of the color measuring unit 10 from the supporting surface 8*a*, a position where the central axis of light flux from the light projecting unit 20 and the optical axis of the optical system for light receiving 31 of the light receiving unit 30 are brought as close as possible to each other on the supporting surface 8*a* can be set as a reference position. Consequently, it is preferable to perform color measurement at as many relative positions with different heights of the color measuring unit 10 from the supporting surface 8*a* as possible, in order to perform the measurement of the thickness of the recording sheet 100 at higher accuracy. However, by increasing the number of relative positions for color measurement with different heights of the color measuring unit 10 from the supporting surface 8*a*, the number of times of color measurement increases and thus it takes time for color measurement. Therefore, in a case where lightness when colors are accurately measured is known beforehand based on test results, a threshold is set based on the lightness, color measurement may be performed at a plurality of relative positions with different heights of the color measuring unit 10 from the supporting surface 8*a* in the third direction Z, and a relative position (third relative position), at which lightness higher than a predetermined lightness (threshold) is measured, may be a reference position for measuring the thickness of the recording sheet 100. Accordingly, the accuracy of measuring the thickness of the recording sheet 100 can be increased with a position where the central axis of light flux emitted from the light projecting unit 20 and the optical axis of the optical system for light receiving 31 of the light receiving unit 30 are disposed on the supporting surface 8*a* within a predetermined distance range being as a reference position. In addition, it is not necessary to perform color measurement until the central axis of light flux emitted from the light projecting unit 20 and the optical axis of the optical system for light receiving 31 of the light receiving unit 30 match. Thus, the number of times of color measurement can be decreased, and time necessary for color measurement can be shortened.

Next, in Step S23, the recording sheet 100, which is a medium, is provided on the supporting surface 8*a* of the supporting member 8.

Next, in Step S24 to Step S25, a point where color measurement data indicating the highest lightness is obtained is set as a color measurement position. Since Step S24 to Step S25 are the same as Step S11 to Step S12 of Embodiment 5, detailed description thereof will be omitted.

Next, in Step S26, the thickness of the recording sheet 100 is calculated from a difference between the reference position set in Step S22 and the color measurement position set in Step S25. That is, the thickness of the recording sheet 100 can be calculated from a difference between the height of the color measuring unit 10 at the third color measurement position, which is the reference position, from the supporting surface 8*a* and the height of the color measuring unit 10 at the first color measurement position, which is the color measurement position, from the supporting surface 8*a* since the heights of the color measuring unit 10 from the supporting member 8 and the recording sheet 100, which are color measurement targets, in the third direction Z are the same at the third color measurement position where higher lightness is measured, out of color measurement data pieces of the supporting surface 8*a* of the supporting member 8, and the first color measurement position where higher lightness is measured, out of color measurement data pieces of the surface to be measured 101 of the recording sheet 100.

Next, in Step S27, the type of the recording sheet 100 is determined from the calculated thickness of the recording sheet 100 and the first color measurement value corresponding to the first color measurement position, which is the color measurement position stored in the memory unit 212 in Step S24 (paper white value of the recording sheet 100), and color conversion information is generated based on the type of the recording sheet 100. After then, printing is executed with print data (image data) that is color-converted based on color conversion information.

The colors of a patch, on which ink droplets discharged from the recording head is landed, that is, so-called printing is performed, on the surface to be measured 101 is measured at a color measurement position for generating color conversion information (color measurement position set in Step S25), and printing can be executed based on the color measurement value, which is based on color conversion information.

There are a plurality of types of recording sheets having different materials and thicknesses according to manufacturers, which manufacture recording sheets, and use. For this reason, the recording sheet 100 can be identified based on the thickness of the recording sheet 100 and a paper white value measured by the color measuring unit 10. By identifying the recording sheet 100, an optimal print setting can be performed for the identified recording sheet 100. For example, by accumulating the thicknesses and the paper white values of the plurality of types of recording sheets and an optimal print setting for each recording sheet as data in advance and identifying the type of the recording sheet 100 from the thickness and the paper white value of the recording sheet 100, an optimal print setting for the identified recording sheet 100 can be called up. In addition, for example, a paper white value and a thickness, which are measured by the color measuring unit 10 in the past, and a print setting, which is set by a user when printing the recording sheet 100, may be stored, and a print setting set in the past may be called up when the recording sheet 100 that is the same as the recording sheet 100, of which colors are measured and which is printed in the past, in terms of a paper white value and a thickness is detected.

The recording sheet 100 differs in terms of color reproducibility, ink absorbability, ease of occurrence of a kink due to the landing of an ink, and drying time according to a type, such as a material and a thickness. Therefore, by identifying the recording sheet 100, color reproducibility based on the ratio of a plurality of element colors used by the ink jet recording apparatus I, for example, cyan (C), magenta (M), yellow (Y), and black (K), the weight (poured amount) of ink droplets, paper gap (PG), the moving speed of the carriage 3, and paper feeding speed can be optimally set for the recording sheet 100. After being called up as a print setting, color reproducibility may be corrected based on results of color measurement by the color measuring unit 10.

As described above, in the embodiment, the supporting member 8 that supports the opposite surface of the light projecting unit 20, the light receiving unit 30, and the surface to be measured 101 of the recording sheet 100, which is a medium, is set at the third color measurement position, which is the third relative position. Light, which is emitted from the light projecting unit 20 and is reflected by the supporting surface 8a of the supporting member 8 supporting the recording sheet 100, is received by the light receiving unit 30. The third color measurement value including a value indicating the lightness of the supporting surface of the supporting member 8 is measured. The light projecting unit 20, the light receiving unit 30, and the supporting member 8 are set at the fourth relative position, which is different from the third relative position. The light, which is emitted from the light projecting unit 20 and is reflected by the supporting surface of the supporting member 8, is received by the light receiving unit 30. The fourth color measurement value indicating the lightness of the supporting surface of the supporting member 8 is measured. In a case where lightness indicated by the third color measurement value is higher than lightness indicated by the fourth color measurement value, the third relative position is set as a reference position and the thickness of the recording sheet 100 is detected from a difference between the color measurement position and the reference position. By the color measuring unit 10 detecting the thickness of the recording sheet 100 as described above, costs can be reduced since an another separate sensor that measures the thickness of the recording sheet 100 is unnecessary, and miniaturization can be achieved since a space to dispose the sensor is unnecessary. In addition, the changing unit 40 can control a paper gap, which is an interval between the recording sheet 100 and the recording head 1, with high accuracy by acquiring the thickness of the recording sheet 100. Therefore, highly accurate printing can be realized.

In addition, although a reference position for measuring the thickness of the recording sheet 100 is set by measuring the colors of the supporting surface 8a of the supporting member 8 at the third color measurement position and the fourth color measurement position in the embodiment, a reference position, for example, may be stored in the memory unit 212. As a result, it is not necessary to repeatedly acquire a reference position and thus color measurement time can be shortened. That is, by acquiring a reference position first and storing the position in the memory unit 212 since the reference position does not vary for each color measurement and is constant at all times, Steps S21 and S22 can be omitted at the time of color measurement, and thus color measurement time can be shortened.

Embodiment 7

Figure 33:
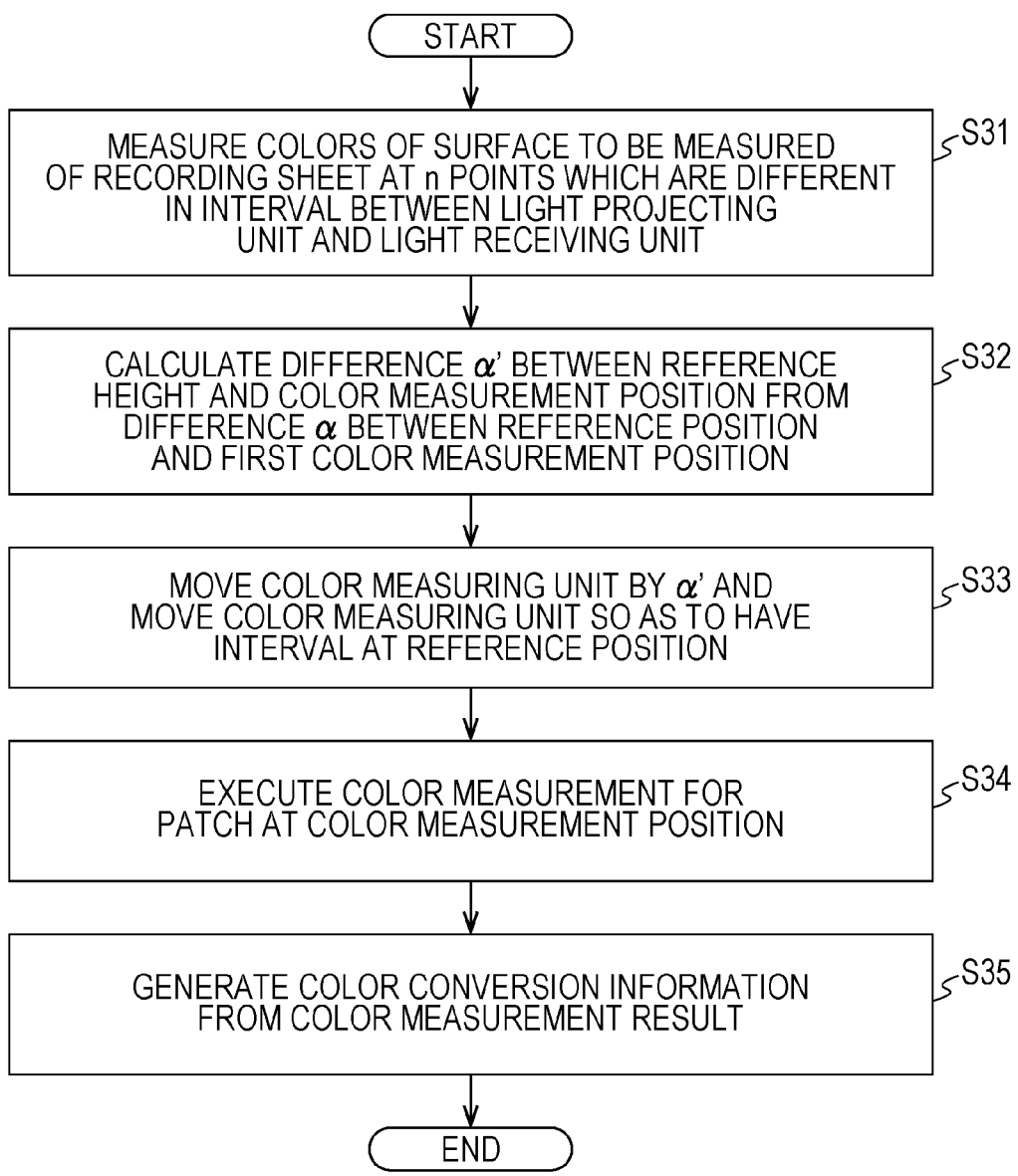
FIG. 33 is a flow chart showing a driving method according to Embodiment 7.

FIG. 33 is a flow chart showing a driving method for an ink jet recording apparatus, which is an example of a liquid ejecting apparatus according to Embodiment 7 of the invention, and FIG. 34 to FIG. 37 are side views of main portions of an ink jet recording apparatus. The same members as in the embodiment described above will be assigned with the same reference signs and overlapping description will be omitted.

Figure 37:
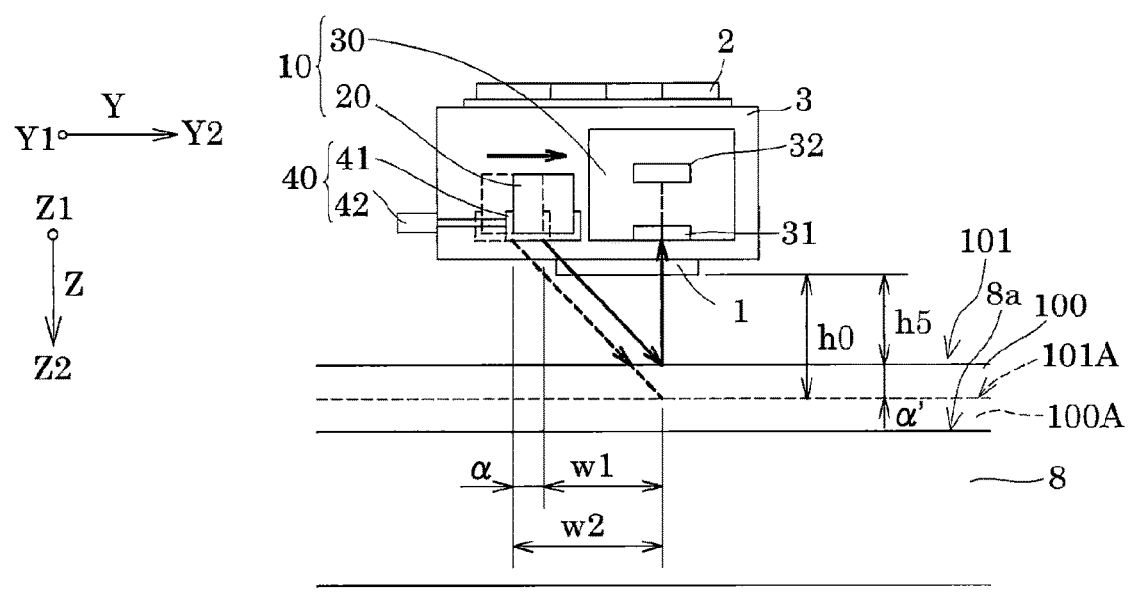
FIG. 37 is a side view of the main portions of the recording apparatus according to Embodiment 7.

As illustrated in FIG. 33, in a driving method for a liquid ejecting apparatus of Embodiment 7 of the invention, in Step S31, the colors of the surface to be measured 101 of the recording sheet 100 are measured at n points (n 2, n is a natural number) with different intervals (distances) between the light projecting unit 20 and the light receiving unit 30 in the second direction Y, and generated color measurement data is associated with a color measurement position (position of the color measuring unit 10 in the third direction Z) and is stored in the memory unit 212. In the embodiment, colors are measured at two n points (n=2) with different intervals between the light projecting unit 20 and the light receiving unit 30 in the second direction Y. Specifically, as illustrated in FIG. 37, the colors of the surface to be measured 101 of the recording sheet 100 are measured at the first color measurement position where an interval between the light projecting unit 20 and the light receiving unit 30 is the interval w1 and at the second color measurement position where an interval between the light projecting unit 20 and the light receiving unit 30 is the interval w2 (w1≠w2). That is, the light projecting unit 20, the light receiving unit 30, and the recording sheet 100 are set at a first relative position (first color measurement position where an interval between the light projecting unit 20 and the light receiving unit 30 is w1), and a first color measurement value including a value indicating the lightness of the surface to be measured 101 of the recording sheet 100 is measured. Specifically, the first color measurement value (color measurement data) quantified under the color system from results measured by the color measuring unit 10 at the first color measurement position is associated with the first color measurement position and is stored in the memory unit 212. In addition, the light projecting unit 20, the light receiving unit 30, and the recording sheet 100 are set at a second relative position (second color measurement position where an interval between the light projecting unit 20 and the light receiving unit 30 is w2), which is different from the first relative position, and a second color measurement value including a value indicating the lightness of the surface to be measured 101 of the recording sheet 100 is measured. Specifically, the second color measurement value (color measurement data) quantified under the color system from results measured by the color measuring unit 10 at the second color measurement position is associated with the second color measurement position and is stored in the memory unit 212. In the embodiment, at the first relative position (first color measurement position) and the second relative position (second color measurement position), the height of the color measuring unit 10 from the surface to be measured 101 (intervals between the color measuring unit 10 and the recording sheet 100) is the reference height h0 or a predetermined height, and the angle between the central axis of light flux emitted from the light projecting unit 20 and the optical axis of the optical system for light receiving 31 of the light receiving unit 30 with respect to the normal line of the surface to be measured 101 is a reference angle. Accordingly, at a color measurement position for generating color conversion information, which will be described later, a relative position among the light projecting unit 20, the light receiving unit 30, and the surface to be measured 101 is set at a reference position and the colors of the recording sheet 100 can be accurately measured. As a result, variations in color measurement accuracy, which are caused by variations in the thickness of the recording sheet 100, can be suppressed.

In addition, color measurement at the first color measurement position and the second color measurement position may be performed as follows. For example, the colors of the surface to be measured 101 of the recording sheet 100, that is, the colors of the recording sheet 100 itself may be measured, or the colors of a patch, on which ink droplets discharged from the recording head are landed, that is, so-called printing is performed, on the surface to be measured 101, may be measured.

Figure 34:
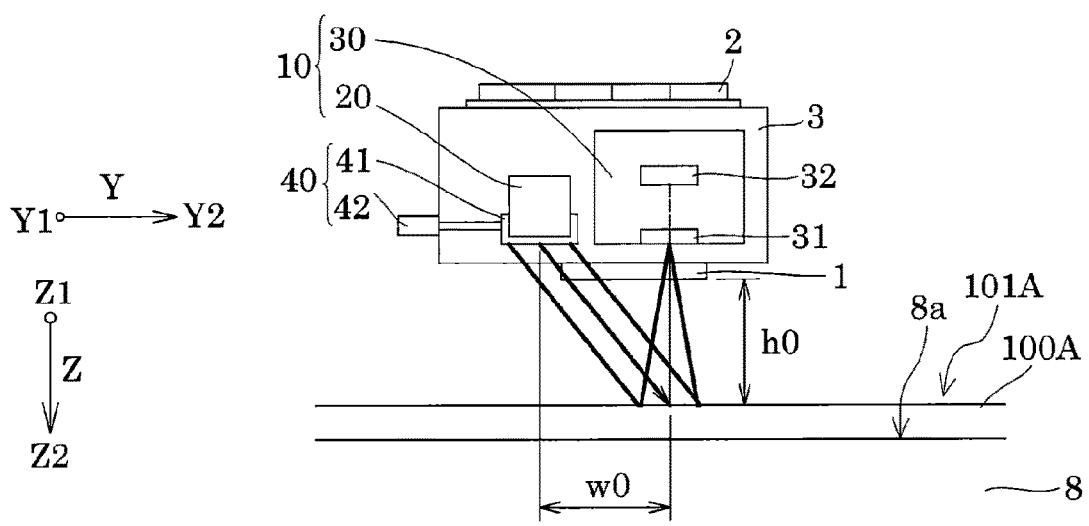
FIG. 34 is a side view of main portions of a recording apparatus according to Embodiment 7.

In the embodiment, as illustrated in FIG. 34, in a case where the recording sheet 100A, of which a thickness is reference, is used, a relative position among the light projecting unit 20, the light receiving unit 30, and the surface to be measured 101A, at which the colors of the reference recording sheet 100A can be appropriately measured, is set as a reference relative position. At the reference relative position, the height of the surface to be measured 101A of the color measuring unit 10 is the reference height h0, the irradiation angle of the light projecting unit 20 with respect to the normal line of the surface to be measured 101A and the angle of the optical axis of the optical system for light receiving 31 of the light receiving unit 30 with respect to the normal line of the surface to be measured are reference angles, an interval between the light receiving unit 30 and the light projecting unit 20 in the second direction Y is a reference interval w0. At such a reference relative position, the central axis of light flux from the light projecting unit 20 and the optical axis of the optical system for light receiving 31 of the light receiving unit 30 match on the surface to be measured 101A of the recording sheet 100A, which is reference. That is, in a case where the light projecting unit 20, the light receiving unit 30, and the surface to be measured 101A of the recording sheet 100A, which is reference, are disposed at the reference relative position, lightness indicated by color measurement data is the highest. Information of a reference relative position indicating such a reference position where the light projecting unit 20, the light receiving unit 30, and the surface to be measured 101A are disposed is stored in the memory unit 212.

In the embodiment, a reference relative position (hereinafter, also simply referred to as a reference position) is set as the second color measurement position (second relative position). That is, a case where the interval (distance) w2 between the light receiving unit 30 and the light projecting unit 20 in the second direction Y at the second relative position is equal to the reference interval (distance) w0 will be described. When the colors of the surface to be measured 101 of the recording sheet 100, of which a thickness is different from the thickness of the reference recording sheet 100A, are measured at such a second relative position (reference position), a difference between the height of the color measuring unit 10 from the surface to be measured 101 in the third direction Z and the reference height h0 occurs by the amount of a difference between the thickness of the recording sheet 100A, which is reference, and the thickness of the recording sheet 100 and the central axis of light flux from the light projecting unit 20 and the optical axis of the optical system for light receiving 31 of the light receiving unit 30 are deviated from each other on the surface to be measured 101.

Figure 35:
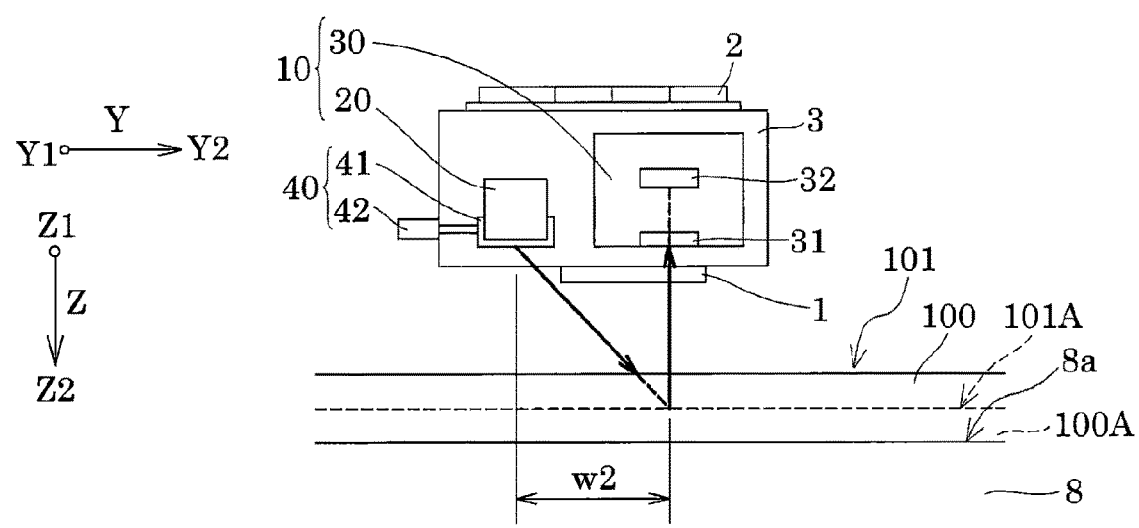
FIG. 35 is a side view of the main portions of the recording apparatus according to Embodiment 7.
Figure 36:
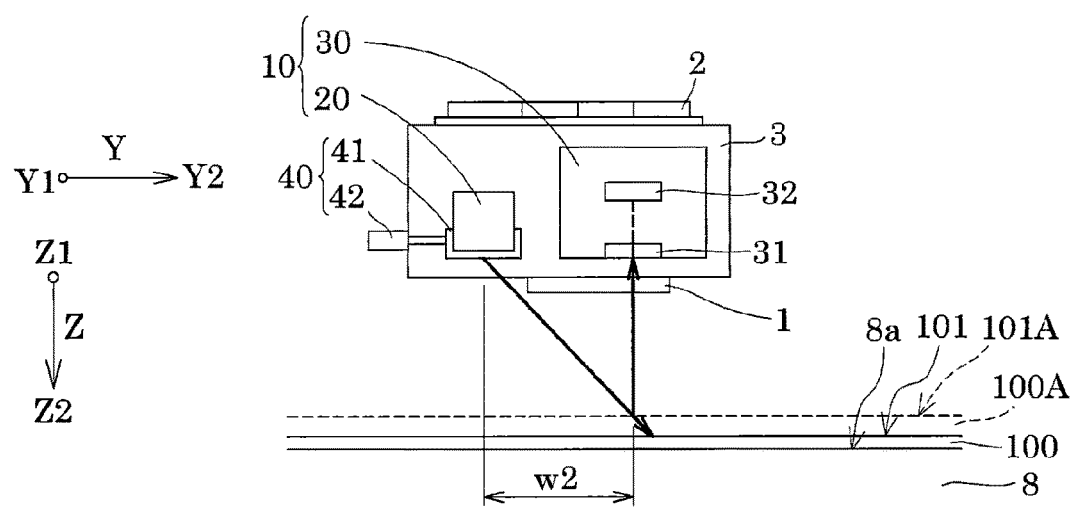
FIG. 36 is a side view of the main portions of the recording apparatus according to Embodiment 7.

For example, as illustrated in FIG. 35, in a case where the thickness of the recording sheet 100 is larger than the thickness of the recording sheet 100A, which is reference, the central axis of light flux from the light projecting unit 20 and the optical axis of the optical system for light receiving 31 of the light receiving unit 30 are at different positions on the surface to be measured 101, at the second color measurement position (reference position). As illustrated in FIG. 36, also in a case where the thickness of the recording sheet 100 is smaller than the thickness of the recording sheet 100A, which is reference, the central axis of light flux from the light projecting unit 20 and the optical axis of the optical system for light receiving 31 of the light receiving unit 30 are at different positions on the surface to be measured 101, at the second color measurement position (reference position).

In the embodiment, as shown in FIG. 12, the control unit for a color measuring unit 300 controls the color measuring unit 10 to perform color measurement while the control unit for a changing unit 302 controlling the changing unit 40 to change an interval between the light projecting unit 20 and the light receiving unit 30 in the second direction Y. The color measurement processing unit 301 quantifies colors under the color system and generates color measurement data from measurement results from the color measuring unit 10. The color measurement data is associated with reflection position data and is stored in the memory unit 212. In the embodiment, an interval between the light projecting unit 20 and the light receiving unit 30 in the second direction Y is reflection position data. Next, reflection position data associated with color measurement data, which is determined as color measurement data indicating the highest lightness by the lightness determining unit 303, is identified from a plurality of pieces of color measurement data. For example, in a case where the thickness of the recording sheet 100 illustrated in FIG. 35 is larger than the thickness of the recording sheet 100A, which is reference, the central axis of light flux from the light projecting unit 20 and the optical axis of the optical system for light receiving 31 of the light receiving unit 30 match on the surface to be measured 101 at the interval w1, which is narrower than the interval w2 between the light projecting unit 20 and the light receiving unit 30, as illustrated in FIG. 37, and the light receiving unit 30 can receive the strongest light. Consequently, the interval w1 between the light projecting unit 20 and the light receiving unit 30 in the second direction Y, which is at the first color measurement position, can be identified as reflection position data indicating the highest lightness.

Next, in Step S32, a difference $\alpha'$ between the reference height h0 of the color measuring unit 10 from the surface to be measured 101A in the third direction Z and a height h5 of the color measuring unit 10 from the surface to be measured 101 in the third direction Z, which is at the first color measurement position, is calculated from a difference $\alpha$ (w2−w1) between the interval w2 between the light projecting unit 20 and the light receiving unit 30, which is at the reference position, and the interval w1 between the light projecting unit 20 and the light receiving unit 30, which is at the first color measurement position that is reflection position data associated with the color measurement data determined as data indicating the highest lightness in Step S31. For example, a conversion table, in which the difference $\alpha$ between the interval w2 between the light projecting unit 20 and the light receiving unit 30, which is at the reference position, and the interval w1 between the light projecting unit 20 and the light receiving unit 30, which is at the first color measurement position, and the difference $\alpha'$ between the reference height h0 of the color measuring unit 10 from the surface to be measured 101A and the height h5 of the color measuring unit 10 from the surface to be measured 101, which is at the first color measurement position, are associated with each other, is prepared. Based on the conversion table, the difference $\alpha'$ between the reference height h0 of the color measuring unit 10 in the third direction Z and the height h5 at the first color measurement position is acquired from the difference $\alpha$ between the intervals w1 and w2 between the light projecting unit 20 and the light receiving unit 30.

Next, in Step S33, the color measuring unit 10 is moved from the height h5 from the surface to be measured 101 at the first color measurement position in the third direction Z by the difference $\alpha'$, and the height of the color measuring unit 10 from the surface to be measured 101 is a height that is same as the reference height h0. Simultaneously, an interval between the light projecting unit 20 and the light receiving unit 30 is changed to the interval w2, which is the same as in the reference position. The reference position is set as a color measurement position for generating color conversion information. Accordingly, at the color measurement position for generating color conversion information, the height of the color measuring unit 10 from the recording sheet 100 is the height that is the same as the reference height h0, the central axis of light flux from the light projecting unit 20 and the optical axis of the optical system for light receiving 31 of the light receiving unit 30 are caused to match on the surface to be measured 101, a relative position among the light projecting unit 20, the light receiving unit 30, and the surface to be measured 101 is set at the reference position, and the colors of the recording sheet 100 can be accurately measured.

Next, in Step S34, color measurement for a patch is executed at a color measurement position for generating color conversion information. At the color measurement position for generating color conversion information, the height of the color measuring unit 10 from the recording sheet 100 is the height that is the same as the reference height h0 and the central axis of light flux from the light projecting unit 20 and the optical axis of the optical system for light receiving 31 of the light receiving unit 30 can match on the surface to be measured 101. Thus, when executing color measurement, the occurrence of variations in the height of the color measuring unit 10 from the recording sheet 100 in the third direction Z can be suppressed and the occurrence of variations in lightness can be suppressed. Therefore, highly accurate color measurement can be performed on the recording sheet 100 by setting a relative position among the light projecting unit 20, the light receiving unit 30, and the surface to be measured 101 at the reference position. A patch can be formed by landing ink droplets discharged from the recording head on the surface to be measured 101, that is, performing so-called printing.

Then, in Step S35, color conversion information is generated from color measurement results of the patch. After then, printing is executed based on the color conversion information.

Although a case where the central axis of light flux emitted from the light projecting unit 20 and the optical axis of the optical system for light receiving 31 of the light receiving unit 30 match on the surface to be measured 101 at the first relative position (first color measurement position) as illustrated in FIG. 37 is given as an example in the embodiment, the invention is not particularly limited thereto. A case where the central axis of light flux emitted from the light projecting unit 20 and the optical axis of the optical system for light receiving 31 of the light receiving unit 30 do not match at the first relative position (first color measurement position) is also included in the embodiment. That is, a distance between the central axis of light flux emitted from the light projecting unit 20 and the optical axis of the optical system for light receiving 31 of the light receiving unit 30 on the surface to be measured 101 at the first relative position (first color measurement position) may be short compared to a distance at the second relative position (second color measurement position). That is, lightness becomes higher as a distance between the central axis of light flux emitted from the light projecting unit 20 and the optical axis of the optical system for light receiving 31 of the light receiving unit 30 on the surface to be measured 101 becomes shorter. Thus, by performing color measurement at the color measurement position, which is set as described above, based on the difference α between the first color measurement position, at which a lightness determination value is high compared to the second color measurement position, and the reference position, a relative position among the light projecting unit 20, the light receiving unit 30, and the surface to be measured 101 is brought closer to a reference position and color measurement can be performed with high accuracy compared to a case where color measurement is performed at the color measurement position, which is set as described above, based on the difference α between the second color measurement position and the reference position.

In addition, although color measurement is performed at two points (n=2), including the first relative position (first color measurement position) and the second relative position (second color measurement position) in the embodiment, the invention is not particularly limited thereto. Color measurement may be performed at three or more different relative positions. That is, color measurement may be performed at a plurality of relative positions with different intervals between the light projecting unit 20 and the light receiving unit 30, and the relative position at which the highest lightness is measured may be set as a color measurement position for generating color conversion information as described above based on the difference α between the first relative position and the reference position. Although it is desirable that a color measurement position for generating color conversion information be set as described above based on the difference α between the relative position, at which the highest lightness is measured, and the reference position in a case where color measurement is performed at a plurality of relative positions with different intervals between the light projecting unit 20 and the light receiving unit 30, a color measurement position for generating color conversion information can be set as described above based on the difference α between the relative position, at which higher lightness is measured, even though the lightness is not the highest, and the reference position. Also in this case, colors can be accurately measured than in a case where a color measurement position for generating color conversion information is set as described above based on the difference α between the relative position, at which lower lightness is measured, and the reference position. Accordingly, color measurement can be performed at high lightness and color measurement accuracy can be increased by bringing a relative position among the light projecting unit 20, the light receiving unit 30, and the surface to be measured 101, which is at the color measurement position for generating color conversion information, as close as possible to the reference position since a color measurement position for generating color conversion information can be set based on a difference between the relative position, at which a distance between the central axis of light flux emitted from the light projecting unit 20 and the optical axis of the optical system for light receiving 31 of the light receiving unit 30 is as short as possible, and the reference position.

In addition, highly accurate color measurement can be performed at higher lightness since a relative position among the light projecting unit 20, the light receiving unit 30, and the surface to be measured 101, which is at the color measurement position for generating color conversion information, can be brought as close as possible to the reference position by performing the setting of a color measurement position for generating color conversion information based on lightness determination values measured at three or more different relative positions with different intervals between the light projecting unit 20 and the light receiving unit 30.

Consequently, it is preferable to perform color measurement at as many relative positions with different intervals between the light projecting unit 20 and the light receiving unit 30 as possible, in order to perform color measurement on the surface to be measured 101 with higher accuracy. However, by increasing the number of relative positions for color measurement with different intervals between the light projecting unit 20 and the light receiving unit 30, the number of times of color measurement increases and thus it takes time for color measurement. Therefore, in a case where lightness when colors are accurately measured is known beforehand based on test results, a threshold is set based on the lightness, color measurement may be performed at a plurality of relative positions with different intervals between the light projecting unit 20 and the light receiving unit 30, and a color measurement position for generating color conversion information may be set as described above based on a relative position (first relative position) at which higher lightness than predetermined lightness (threshold) is measured. Accordingly, since a color measurement position for generating color conversion information can be set based on a difference between a relative position, at which a distance between the central axis of light flux emitted from the light projecting unit 20 and the optical axis of the optical system for light receiving 31 of the light receiving unit 30 is within a predetermined range, and a reference position, color measurement accuracy can be increased by bringing a relative position among the light projecting unit 20, the light receiving unit 30, and the surface to be measured 101, which is at the color measurement position for generating color conversion information, as close as possible to the reference position. In addition, it is not necessary to measure colors until the central axis of light flux emitted from the light projecting unit 20 and the optical axis of the optical system for light receiving 31 of the light receiving unit 30 match. Thus, the number of times of color measurement can be decreased and time necessary for color measurement can be shortened.

Since the reference position is a position where the central axis of light flux emitted from the light projecting unit 20 and the optical axis of the optical system for light receiving 31 of the light receiving unit 30 match on the surface to be measured 101A of the recording sheet 100A, which is reference, in an example described above, the thickness of the recording sheet 100 (for example, the thickness of the recording sheet 100A, which is reference, + difference α' in height), of which colors are measured, can also be calculated from the difference α between a reference interval between the light projecting unit 20 and the light receiving unit 30 and an interval between the light projecting unit 20 and the light receiving unit 30 or the difference α' between the reference height h0 in the third direction Z, which is calculated from the difference α in interval, and the height h5 at the first color measurement position. By detecting the thickness of the recording sheet 100, of which colors are to be measured, as described above, costs can be reduced since a separate sensor that measures the thickness of the recording sheet 100 is unnecessary, and miniaturization can be achieved since a space to dispose the sensor is unnecessary. In addition, the changing unit 40 can control a paper gap, which is an interval between the recording sheet 100 and the recording head 1, with high accuracy by acquiring the thickness of the recording sheet 100. Therefore, highly accurate printing can be realized.

In the embodiment, since the reference position is a position where the central axis of light flux from the light projecting unit 20 and the optical axis of the optical system for light receiving 31 of the light receiving unit 30 match on the surface to be measured 101A of the recording sheet 100A, of which a thickness is reference, colors can be measured without adjusting the height in a case where the recording sheet 100 having the same thickness as the thickness of the recording sheet 100A, which is reference, is used. Therefore, color measurement time can be shortened.

Although the reference position is a position where the central axis of light flux from the light projecting unit 20 and the optical axis of the optical system for light receiving 31 of the light receiving unit 30 match on surface to be measured 101A of the recording sheet 100A, which is reference, in an example described above, the invention is not particularly limited thereto.

For example, the reference position may be a position where the central axis of light flux from the light projecting unit 20 and the optical axis of the optical system for light receiving 31 of the light receiving unit 30 match on the supporting surface 8a of the supporting member 8. Due to this, from the difference α' between the reference height h0 in the third direction Z and the height h5 at the first color measurement position, a color measurement position for generating color conversion information can be set and the thickness of the recording sheet 100 can be calculated.

In addition, for example, the reference position may be any position. The difference α between an interval between the light projecting unit 20 and the light receiving unit 30, which is at any reference position as described above, and an interval between the light projecting unit 20 and the light receiving unit 30, which is at a relative position (first relative position) where the highest lightness is measured, is acquired. The difference α' between the height of the color measuring unit 10, which is at any reference position, in the third direction Z, and the height of the color measuring unit 10 from the surface to be measured 101, which is at the relative position where the highest lightness is measured, is calculated from the difference α in interval. The color measuring unit 10 is moved in the third direction Z by a distance obtained by adding a difference between the height of the color measuring unit 10, which is at any reference position, and the reference height h0 to the difference α'. When color measurement is performed in a state where the color measuring unit is moved, color measurement can be performed at the height h0 that is the same as the reference height h0 at all times. Therefore, the occurrence of variations in the height of the color measuring unit 10 from the surface to be measured 101, which is caused by variations in the thickness of the recording sheet 100, at a color measurement position for generating color conversion information can be suppressed. In addition, a relative position among the light projecting unit 20, the light receiving unit 30, and the surface to be measured 101 is set at the reference position and thus highly accurate color measurement can be performed.

Although a reference position is a second color measurement position, which is a second relative position, in an example described above, a reference position and a second relative position may be different positions, without being particularly limited thereto.

As described above, in the embodiment, in a driving method for a liquid ejecting apparatus including the recording head 1 that is an example of a liquid ejecting head ejecting an ink, which is a liquid, onto the recording sheet 100, which is a medium, and the color measuring unit 10 which includes the light projecting unit 20 irradiating the surface to be measured 101 of the recording sheet 100 with light and the light receiving unit 30 receiving the light, which is emitted from the light projecting unit 20 and is reflected by the surface to be measured 101 of the recording sheet 100, and measures the colors of the surface to be measured 101 of the recording sheet 100, the light projecting unit 20, the light receiving unit 30, and the recording sheet 100 are set at a first relative position. Light, which is emitted from the light projecting unit 20 and is reflected by the surface to be measured 101 of the recording sheet 100, is received by the light receiving unit 30, and a first color measurement value including a value indicating the lightness of the surface to be measured 101 of the recording sheet 100 is measured. The light projecting unit 20, the light receiving unit 30, and the recording sheet 100 are set a second relative position, which is different from the first relative position. Light, which is emitted from the light projecting unit 20 and is reflected by the surface to be measured 101 of the recording sheet 100, is received by the light receiving unit 30. A second color measurement value indicating the lightness of the surface to be measured 101 of the recording sheet 100 is measured. In a case where lightness indicated by the first color measurement value is higher than lightness indicated by the second color measurement value, a relative position among the light projecting unit 20, the light receiving unit 30, and the recording sheet 100 is set as a color measurement position based on a difference between the first relative position and the reference relative position set in advance. Print data is color-converted with color conversion information based on the colors of the recording sheet 100 measured at the color measurement position and the color measurement value of a patch printed on the recording sheet 100. As described above, in a case where lightness indicated by the first color measurement value, which is obtained at the first relative position, is higher than lightness indicated by the second color measurement value, which is obtained at the second relative position, the light projecting unit 20, the light receiving unit 30, and the surface to be measured 101 of the recording sheet (medium) 100 are set at a color measurement position, to which the same color measurement conditions as in the reference relative position are applied, based on a difference between the first relative position and the reference relative position, and color measurement is performed. For this reason, even when variations in the thickness of the recording sheet 100 occur, highly accurate color measurement can be performed since colors can be measured under a color measurement condition, in particular, a condition, in which the height of the color measuring unit 10 from the surface to be measured 101 is the same at all times, at the color measurement position.

Since it is desirable to perform color measurement at least two relative positions, including the first relative position and the second relative position, in the embodiment, color measurement time can be shortened.

In the embodiment, it is preferable that an interval between the light projecting unit 20 and the light receiving unit 30 in a direction intersecting the third direction Z, which is the normal line direction of the surface to be measured 101 of the recording sheet 100, which is a medium, differ at the first relative position and the second relative position. Accordingly, the reflection position of reflected light on the surface to be measured 101 of the recording sheet 100 is changed and highly accurate color measurement can be performed.

The changing unit 40 changes the position of the light projecting unit 20 in the second direction Y with respect to the light receiving unit 30 in the embodiment. Without being particularly limited thereto, the changing unit may change the position of the light receiving unit 30 in the second direction Y with respect to the light projecting unit 20.

In the embodiment, in a case where lightness indicated by the first color measurement value is higher than lightness indicated by the second color measurement value, it is preferable that the color measuring unit 10 be moved in the third direction Z, which is the normal line direction of the surface to be measured 101, by a distance calculated from a difference between an interval between the light projecting unit 20 and the light receiving unit 30, which is at the first relative position, and an interval between the light projecting unit 20 and the light receiving unit 30, which is at the reference relative position set in advance. According to this, even when variations in the thickness of the recording sheet 100 occur, highly accurate color measurement can be performed since colors can be measured under a condition in which the height of the color measuring unit 10 from the surface to be measured 101 is the same at all times.

It is preferable that the first relative position be a relative position, at which higher lightness is measured, out of a plurality of relative positions among the light projecting unit 20, the light receiving unit 30, and the recording sheet 100. According to this, color measurement accuracy can be increased by bringing a relative position among the light projecting unit 20, the light receiving unit 30, and the surface to be measured 101, which is at the color measurement position for generating color conversion information, as close as possible to the reference position since a color measurement position for generating color conversion information can be set based on a difference between the relative position, at which a distance between the central axis of light flux emitted from the light projecting unit 20 and the optical axis of the optical system for light receiving 31 of the light receiving unit 30 is as short as possible, and the reference position.

It is preferable that, the first relative position be a relative position, at which the highest lightness is measured, out of a plurality of relative positions among the light projecting unit 20, the light receiving unit 30, and the recording sheet 100. According to this, color measurement can be performed at high lightness and color measurement accuracy can be increased by bringing a relative position among the light projecting unit 20, the light receiving unit 30, and the surface to be measured 101, which is at the color measurement position for generating color conversion information, as close as possible to the reference position since a color measurement position for generating color conversion information can be set based on a difference between the relative position, at which a distance between the central axis of light flux emitted from the light projecting unit 20 and the optical axis of the optical system for light receiving 31 of the light receiving unit 30 is as short as possible, and the reference position.

Embodiment 8

Figure 38:
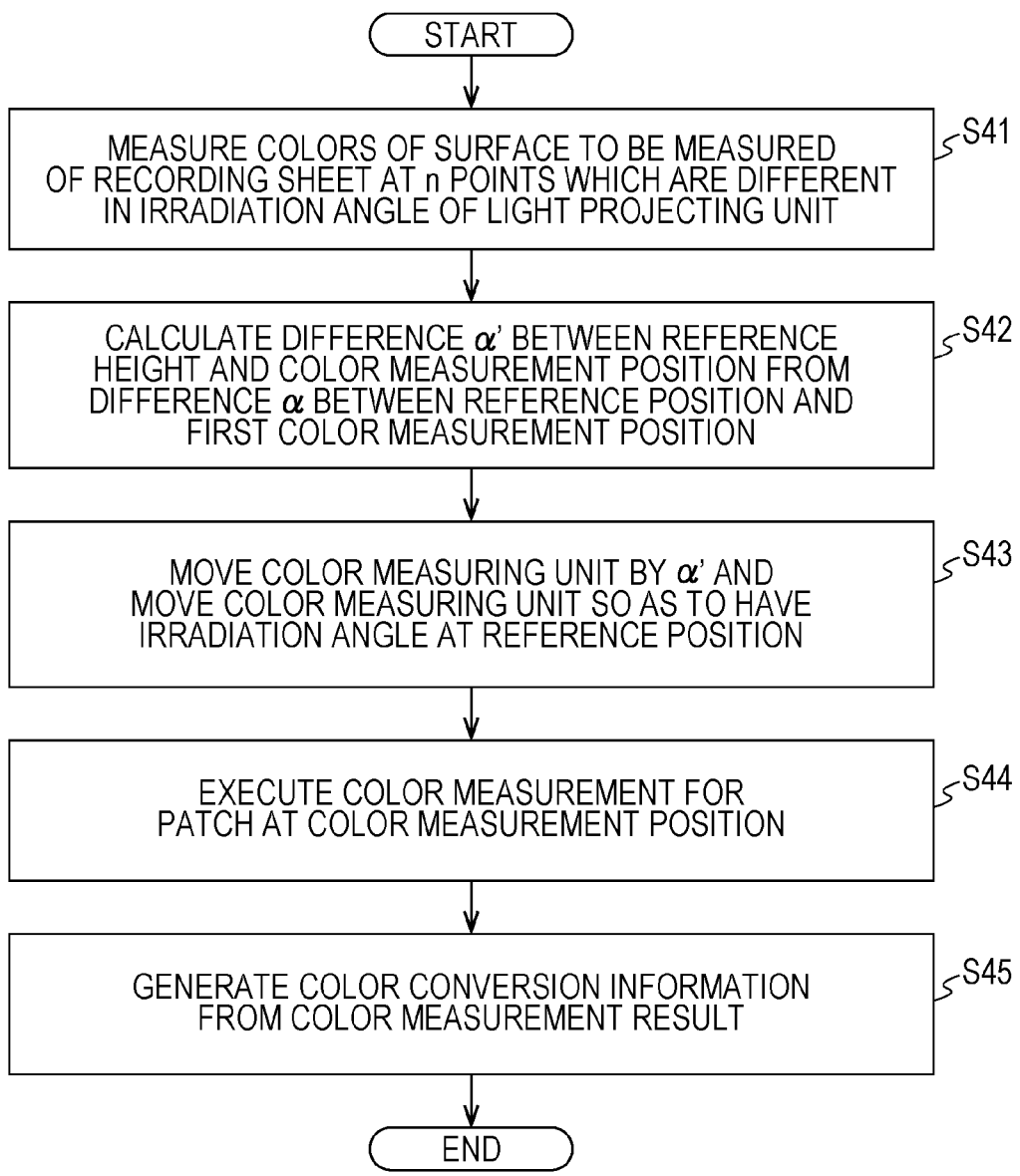
FIG. 38 is a flow chart showing a driving method according to Embodiment 8.

FIG. 38 is a flow chart showing a driving method for an ink jet recording apparatus, which is an example of a liquid ejecting apparatus according to Embodiment 8 of the invention, and FIG. 39 to FIG. 42 are side views of main portions of an ink jet recording apparatus. The same members as in the embodiment described above will be assigned with the same reference signs and overlapping description will be omitted.

Figure 42:
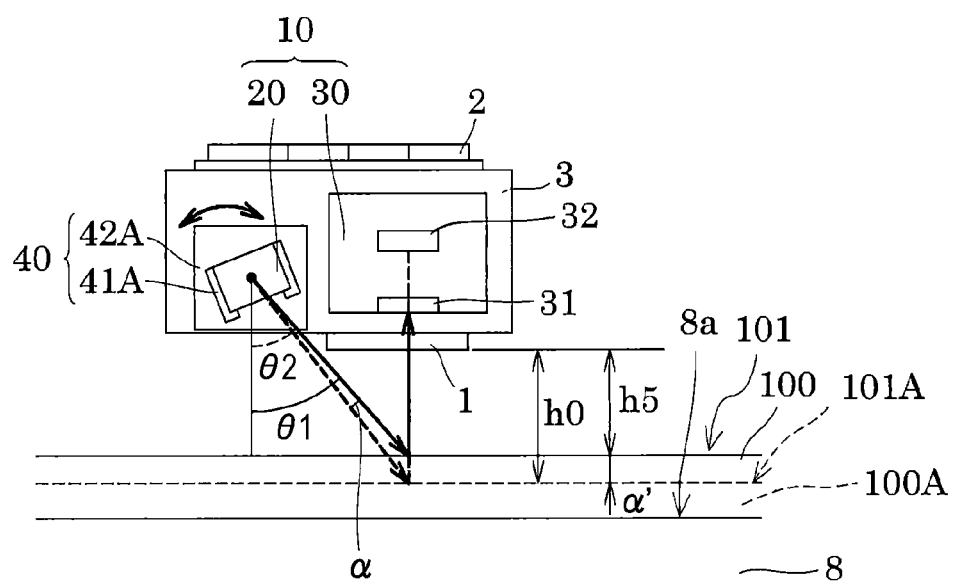
FIG. 42 is a side view of the main portions of the recording apparatus according to Embodiment 8.

As shown in FIG. 38, in a driving method for a liquid ejecting apparatus of Embodiment 8 of the invention, in Step S41, the colors of the surface to be measured 101 of the recording sheet 100 are measured at n points (n 2, n is a natural number), which are different in the irradiation angle of the light projecting unit 20, and generated color measurement data is associated with a color measurement position (position of the color measuring unit 10 in the third direction Z) and is stored in the memory unit 212. In the embodiment, colors are measured at two points (n=2), which are different in the irradiation angle of the light projecting unit 20. Specifically, as illustrated in FIG. 42, the colors of the surface to be measured 101 of the recording sheet 100 are measured at the first color measurement position where the irradiation angle of the light projecting unit 20 is the irradiation angle θ1 (herein, an angle between the central axis of light flux emitted from the light projecting unit 20 and the normal line of the surface to be measured 101) and at the second color measurement position where the irradiation angle of the light projecting unit 20 is the irradiation angle θ2 (herein, an angle between the central axis of light flux emitted from the light projecting unit 20 and the normal line of the surface to be measured 101, θ1≠θ2). That is, the light projecting unit 20, the light receiving unit 30, and the recording sheet 100 are set at a first relative position (first color measurement position where the irradiation angle of the light projecting unit 20 is θ1), and a first color measurement value including a value indicating the lightness of the surface to be measured 101 of the recording sheet 100 is measured. Specifically, the first color measurement value (color measurement data) quantified under the color system from results measured by the color measuring unit 10 at the first color measurement position is associated with the first color measurement position and is stored in the memory unit 212. In addition, the light projecting unit 20, the light receiving unit 30, and the recording sheet 100 are set at a second relative position (second color measurement position where the irradiation angle of the light projecting unit 20 is θ2), which is different from the first relative position, and a second color measurement value including a value indicating the lightness of the surface to be measured 101 of the recording sheet 100 is measured. Specifically, the second color measurement value (color measurement data) quantified under the color system from results measured by the color measuring unit 10 at the second color measurement position is associated with the second color measurement position and is stored in the memory unit 212. In the embodiment, at the first relative position (first color measurement position) and the second relative position (second color measurement position), the height of the color measuring unit 10 from the recording sheet 100 in the third direction Z is the reference height h0 or a predetermined height, the angle of the optical axis of the optical system for light receiving 31 of the light receiving unit 30 with respect to the normal line of the surface to be measured 101 is a reference angle, and an interval between the light projecting unit 20 and the light receiving unit 30 in the second direction Y is the same as the reference interval w0. Accordingly, at a color measurement position for generating color conversion information, which will be described later, a relative position among the light projecting unit 20, the light receiving unit 30, and the surface to be measured 101 is set at a reference position and the colors of the recording sheet 100 can be accurately measured. As a result, variations in color measurement accuracy, which are caused by variations in the thickness of the recording sheet 100, can be suppressed.

In addition, color measurement at the first color measurement position and the second color measurement position may be performed as follows. For example, the colors of the surface to be measured 101 of the recording sheet 100, that is, the colors of the recording sheet 100 itself may be measured, or the colors of a patch, on which ink droplets discharged from the recording head are landed, that is, so-called printing is performed, on the surface to be measured 101, may be measured.

Figure 39:
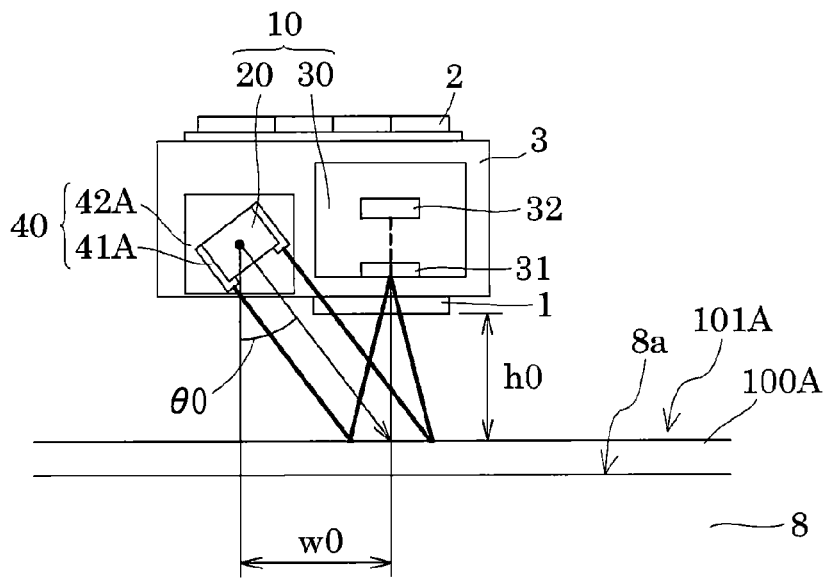
FIG. 39 is a side view of main portions of a recording apparatus according to Embodiment 8.

In the embodiment, as illustrated in FIG. 39, in a case where the recording sheet 100A, of which a thickness is reference, is used, a relative position among the light projecting unit 20, the light receiving unit 30, and the surface to be measured 101A, at which the colors of the reference recording sheet 100A can be appropriately measured, is set as a reference relative position. At the reference relative position, the height of the surface to be measured 101A of the color measuring unit 10 is the reference height h0, an interval between the light projecting unit 20 and the light receiving unit 30 in the second direction Y is the reference interval w0, the angle of the optical axis of the optical system for light receiving 31 of the light receiving unit 30 with respect to the normal line of the surface to be measured 101A is the reference angle, and the irradiation angle of the light projecting unit 20 with respect to the normal line of the surface to be measured 101A (angle of the central axis of light flux) is a reference angle θ0. At such a reference relative position, the central axis of light flux from the light projecting unit 20 and the optical axis of the optical system for light receiving 31 of the light receiving unit 30 match on the surface to be measured 101A of the recording sheet 100A, which is reference. That is, in a case where the light projecting unit 20, the light receiving unit 30, and the surface to be measured 101A of the recording sheet 100A, which is reference, are disposed at the reference relative position, lightness indicated by color measurement data is the highest. Information of a reference relative position indicating such a reference position where the light projecting unit 20, the light receiving unit 30, and the surface to be measured 101 are disposed is stored in the memory unit 212.

In the embodiment, a reference relative position (hereinafter, also simply referred to as a reference position) is set as the second color measurement position (second relative position). That is, a case where the irradiation angle θ2 of the light projecting unit 20 with respect to the normal line of the surface to be measured 101A (angle of the central axis of light flux) at the second relative position is equal to the reference angle θ0 will be described. When the colors of the surface to be measured 101 of the recording sheet 100, of which a thickness is different from the thickness of the reference recording sheet 100A, are measured at such a second relative position (reference position), a difference between the height of the color measuring unit 10 from the surface to be measured 101 in the third direction Z and the reference height h0 occurs by the amount of a difference between the thickness of the recording sheet 100A, which is reference, and the thickness of the recording sheet 100 and the central axis of light flux from the light projecting unit 20 and the optical axis of the optical system for light receiving 31 of the light receiving unit 30 are deviated from each other on the surface to be measured 101.

Figure 40:
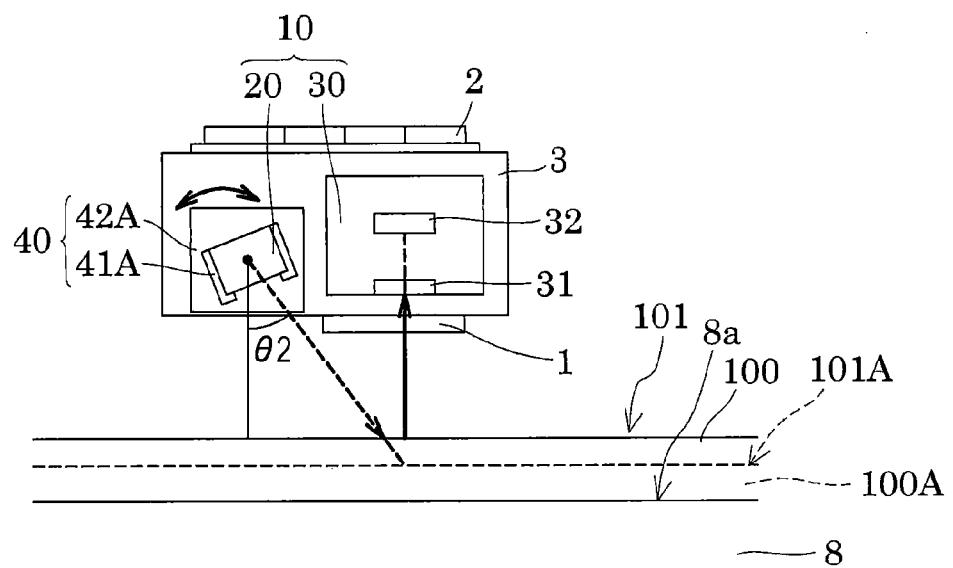
FIG. 40 is a side view of the main portions of the recording apparatus according to Embodiment 8.
Figure 41:
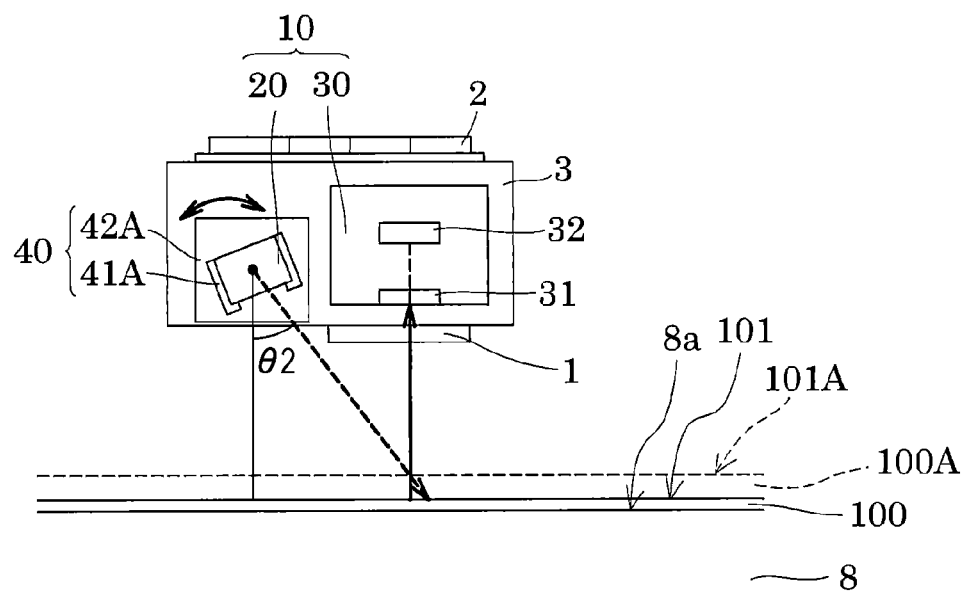
FIG. 41 is a side view of the main portions of the recording apparatus according to Embodiment 8.

For example, as illustrated in FIG. 40, in a case where the thickness of the recording sheet 100 is larger than the thickness of the recording sheet 100A, which is reference, the central axis of light flux from the light projecting unit 20 and the optical axis of the optical system for light receiving 31 of the light receiving unit 30 are at different positions on the surface to be measured 101, at the second color measurement position (reference position). As illustrated in FIG. 41, also in a case where the thickness of the recording sheet 100 is smaller than the thickness of the recording sheet 100A, which is reference, the central axis of light flux from the light projecting unit 20 and the optical axis of the optical system for light receiving 31 of the light receiving unit 30 are at different positions on the surface to be measured 101, at the second color measurement position (reference position).

In the embodiment, the control unit for a color measuring unit 300 controls the color measuring unit 10 to perform color measurement while the control unit for a changing unit 302 controlling the changing unit 40 to change the angle of the central axis of light flux emitted from the light projecting unit 20 with respect to the normal line of the surface to be measured 101 (irradiation angle of the light projecting unit 20). The color measurement processing unit 301 quantifies colors under the color system and generates color measurement data from measurement results from the color measuring unit 10. The color measurement data is associated with reflection position data and is stored in the memory unit 212. In the embodiment, the angle of the central axis of light flux emitted from the light projecting unit 20 with respect to the normal line of the surface to be measured 101 (irradiation angle of the light projecting unit 20) is reflection position data. Next, reflection position data associated with color measurement data, which is determined as color measurement data indicating the highest lightness by the lightness determining unit 303, is identified from a plurality of pieces of color measurement data. For example, in a case where the thickness of the recording sheet 100 illustrated in FIG. 40 is larger than the thickness of the recording sheet 100A, which is reference, the central axis of light flux from the light projecting unit 20 and the optical axis of the optical system for light receiving 31 of the light receiving unit 30 match on the surface to be measured 101 at the irradiation angle θ1, which is larger than the irradiation angle θ2 of the light projecting unit 20, as illustrated in FIG. 42, and the light receiving unit 30 can receive the strongest light. Consequently, the irradiation angle θ1 of the light projecting unit 20, which is at the first color measurement position, can be identified as reflection position data indicating the highest lightness.

Next, in Step S42, the difference α' between the reference height h0 of the color measuring unit 10 from the surface to be measured 101A in the third direction Z and the height h5 of the color measuring unit 10 from the surface to be measured 101 in the third direction Z, which is at the first color measurement position, is calculated from the difference α (θ2−θ1) between the irradiation angle θ2 of the light projecting unit 20, which is at the reference position, and the irradiation angle θ1 of the light projecting unit 20, which is at the first color measurement position that is reflection position data associated with the color measurement data determined as data indicating the highest lightness in Step S41. For example, a conversion table, in which the difference α between the irradiation angle θ2 of the light projecting unit 20, which is at the reference position, and the irradiation angle θ1 of the light projecting unit 20, which is at the first color measurement position, and the difference α' between the reference height h0 of the color measuring unit 10 from the surface to be measured 101A and the height h5 of the color measuring unit 10 from the surface to be measured 101, which is at the first color measurement position, are associated with each other, is prepared. Based on the conversion table, the difference α' between the reference height h0 of the color measuring unit 10 in the third direction Z and the height h5 at the first color measurement position is acquired from the difference α between the irradiation angles θ1 and θ2 of the light projecting unit 20.

Next, in Step S43, the color measuring unit 10 is moved from the height h5 from the surface to be measured 101 at the first color measurement position in the third direction Z by the difference α', and the height of the color measuring unit 10 from the surface to be measured 101 is a height that is same as the reference height h0. Simultaneously, the irradiation angle of the light projecting unit 20 is changed from θ1 to the irradiation angle θ2, which is the same as in the reference position. The reference position is set as a color measurement position for generating color conversion information. Accordingly, at the color measurement position for generating color conversion information, the height of the color measuring unit 10 from the recording sheet 100 is the height that is the same as the reference height h0, the central axis of light flux from the light projecting unit 20 and the optical axis of the optical system for light receiving 31 of the light receiving unit 30 are caused to match on the surface to be measured 101, a relative position among the light projecting unit 20, the light receiving unit 30, and the surface to be measured 101 is set at the reference position, and the colors of the recording sheet 100 can be accurately measured.

Next, in Step S44, color measurement for a patch is executed at a color measurement position for generating color conversion information. At the color measurement position for generating color conversion information, the height of the color measuring unit 10 from the recording sheet 100 is the height that is the same as the reference height h0 and the central axis of light flux from the light projecting unit 20 and the optical axis of the optical system for light receiving 31 of the light receiving unit 30 can match on the surface to be measured 101. Thus, when executing color measurement, the occurrence of variations in the height of the color measuring unit 10 from the recording sheet 100 in the third direction Z can be suppressed and the occurrence of variations in lightness can be suppressed. Therefore, highly accurate color measurement can be performed on the recording sheet 100 by disposing a relative position among the light projecting unit 20, the light receiving unit 30, and the surface to be measured 101 at the reference position at all times. A patch can be formed by landing ink droplets discharged from the recording head 1 onto the surface to be measured 101, that is, performing so-called printing.

Then, in Step S45, color conversion information is generated from color measurement results of the patch. After then, printing is executed based on the color conversion information.

Although a case where the central axis of light flux emitted from the light projecting unit 20 and the optical axis of the optical system for light receiving 31 of the light receiving unit 30 match on the surface to be measured 101 at the first relative position (first color measurement position) as illustrated in FIG. 42 is given as an example in the embodiment, the invention is not particularly limited thereto. A case where the central axis of light flux emitted from the light projecting unit 20 and the optical axis of the optical system for light receiving 31 of the light receiving unit 30 do not match at the first relative position (first color measurement position) is also included in the embodiment. That is, a distance between the central axis of light flux emitted from the light projecting unit 20 and the optical axis of the optical system for light receiving 31 of the light receiving unit 30 on the surface to be measured 101 at the first relative position (first color measurement position) may be short compared to a distance at the second relative position (second color measurement position). That is, lightness becomes higher as a distance between the central axis of light flux emitted from the light projecting unit 20 and the optical axis of the optical system for light receiving 31 of the light receiving unit 30 on the surface to be measured 101 becomes shorter. Thus, by performing color measurement at the color measurement position, which is set as described above, based on the difference α between the first color measurement position, at which a lightness determination value is high compared to the second color measurement position, and the reference position, a relative position among the light projecting unit 20, the light receiving unit 30, and the surface to be measured 101 is brought closer to a reference position and color measurement can be performed with high accuracy compared to a case where color measurement is performed at the color measurement position, which is set as described above, based on the difference α between the second color measurement position and the reference position.

In addition, although color measurement is performed at two points (n=2), including the first relative position (first color measurement position) and the second relative position (second color measurement position) in the embodiment, the invention is not particularly limited thereto. Color measurement may be performed at three or more different relative positions. That is, color measurement may be performed at a plurality of relative positions where intervals with different irradiation angles of the light projecting unit 20, and the relative position at which the highest lightness is measured may be set as a color measurement position for generating color conversion information as described above based on the difference α between the first relative position and the reference position. Although it is desirable that a color measurement position for generating color conversion information be set as described above based on the difference α between the relative position, at which the highest lightness is measured, and the reference position in a case where color measurement is performed at a plurality of relative positions with different irradiation angles of the light projecting unit 20, a color measurement position for generating color conversion information can also be set as described above based on the difference α between the relative position, at which higher lightness is measured, even though the lightness is not the highest, and the reference position. Also in this case, colors can be accurately measured than in a case where a color measurement position for generating color conversion information is set as described above based on the difference α between the relative position, at which lower lightness is measured, and the reference position. Accordingly, color measurement can be performed at high lightness and color measurement accuracy can be increased by bringing a relative position among the light projecting unit 20, the light receiving unit 30, and the surface to be measured 101, which is at the color measurement position for generating color conversion information, as close as possible to the reference position since a color measurement position for generating color conversion information can be set based on a difference between the relative position, at which a distance between the central axis of light flux emitted from the light projecting unit 20 and the optical axis of the optical system for light receiving 31 of the light receiving unit 30 on the surface to be measured 101 is as short as possible, and the reference position.

In addition, highly accurate color measurement can be performed at higher lightness since a relative position among the light projecting unit 20, the light receiving unit 30, and the surface to be measured 101, which is at the color measurement position for generating color conversion information, can be brought as close as possible to the reference position by performing the setting of a color measurement position for generating color conversion information based on lightness determination values, at which colors are measured at three or more different relative positions with different irradiation angles of the light projecting unit 20. Consequently, it is preferable to perform color measurement at as many relative positions with different irradiation angles of the light projecting unit 20 as possible, in order to perform color measurement on the surface to be measured 101 with higher accuracy. However, by increasing the number of relative positions for color measurement with different irradiation angles of the light projecting unit 20, the number of times of color measurement increases and thus it takes time for color measurement. Therefore, in a case where lightness when colors are accurately measured is known beforehand based on test results, a threshold is set based on the lightness, color measurement may be performed at a plurality of relative positions with different irradiation angles of the light projecting unit 20, and a color measurement position for generating color conversion information may be set as described above based on a relative position (first relative position) at which higher lightness than predetermined lightness (threshold) is measured. Accordingly, since a color measurement position for generating color conversion information can be set based on a difference between a relative position, at which a distance between the central axis of light flux emitted from the light projecting unit 20 and the optical axis of the optical system for light receiving 31 of the light receiving unit 30 on the surface to be measured 101 is within a predetermined range, and a reference position, color measurement accuracy can be increased by bringing a relative position among the light projecting unit 20, the light receiving unit 30, and the surface to be measured 101, which is at the color measurement position for generating color conversion information, as close as possible to the reference position. In addition, it is not necessary to measure colors until the central axis of light flux emitted from the light projecting unit 20 and the optical axis of the optical system for light receiving 31 of the light receiving unit 30 match. Thus, the number of times of color measurement can be decreased and time necessary for color measurement can be shortened.

Since the reference position is a position where the central axis of light flux emitted from the light projecting unit 20 and the optical axis of the optical system for light receiving 31 of the light receiving unit 30 match on the surface to be measured 101A of the recording sheet 100A, which is reference, in an example described above, the thickness of the recording sheet 100 (for example, the thickness of the recording sheet 100A, which is reference, + difference α' in height), of which colors are measured, can also be calculated from the difference α between the irradiation angle of the light projecting unit 20, which is reference, and the irradiation angle of the light projecting unit 20, which is at the first relative position where the highest lightness is measured, or the difference α' between the reference height h0 in the third direction Z, which is calculated from the difference α in irradiation angle, and the height h5 at the first color measurement position. By detecting the thickness of the recording sheet 100, of which colors are to be measured, as described above, costs can be reduced since a separate sensor that measures the thickness of the recording sheet 100 is unnecessary, and miniaturization can be achieved since a space to dispose the sensor is unnecessary. In addition, the changing unit 40 can control a paper gap, which is an interval between the recording sheet 100 and the recording head 1, with high accuracy by acquiring the thickness of the recording sheet 100. Therefore, highly accurate printing can be realized.

In the embodiment, since the reference position is a position where the central axis of light flux from the light projecting unit 20 and the optical axis of the optical system for light receiving 31 of the light receiving unit 30 match on the surface to be measured 101A of the recording sheet 100A, of which a thickness is reference, colors can be measured without adjusting the height in a case where the recording sheet 100 having the same thickness as the thickness of the recording sheet 100A, which is reference, is used. Therefore, color measurement time can be shortened.

Although the reference position is a position where the central axis of light flux from the light projecting unit 20 and the optical axis of the optical system for light receiving 31 of the light receiving unit 30 match on surface to be measured 101A of the recording sheet 100A, which is reference, in an example described above, the invention is not particularly limited thereto.

For example, the reference position may be a position where the central axis of light flux from the light projecting unit 20 and the optical axis of the optical system for light receiving 31 of the light receiving unit 30 match on the supporting surface 8a of the supporting member 8. Due to this, from the difference α' between the reference height h0 in the third direction Z and the height h5 at the first color measurement position, the thickness of the recording sheet 100 can also be calculated.

In addition, for example, the reference position may be any position. The difference α between the irradiation angle of the light projecting unit 20, which is at any reference position as described above, and the irradiation angle of the light projecting unit 20, which is at a relative position (first relative position) where the highest lightness is measured, is acquired. The difference α' between the height of the color measuring unit 10 from the surface to be measured 101, which is at any reference position in the third direction Z, and the height h5 of the color measuring unit 10 from the surface to be measured 101, which is at the relative position where the highest lightness is measured, is calculated from the difference α in irradiation angle. The color measuring unit 10 is moved in the third direction Z by a distance obtained by adding a difference between the height of the color measuring unit 10, which is at any reference position, and the reference height h0 to the difference α'. When color measurement is performed in a state where the color measuring unit is moved, color measurement can be performed at the height h0 that is the same as the reference height h0 at all times. Therefore, the occurrence of variations in the height of the color measuring unit 10 from the surface to be measured 101, which is caused by variations in the thickness of the recording sheet 100, at a color measurement position for generating color conversion information can be suppressed. In addition, a relative position among the light projecting unit 20, the light receiving unit 30, and the surface to be measured 101 is set at the reference position and thus highly accurate color measurement can be performed.

Although a reference position is a second color measurement position, which is a second relative position, in an example described above, a reference position and a second relative position may be different positions, without being particularly limited thereto.

As described above, in the embodiment, in a driving method for a liquid ejecting apparatus including the recording head 1 that is an example of a liquid ejecting head ejecting an ink, which is a liquid, onto the recording sheet 100, which is a medium, and the color measuring unit 10 which includes the light projecting unit 20 irradiating the surface to be measured 101 of the recording sheet 100 with light and the light receiving unit 30 receiving the light, which is emitted from the light projecting unit 20 and is reflected by the surface to be measured 101 of the recording sheet 100, and measures the colors of the surface to be measured 101 of the recording sheet 100, the light projecting unit 20, the light receiving unit 30, and the recording sheet 100 are set at a first relative position. Light, which is emitted from the light projecting unit 20 and is reflected by the surface to be measured 101 of the recording sheet 100, is received by the light receiving unit 30, and a first color measurement value including a value indicating the lightness of the surface to be measured 101 of the recording sheet 100 is measured. The light projecting unit 20, the light receiving unit 30, and the recording sheet 100 are set at a second relative position, which is different from the first relative position. Light, which is emitted from the light projecting unit 20 and is reflected by the surface to be measured 101 of the recording sheet 100, is received by the light receiving unit 30. A second color measurement value indicating the lightness of the surface to be measured 101 of the recording sheet 100 is measured. In a case where lightness indicated by the first color measurement value is higher than lightness indicated by the second color measurement value, a relative position among the light projecting unit 20, the light receiving unit 30, and the recording sheet 100 is set as a color measurement position based on a difference between the first relative position and the reference relative position set in advance. Print data is color-converted with color conversion information based on the colors of the recording sheet 100 measured at the color measurement position and the color measurement value of a patch printed on the recording sheet 100. As described above, in a case where lightness indicated by the first color measurement value, which is obtained at the first relative position, is higher than lightness indicated by the second color measurement value, which is obtained at the second relative position, the light projecting unit 20, the light receiving unit 30, and the surface to be measured 101 of the recording sheet (medium) 100 are set at a color measurement position, to which the same color measurement conditions as in the reference relative position are applied, based on a difference between the first relative position and the reference relative position, and color measurement is performed. For this reason, even when variations in the thickness of the recording sheet 100 occur, highly accurate color measurement can be performed since colors can be measured under a color measurement condition, in particular, a condition, in which the height of the color measuring unit 10 from the surface to be measured 101 is the same at all times, at the color measurement position.

Since it is desirable to perform color measurement at least two relative positions, including the first relative position and the second relative position, in the embodiment, color measurement time can be shortened.

In the embodiment, it is preferable that the angle of the central axis of light flux emitted from the light projecting unit 20 with respect to the third direction Z, which is the normal line direction of the surface to be measured 101, differ at the first relative position and the second relative position. Accordingly, the reflection position of reflected light on the surface to be measured 101 of the recording sheet 100 is changed and highly accurate color measurement can be performed.

In the embodiment, in a case where lightness indicated by the first color measurement value is higher than lightness indicated by the second color measurement value, it is preferable that the color measuring unit 10 be moved in the third direction Z, which is the normal line direction of the surface to be measured 101, by a distance calculated from a difference between the angle of the central axis of light flux emitted from the light projecting unit 20 with respect to the normal line of the surface to be measured 101, which is at first relative position, and the angle of the central axis of light flux emitted from the light projecting unit 20 with respect to the normal line of the surface to be measured 101, which is at the reference relative position set in advance. According to this, even when variations in the thickness of the recording sheet 100 occur, highly accurate color measurement can be performed since colors can be measured under a condition in which the height of the color measuring unit 10 from the surface to be measured 101 is the same at all times.

It is preferable that the first relative position be a relative position, at which higher lightness is measured, out of a plurality of relative positions among the light projecting unit 20, the light receiving unit 30, and the recording sheet 100. According to this, color measurement can be performed at high lightness and color measurement accuracy can be increased by bringing a relative position among the light projecting unit 20, the light receiving unit 30, and the surface to be measured 101, which is at the color measurement position for generating color conversion information, as close as possible to the reference position since a color measurement position for generating color conversion information can be set based on a difference between the relative position, at which a distance between the central axis of light flux emitted from the light projecting unit 20 and the optical axis of the optical system for light receiving 31 of the light receiving unit 30 is as short as possible, and the reference position.

It is preferable that, the first relative position be a relative position, at which the highest lightness is measured, out of a plurality of relative positions among the light projecting unit 20, the light receiving unit 30, and the recording sheet 100. According to this, color measurement can be performed at high lightness and color measurement accuracy can be increased by bringing a relative position among the light projecting unit 20, the light receiving unit 30, and the surface to be measured 101, which is at the color measurement position for generating color conversion information, as close as possible to the reference position since a color measurement position for generating color conversion information can be set based on a difference between the relative position, at which a distance between the central axis of light flux emitted from the light projecting unit 20 and the optical axis of the optical system for light receiving 31 of the light receiving unit 30 is as short as possible, and the reference position.

Other Embodiments

Although each of the embodiments of the invention has been described hereinbefore, a basic configuration of the invention is not limited to the embodiments described above.

For example, although the central axis of light flux emitted from the light projecting unit 20 is tilted at 45 degrees with respect to the third direction Z (the normal line direction of the surface to be measured 101) in each embodiment described above, the invention is not particularly limited thereto. For example, the central axis of light flux emitted from the light projecting unit 20 may be in a direction along the third direction Z (the normal line direction of the surface to be measured 101), and the light receiving angle of the light receiving unit 30 (optical axis of the optical system for light receiving 31) may be inclined toward the light projecting unit 20 at 45 degrees with respect to the third direction Z (the normal line direction of the surface to be measured 101). Also in this case, lightness is made higher by causing reflected light, which is obtained by diffuse-reflecting light that matches the central axis of light flux emitted from the light projecting unit 20 on the surface to be measured 101, to match the optical axis of the optical system for light receiving 31 of the light receiving unit 30, and thus measurement accuracy can be improved.

In addition, although the ink jet recording apparatus I described above, in which the recording head 1 is mounted on the carriage 3 and is moved in the second direction Y, is given as an example, the invention is not limited thereto. For example, the invention can also be applied to a so-called line-type recording apparatus, in which the recording head 1 is fixed to the apparatus main body 4 and which performs printing by moving the recording sheet 100, such as paper, in the first direction X. However, when providing the color measuring unit 10 in the line-type recording apparatus, the color measuring unit 10 may be mounted on a carriage for a color measuring unit which is provided so as to be movable in the second direction Y.

Although the color measuring unit 10 is mounted on the carriage 3 and is moved in the second direction Y in each embodiment described above, the invention is not limited thereto. For example, if a plurality of color measuring units 10 are provided for each patch, of which colors are to be measured, so as to be arranged in the second direction Y, the color measuring units 10 may not move in the second direction Y. In addition, the light receiving element 32 of the light receiving unit 30 may be provided so as to be arranged in the second direction Y.

For example, in a case where a transparent material is used for the recording sheet 100, light may be reflected with the use of a portion where ink droplets are landed on the surface to be measured 101. That is, since the transparent material transmits light, light is reflected by the outer surface of the supporting member 8 if the light is not reflected by the portion where ink droplets are landed. In the invention, the color measurement on the surface to be measured 101 includes a case where the colors of the outer surface of the recording sheet 100 are directly measured and a case where the colors of ink droplets printed on the surface to be measured 101 (patch) are measured.

When the height of the color measuring unit 10 from the surface to be measured 101 is changed in the third direction Z and colors are measured as in Embodiments 5 and 6 described above, the illuminance of light emitted from the light projecting unit 20 to the recording sheet 100 changes with a change in the height of the color measuring unit 10 from the surface to be measured 101. Thus, in some cases, the value of lightness measured at a relative position where the position of the central axis of light flux emitted from the light projecting unit 20 is separated from the position of the optical axis of the optical system for light receiving 31 of the light receiving unit 30 on the recording sheet 100 is equal to or higher than the value of lightness measured at a relative position where the central axis of light flux emitted from the light projecting unit 20 and the optical axis of the optical system for light receiving 31 of the light receiving unit 30 substantially match on the recording sheet 100. However, since color measurement is performed at the first color measurement position and the second color measurement position without changing the height of the color measuring unit 10 from the recording sheet 100 in the third direction Z in Embodiment 7 and Embodiment 8, a change in the illuminance of light flux emitted from the light projecting unit 20 on the recording sheet 100 (supporting surface 8*a*), which is caused by changing the height of the color measuring unit 10 from the surface to be measured 101 at the first color measurement position and the second color measurement position, can be suppressed. Therefore, in Embodiment 7 and Embodiment 8, a relative position, which is a color measurement position or a reference position, can be identified with high accuracy compared to Embodiments 5 and 6, a color measurement position for generating color conversion information can be set, and the thickness of the recording sheet 100 can be detected.

Since the height of the color measuring unit 10 from the surface to be measured 101 in the third direction Z is changed to set a relative position, at which color measurement data indicating high lightness is obtained, as a color measurement position for generating color conversion information as it is or to detect a difference between the reference position and the relative value as the thickness of the recording sheet 100 as it is, color measurement and the detection of the thickness of the recording sheet 100 are performed, deterioration in the accuracy of color measurement for generating color conversion information, which is caused by variations in the height of the color measuring unit 10 from the surface to be measured 101, is suppressed, and color measurement accuracy can be improved with a simple configuration and a simple technique in Embodiments 5 and 6 described above, compared to Embodiments 7 and 8 in which the light projecting unit 20, the light receiving unit 30, and the surface to be measured 101 are moved to a color measurement position for generating color conversion information based on a difference between the relative position, at which color measurement data indicating high lightness is obtained, and the reference position, or the thickness of the recording sheet 100 is converted from the difference between the relative position and the reference position.

In the embodiment, the height of the color measuring unit 10 from the surface to be measured 101 (supporting surface 8*a*) is a reference height, an interval between the light projecting unit 20 and the light receiving unit 30 is a reference interval, an angle between the central axis of light flux emitted from the light projecting unit 20 and the optical axis of the optical system for light receiving 31 of the light receiving unit 30 with respect to the normal line of the surface to be measured 101 (supporting surface 8*a*) is a reference angle, and a reference relative position where the central axis of light flux emitted from the light projecting unit 20 and the optical axis of the optical system for light receiving 31 of the light receiving unit 30 match on the surface to be measured 101 (supporting surface 8*a*) can be a dispositional position that satisfies JIS, ASTM, ISO, and CIE requirements related to color measurement.

The invention is widely applicable to liquid ejecting apparatuses having liquid ejecting heads and can also be used in, for example, liquid ejecting apparatuses that use recording heads, such as various ink jet recording heads used in image recording apparatuses, such as printers, color material ejecting heads used in manufacturing color filters, such as liquid crystal displays, electrode material ejecting heads used in forming electrodes, such as organic EL displays and field emission displays (FED), and bioorganic material ejecting heads used in manufacturing biochips.

The entire disclosure of Japanese Patent Application No. 2016-186763, filed Sep. 26, 2016 and Japanese Patent Application No. 2017-142276, filed Jul. 21, 2017 are expressly incorporated by reference herein.

What is claimed is:

1. A liquid ejecting apparatus comprising:
   a liquid ejecting head configured to eject a liquid onto a medium;
   a color measuring unit configured to perform color measurement on a surface to be measured of the medium, the color measuring unit having a light projecting unit, which emits a light flux to the surface to be measured of the medium, and a light receiving unit, which receives reflected light obtained by reflecting light emitted from the light projecting unit on the surface to be measured of the medium;
   a changing unit configured to change a reflection position of light, which matches a central axis of the light flux emitted from the light projecting unit, on the medium; and
   a control unit configure to control the changing unit, such that the changing unit sets a color measurement position to the reflection position where the color measuring unit obtains a color measurement datum indicating the highest lightness, out of color measurement data pieces of the surface to be measured, which are obtained by the color measuring unit measuring colors at the reflection position changed by the changing unit.

2. The liquid ejecting apparatus according to claim 1,
   wherein the control unit controls the changing unit to set a position where color measurement data indicating the highest lightness is obtained by the color measuring unit measuring colors when the light receiving unit receives light reflected by an outer surface of a supporting member supporting an opposite surface of the surface to be measured of the medium as a reference position, and acquires a thickness of the medium based on the reference position and the color measurement position.

3. The liquid ejecting apparatus according to claim 2,
   wherein the control unit identifies the medium based on the thickness of the medium and a color measurement result of a non-landing region where the liquid is not landed on the medium, of which colors are measured by the color measuring unit at the color measurement position.

4. The liquid ejecting apparatus according to claim 1,
   wherein the changing unit changes an interval between the color measuring unit and the medium in a normal line direction of the surface to be measured of the medium.

5. The liquid ejecting apparatus according to claim 1,
   wherein the color measuring unit is provided on an upstream side of the liquid ejecting head in a transporting direction of the medium.

6. The liquid ejecting apparatus according to claim 1,
   wherein the liquid ejecting head and the color measuring unit are mounted on a carriage that is provided so as to be movable in a direction orthogonal to a transporting direction of the medium and a direction orthogonal to the surface to be measured.

7. The liquid ejecting apparatus according to claim 1,
   wherein the control unit color-converts print data with color conversion information that is based on a color measurement value, which is obtained by the color measuring unit measuring colors of the surface to be measured at the color measurement position, or a color measurement value of a patch printed on the surface to be measured.

8. A method for measuring color of a surface of a medium onto which a liquid ejecting apparatus print, the liquid ejecting apparatus comprising a liquid ejecting head configure to eject a liquid onto the medium, a color measuring unit configure to perform color measurement on the surface to be measured of the medium, the color measuring unit having a light projecting unit, which emits a light flux to the surface to be measured of the medium, and a light receiving unit, which receives reflected light obtained by reflecting light emitted from the light projecting unit on the surface to be measured of the medium, the method comprising:

obtaining color measurement data by measuring colors of the surface to be measured by the color measuring unit with changing a reflection position of light, which matches a central axis of a light flux emitted from the light projecting unit, on the medium; and measuring color of the surface of the medium by means of the color measuring unit at a color measurement position that is the reflection position where the color measuring unit obtained a color measurement datum indicating the highest lightness among the color measurement data obtained at different reflection positions.

* * * * *